United States Patent
Yamada et al.

(10) Patent No.: US 11,319,483 B2
(45) Date of Patent: May 3, 2022

(54) ORGANIC COMPOUND, ELECTROCHROMIC ELEMENT CONTAINING THE SAME, OPTICAL FILTER, LENS UNIT, IMAGING DEVICE, AND WINDOW MATERIAL

(71) Applicant: CANON KABUSHIKI KAISHA, Tokyo (JP)

(72) Inventors: Kenji Yamada, Yokohama (JP); Satoshi Igawa, Fujisawa (JP); Wataru Kubo, Inagi (JP); Yuto Ito, Koganei (JP); Isao Kawata, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 474 days.

(21) Appl. No.: 16/240,490

(22) Filed: Jan. 4, 2019

(65) Prior Publication Data
US 2019/0136125 A1    May 9, 2019

Related U.S. Application Data

(63) Continuation of application No. 15/498,339, filed on Apr. 26, 2017, now Pat. No. 10,208,244.

(30) Foreign Application Priority Data

Apr. 27, 2016  (JP) .................................. 2016-089721
Apr. 4, 2017  (JP) .................................. 2017-074833

(51) Int. Cl.
*G02F 1/153*  (2006.01)
*C09K 9/02*  (2006.01)
(Continued)

(52) U.S. Cl.
CPC .............. *C09K 9/02* (2013.01); *C07D 241/46* (2013.01); *E06B 3/6722* (2013.01); *E06B 9/24* (2013.01);
(Continued)

(58) Field of Classification Search
CPC .................................. G02F 1/1516; G02F 1/155
See application file for complete search history.

(56) References Cited

U.S. PATENT DOCUMENTS 10,208,244 B2 *   2/2019   Yamada ................... C09K 9/02
2007/0008603 A1 *   1/2007   Sotzing ................... C09K 9/02
                                                        359/265

(Continued)

*Primary Examiner* — Joseph P Martinez
(74) *Attorney, Agent, or Firm* — Canon U.S.A., Inc. IP Division

(57) ABSTRACT

An organic compound represented by the following general formula is provided.

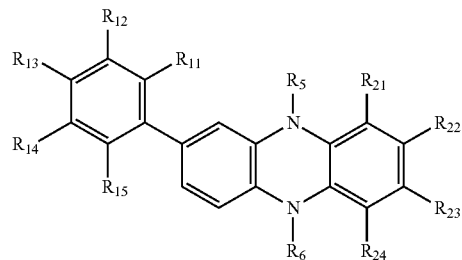

In the above formula (1), $R_{11}$ to $R_{15}$ each independently represent a hydrogen atom, an alkyl group, an alkoxy group, an aryl group, an aryloxy group, an aralkyl group, an acyl group, or a halogen atom provided that at least one of $R_{11}$, $R_{13}$, and $R_{15}$ represents the alkoxy group or the aryloxy group; and $R_{11}$ to $R_{15}$ may form a ring structure therebetween. $R_5$ and $R_6$ each independently represent an alkyl group, an aryl group, or an aralkyl group. In addition, $R_{21}$ to $R_{24}$ each independently represent a hydrogen atom, an alkyl group, an alkoxy group, an aryl group, an aryloxy group, an aralkyl group, an acyl group, or a halogen atom and may (Continued)

form a ring structure therebetween. The above groups except the acyl group may be substituted when necessary.

12 Claims, 6 Drawing Sheets

(51) Int. Cl.
*C07D 241/46* (2006.01)
*G02F 1/155* (2006.01)
*E06B 9/24* (2006.01)
*E06B 3/67* (2006.01)
*G02F 1/1516* (2019.01)

(52) U.S. Cl.
CPC ............ *G02F 1/155* (2013.01); *G02F 1/1516* (2019.01); *C09K 2211/1007* (2013.01); *C09K 2211/1044* (2013.01); *E06B 2009/2417* (2013.01); *E06B 2009/2464* (2013.01)

(56) References Cited

U.S. PATENT DOCUMENTS

| | | | |
|---|---|---|---|
| 2014/0098282 A1* | 4/2014 | Yamada | .................. C09K 9/02 348/342 |
| 2015/0212382 A1* | 7/2015 | Miyazaki | .............. G02F 1/1503 348/294 |
| 2016/0020396 A1 | 1/2016 | Lee | |

* cited by examiner

ORGANIC COMPOUND, ELECTROCHROMIC ELEMENT CONTAINING THE SAME, OPTICAL FILTER, LENS UNIT, IMAGING DEVICE, AND WINDOW MATERIAL

CROSS-REFERENCE TO RELATED APPLICATIONS

This is a continuation application of U.S. patent application Ser. No. 15/498,339 filed on Apr. 26, 2017 which claims the benefit of Japanese Patent Application No. 2016-089721 filed Apr. 27, 2016 and Japanese Patent Application No. 2017-074833 filed Apr. 4, 2017, all of which are hereby incorporated by reference herein in their entirety.

BACKGROUND

Field of the Disclosure

The present disclosure relates to an organic compound having an electrochromic property, an electrochromic element containing the same, an optical filter, a lens unit, an imaging device, and a window material.

Description of the Related Art

As a material having an electrochromic (hereinafter, abbreviated as "EC" in some cases) property in which the optical absorption property (such as a coloration state and/or an optical transmittance) is changed by an electrochemical oxidation-reduction reaction, various materials have been reported.

As an organic low molecular weight compound having an EC property (organic low molecular weight EC compound), for example, a viologen derivative which is a cathodic EC compound to be colored by reduction and a phenazine derivative which is an anodic EC compound to be colored by oxidation may be mentioned.

Compared to an electrically conductive polymer, those low molecular weight EC compounds each have a short IC conjugation length and an absorption in an ultraviolet region, and by oxidation in the case of an anodic EC compound or by reduction in the case of a cathodic EC compound, the conjugation length of the above compound is increased as compared to that thereof obtained before oxidation or reduction is performed, so that the wavelength region at which light is absorbed is shifted to a visible light region. Hence, the organic low molecular weight EC compound is colored by oxidation or reduction.

In addition, heretofore, application of EC elements to automotive dimming mirrors, electronic paper, and the like has been proposed. Those EC elements are used because of their characteristics capable of displaying various color tones by selection of materials. When materials having various color tones are developed for those EC elements, the application thereof can be expected to be widely spread. For example, in consideration of the application to full color displays and the like, materials which are to be colored cyan, magenta, and yellow are required. Furthermore, in consideration of further broad application, EC materials having various absorption wavelengths in a colored state are required.

U.S. Pat. No. 6,020,987 (hereinafter, referred to as "Patent Literature 1") has disclosed a plurality of phenazine derivatives and viologen derivatives having different absorption wavelengths in a colored state and a plurality of phenazine derivatives having different maximum absorption wavelengths in a region of 460 to 532 nm in a colored state.

However, the phenazine derivative disclosed in Patent Literature 1 has no absorption peaks in a wavelength region of 540 nm or more in a colored state.

SUMMARY

Accordingly, the following embodiments are aimed to provide an organic compound having an absorption peak in a wavelength region of 540 nm or more in a colored state.

An organic compound according to one aspect of the present disclosure is represented by the following general formula (1).

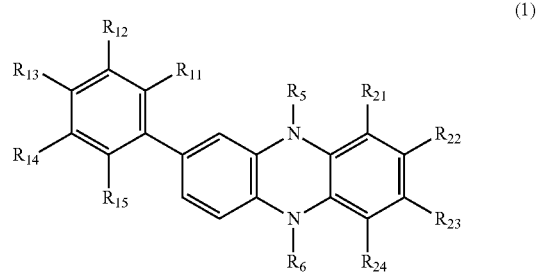

(1)

In the general formula (1), $R_{11}$ to $R_{15}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom. However, at least one of $R_{11}$, $R_{13}$, and $R_{15}$ represents the unsubstituted or the substituted alkoxy group or the unsubstituted or the substituted aryloxy group. In addition, $R_{11}$ to $R_{15}$ may form a ring structure by bonding therebetween.

$R_5$ and $R_6$ each independently represent an unsubstituted or a substituted alkyl group, an unsubstituted or a substituted aryl group, or an unsubstituted or a substituted aralkyl group.

In addition, $R_{21}$ to $R_{24}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom and may form a ring structure by bonding therebetween.

Further features of the present disclosure will become apparent from the following description of exemplary embodiments with reference to the attached drawings.

DESCRIPTION OF THE EMBODIMENTS

Figure 1:
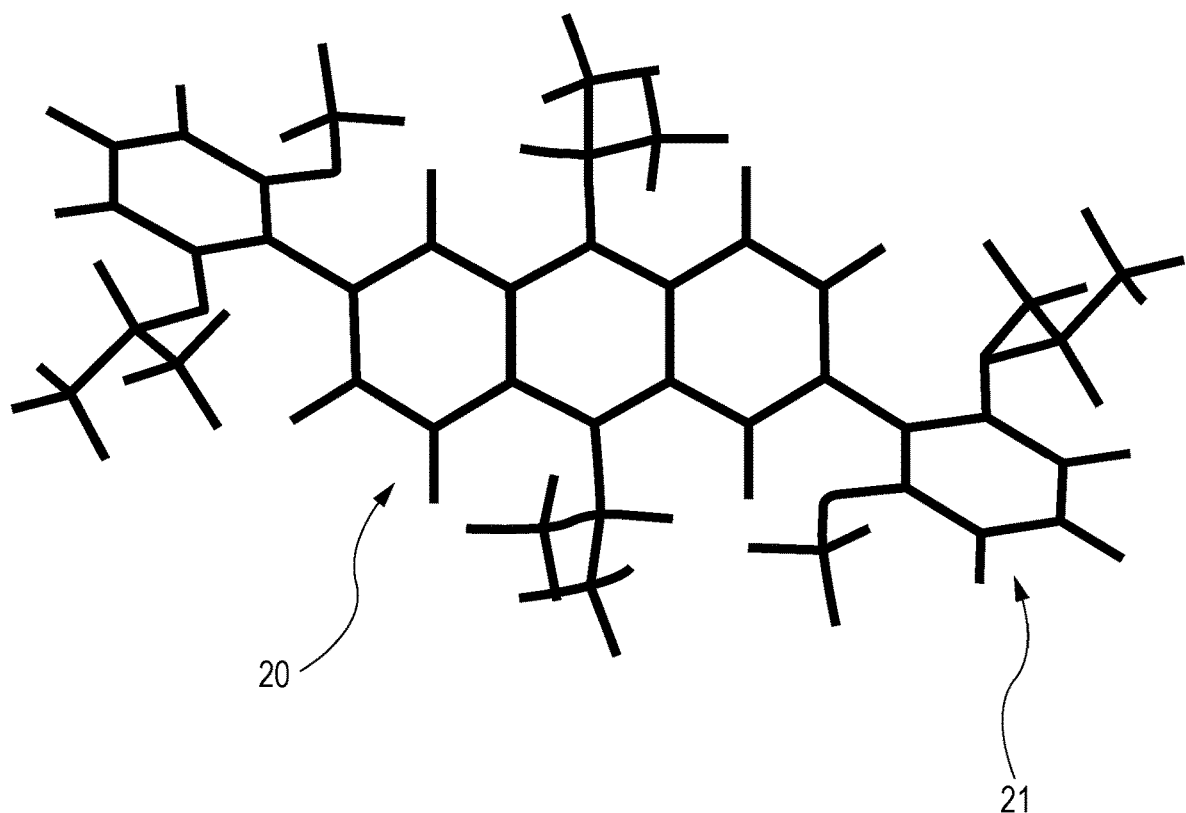
FIG. 1 shows a molecular model which is one example of an organic EC compound according to an embodiment of the subject application.

The organic compound according to this embodiment is an organic compound having an electrochromic (EC) property and represented by the following general formula (1).

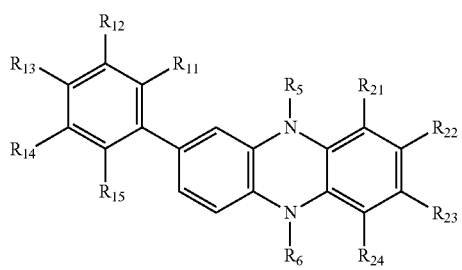

(1)

In the general formula (1), $R_{11}$ to $R_{15}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom. However, at least one of $R_{11}$, $R_{13}$, and $R_{15}$ represents the unsubstituted or the substituted alkoxy group or the unsubstituted or the substituted aryloxy group. In addition, $R_{11}$ to $R_{15}$ may form a ring structure by bonding therebetween.

$R_5$ and $R_6$ each independently represent an unsubstituted or a substituted alkyl group, an unsubstituted or a substituted aryl group, or an unsubstituted or a substituted aralkyl group.

In addition, $R_{21}$ to $R_{24}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom and may form a ring structure by bonding therebetween.

The organic compound represented by the above general formula (1) includes an organic compound represented by the following general formula (2). This compound is an organic compound in which in the compound represented by the general formula (1), $R_{11}$ represents an unsubstituted or a substituted alkoxy group or an unsubstituted or a substituted aryloxy group.

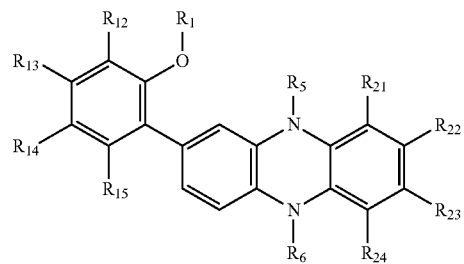

(2)

In the general formula (2), $R_1$ represents an unsubstituted or a substituted alkyl group, an unsubstituted or a substituted aryl group, or an unsubstituted or a substituted aralkyl group.

$R_{12}$ to $R_{15}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom and may form a ring structure by bonding therebetween.

$R_5$ and $R_6$ each independently represent an unsubstituted or a substituted alkyl group, an unsubstituted or a substituted aryl group, or an unsubstituted or a substituted aralkyl group.

In addition, $R_{21}$ to $R_{24}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom and may form a ring structure by bonding therebetween.

The organic compound represented by the above general formula (1) includes an organic compound having an EC property represented by the following general formula (3). This compound is an organic compound in which in the organic compound represented by the general formula (1), $R_{11}$ and $R_{15}$ each represent an unsubstituted or a substituted alkoxy group or an unsubstituted or a substituted aryloxy group.

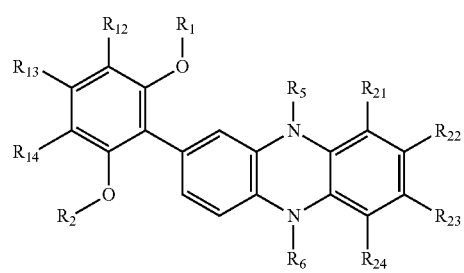

(3)

In the general formula (3), $R_1$ and $R_2$ each independently represent an unsubstituted or a substituted alkyl group, an unsubstituted or a substituted aryl group, or an unsubstituted or a substituted aralkyl group.

$R_{12}$ to $R_{14}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom and may form a ring structure by bonding therebetween.

$R_5$ and $R_6$ each independently represent an unsubstituted or a substituted alkyl group, an unsubstituted or a substituted aryl group, or an unsubstituted or a substituted aralkyl group.

In addition, $R_{21}$ to $R_{24}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom and may form a ring structure by bonding therebetween.

In addition, the organic compound represented by the above general formula (1) includes an organic compound having an EC property represented by the following general formula (4). This compound is an organic compound in which in the organic compound represented by the general formula (1), $R_{11}$ represents an unsubstituted or a substituted alkoxy group or an unsubstituted or a substituted aryloxy group, $R_{23}$ represents a substituted phenyl group, and this phenyl group is substituted by an alkoxy group or an aryloxy group at at least one of the ortho positions thereof.

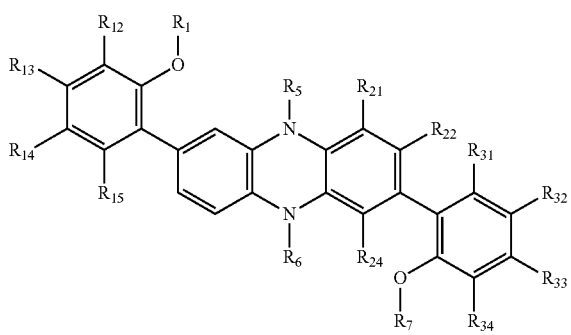

(4)

In the general formula (4), $R_1$ and $R_7$ each independently represent an unsubstituted or a substituted alkyl group, an unsubstituted or a substituted aryl group, or an unsubstituted or a substituted aralkyl group.

$R_{12}$ to $R_{15}$ and $R_{31}$ to $R_{34}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom and may form a ring structure by bonding therebetween.

$R_5$ and $R_6$ each independently represent an alkyl group having 1 to 20 carbon atoms, an unsubstituted or a substituted aryl group, or an unsubstituted or a substituted aralkyl group.

$R_{21}$, $R_{22}$, and $R_{24}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom and may form a ring structure by bonding therebetween.

Furthermore, the organic compound represented by the above general formula (1) includes an organic compound having an EC property represented by the following general formula (5). This organic compound is an organic compound in which in the organic compound represented by the general formula (1), $R_{11}$ and $R_{15}$ each represent an unsubstituted or a substituted alkoxy group or an unsubstituted or a substituted aryloxy group, $R_{23}$ represents a substituted phenyl group, and this phenyl group is substituted by an alkoxy group or an aryloxy group at each of the two ortho positions thereof.

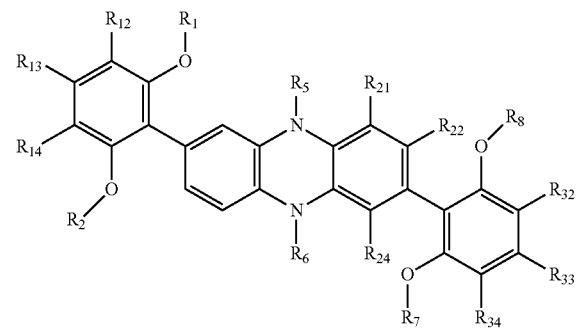

(5)

In the general formula (5), $R_1$, $R_2$, $R_7$, and $R_8$ each independently represent an unsubstituted or a substituted alkyl group, an unsubstituted or a substituted aryl group, or an unsubstituted or a substituted aralkyl group.

$R_{12}$ to $R_{14}$ and $R_{32}$ to $R_{34}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom and may form a ring structure by bonding therebetween.

$R_5$ and $R_6$ each independently represent an unsubstituted or a substituted alkyl group, an unsubstituted or a substituted aryl group, or an unsubstituted or a substituted aralkyl group.

$R_{21}$, $R_{22}$, and $R_{24}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom and may form a ring structure by bonding therebetween.

The organic compound represented by the above general formula (1) includes an organic compound having an EC property represented by the following general formula (6). This compound is an organic compound in which in the compound represented by the general formula (1), $R_{13}$, which is the substituent at the para position of the phenyl group, represents an unsubstituted or a substituted alkoxy group or an unsubstituted or a substituted aryloxy group.

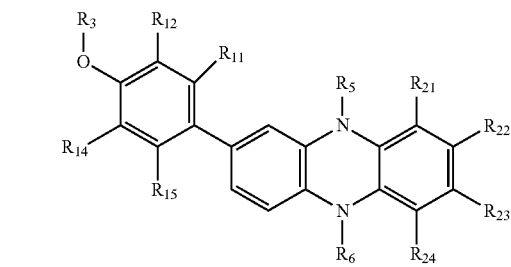

(6)

In the general formula (6), $R_3$ represents an unsubstituted or a substituted alkyl group, an unsubstituted or a substituted aryl group, or an unsubstituted or a substituted aralkyl group.

$R_{11}$, $R_{12}$, $R_{14}$, and $R_{15}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom and may form a ring structure by bonding therebetween.

$R_5$ and $R_6$ each independently represent an unsubstituted or a substituted alkyl group, an unsubstituted or a substituted aryl group, or an unsubstituted or a substituted aralkyl group.

$R_{21}$ to $R_{24}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom and may form a ring structure by bonding therebetween.

In the organic compound represented by the general formula (6), at least one of $R_{11}$ and $R_{15}$ preferably represents an unsubstituted or a substituted alkyl group, an unsubstituted or a substituted aryl group, or an unsubstituted or a substituted aralkyl group. In the compound as described above, by the steric hindrance of the substituents ($R_{11}$ and $R_{15}$) disposed at the ortho positions of the phenyl group, the phenazine ring and the phenyl group are twisted with each other. Hence, among the organic compounds represented by the general formula (6), a high transparency is obtained in a neutral state (decolored state).

In addition, the organic compound represented by the above general formula (1) includes an organic compound having an EC property represented by the following general formula (7). This compound is an organic compound in which in the organic compound represented by the general formula (1), the substituent represented by $R_{13}$ is an unsubstituted or a substituted alkoxy group or an unsubstituted or a substituted aryloxy group, and the substituent represented by $R_{23}$ is a phenyl group substituted by an alkoxy group or an aryloxy group at the para position thereof.

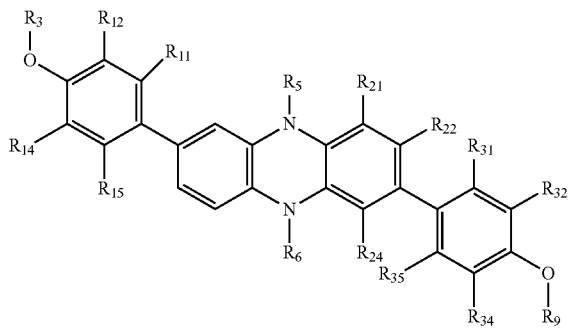

(7)

In the general formula (7), $R_3$ and $R_9$ each independently represent an unsubstituted or a substituted alkyl group, an unsubstituted or a substituted aryl group, or an unsubstituted or a substituted aralkyl group.

$R_{11}$, $R_{12}$, $R_{14}$, $R_{15}$, $R_{31}$, $R_{32}$, $R_{34}$, and $R_{35}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom and may form a ring structure by bonding therebetween.

$R_5$ and $R_6$ each independently represent an unsubstituted or a substituted alkyl group, an unsubstituted or a substituted aryl group, or an unsubstituted or a substituted aralkyl group.

$R_{21}$, $R_{22}$, and $R_{24}$ each independently represent a hydrogen atom, an unsubstituted or a substituted alkyl group, an unsubstituted or a substituted alkoxy group, an unsubstituted or a substituted aryl group, an unsubstituted or a substituted aryloxy group, an unsubstituted or a substituted aralkyl group, an acyl group, or a halogen atom and may form a ring structure by bonding therebetween.

In the organic compound represented by the general formula (7), at least one of $R_{11}$, $R_{15}$, $R_{31}$, and $R_{35}$ preferably represents an unsubstituted or a substituted alkyl group, an unsubstituted or a substituted aryl group, or an unsubstituted or a substituted aralkyl group. In the compound as described above, by the steric hindrance of the substituents ($R_{11}$, $R_{15}$, $R_{31}$, and $R_{35}$) disposed at the ortho positions of the phenyl groups, the phenazine ring and the phenyl groups are twisted with each other. Hence, among the organic compounds represented by the general formula (7), a high transparency is obtained in a neutral state (decolored state).

Concrete examples of the substituents of the general formulas (1) to (7) are shown below. However, the following organic compounds are merely shown as representative examples, and the present disclosure is not limited thereto.

The unsubstituted or the substituted alkyl group represented by one of $R_1$ to $R_3$ and $R_7$ to $R_9$ may have a linear, a branched, or a ring structure. In addition, a hydrogen atom may be substituted by a fluorine atom or an ester group. In addition, the unsubstituted or the substituted alkyl group represented by one of $R_1$ to $R_3$ and $R_7$ to $R_9$ preferably has 1 to 20 carbon atoms. As the alkyl group represented by one of $R_1$ to $R_3$ and $R_7$ to $R_9$, in particular, a methyl group, an ethyl group, a normal propyl group, an isopropyl group, a normal butyl group, a tertiary butyl group, an isobutyl group, a cyclohexyl group, a trifluoromethyl group, or the like may be mentioned. A methyl group, an isopropyl group, or an isobutyl group is preferable.

As the unsubstituted or the substituted aryl group represented by one of $R_1$ to $R_3$ and $R_7$ to $R_9$, for example, a phenyl group, a tolyl group, a biphenyl group, a fluorenyl group, a naphthyl group, a fluoranthenyl group, anthryl group, or a pyrenyl group may be mentioned. A phenyl group is preferable. The aryl group represented by one of $R_1$ to $R_3$ and $R_7$ to $R_9$ may have as the substituent, at least one of a halogen atom, an alkyl group having 1 to 4 carbon atoms, an alkoxy group having 1 to 4 carbon atoms, an aryl group, an aralkyl group, and an acyl group.

As the unsubstituted or the substituted aralkyl group represented by one of $R_1$ to $R_3$ and $R_7$ to $R_9$, for example, a benzyl group or a phenethyl group may be mentioned. The aralkyl group represented by one of $R_1$ to $R_3$ and $R_7$ to $R_9$ may have as the substituent, at least one of a halogen atom, an alkyl group having 1 to 4 carbon atoms, an alkoxy group having 1 to 4 carbon atoms, an aryl group, and an acyl group.

The unsubstituted or the substituted alkyl group represented by one of $R_{11}$ to $R_{15}$ and $R_{31}$ to $R_{35}$ may be a linear, a branched, or a ring structure. In addition, a hydrogen atom may be substituted by a fluorine atom or an ester group. In addition, the alkyl group represented by one of $R_{11}$ to $R_{15}$ and $R_{31}$ to $R_{35}$ preferably has 1 to 20 carbon atoms. As concrete examples of the alkyl group represented by one of $R_{11}$ to $R_{15}$ and $R_{31}$ to $R_{35}$, a methyl group, an ethyl group, a normal propyl group, an isopropyl group, a normal butyl group, a tertiary butyl group, a cyclohexyl group, a trifluoromethyl group, an isobutyl group, and the like may be mentioned.

As the unsubstituted or the substituted alkoxy group represented by one of $R_{11}$ to $R_{15}$ and $R_{31}$ to $R_{35}$, for example, a methoxy group, an ethoxy group, an isopropoxy group, a n-butoxy group, a tert-butoxy group, an ethylhexyloxy group, a 2-methoxyethoxy group, or a benzyloxy group may be mentioned. In addition, the alkoxy group represented by one of $R_{11}$ to $R_{15}$ and $R_{31}$ to $R_{35}$ preferably has 1 to 20 carbon atoms.

As the unsubstituted or the substituted aryl group represented by one of $R_{11}$ to $R_{15}$ and $R_{31}$ to $R_{35}$, for example, a phenyl group, a biphenyl group, a fluorenyl group, or a naphthyl group may be mentioned. In addition, the aryl group represented by one of $R_3$ and $R_9$ may have as the substituent, at least one of a halogen atom, an alkyl group having 1 to 4 carbon atoms, an alkoxy group having 1 to 4 carbon atoms, and an acyl group.

As the unsubstituted or the substituted aryloxy group represented by one of $R_{11}$ to $R_{15}$ and $R_{31}$ to $R_{35}$, for example, a phenoxy group or a naphthyloxy group may be mentioned. The aromatic ring of the unsubstituted or the substituted aryloxy group represented by one of $R_{11}$ to $R_{15}$ and $R_{31}$ to $R_{35}$ may have as the substituent, at least one of a halogen atom, an alkyl group having 1 to 4 carbon atoms, and an alkoxy group having 1 to 4 carbon atoms.

As the unsubstituted or the substituted aralkyl group represented by one of $R_{11}$ to $R_{15}$ and $R_{31}$ to $R_{35}$, for example, a benzyl group or a phenethyl group may be mentioned. The aralkyl group represented by one of $R_{11}$ to $R_{15}$ and $R_{31}$ to $R_{35}$ may have as the substituent, at least one of a halogen atom, an alkyl group having 1 to 4 carbon atoms, an alkoxy group having 1 to 4 carbon atoms, an aryl group, and an acyl group.

As the acyl group represented by one of $R_{11}$ to $R_{15}$ and $R_{31}$ to $R_{35}$, for example, an acetyl group or a benzoyl group may be mentioned.

Among $R_{11}$ to $R_{15}$ and $R_{31}$ to $R_{35}$, adjacent substituents may be bonded to each other to form a ring structure. As the ring structure formed in this case, for example, a benzene ring, a naphthalene ring, a fluorene ring, or a pyridine ring may be mentioned.

As the alkyl group represented by one of $R_5$ and $R_6$ may have a linear, a branched, or a ring structure. In addition, a hydrogen atom may be substituted by a fluorine atom or an ester group. As the alkyl group represented by one of $R_5$ and $R_6$, for example, a methyl group, an ethyl group, a normal propyl group, an isopropyl group, a normal butyl group, a tertiary butyl group, or an isobutyl group may be mentioned.

As the unsubstituted or the substituted aryl group represented by one of $R_5$ and $R_6$, for example, a phenyl group, a biphenyl group, a fluorenyl group, or a naphthyl group may be mentioned. The aryl group represented by one of $R_5$ and $R_6$ may have as the substituent, at least one of a halogen atom, an alkyl group having 1 to 4 carbon atoms, an alkoxy group having 1 to 4 carbon atoms, and an acyl group.

As the unsubstituted or the substituted aralkyl group represented by one of $R_5$ and $R_6$, for example, a benzyl group or a phenylethyl group may be mentioned. The aralkyl group represented by one of $R_5$ and $R_6$ may have as the substituent, at least one of a halogen atom, an alkyl group having 1 to 4 carbon atoms, an alkoxy group having 1 to 4 carbon atoms, an aryl group, and an acyl group.

As the unsubstituted or the substituted alkyl group represented by one of $R_{21}$ to $R_{24}$ may have a linear, a branched, or a ring structure. In addition, a hydrogen atom may be substituted by a fluorine atom or an ester group. The alkyl group represented by one of $R_{21}$ to $R_{24}$ preferably has 1 to 20 carbon atoms. As concrete examples of the alkyl group represented by one of $R_{21}$ to $R_{24}$, for example, a methyl group, an ethyl group, a normal propyl group, an isopropyl group, a normal butyl group, a tertiary butyl group, a cyclohexyl group, a trifluoromethyl group, and an isobutyl group may be mentioned.

As the unsubstituted or the substituted alkoxy group represented by one of $R_{21}$ to $R_{24}$, for example, a methoxy group, an ethoxy group, an isopropoxy group, a n-butoxy group, a tert-butoxy group, an ethylhexyloxy group, a 2-methoxyethoxy group, or a benzyloxy group may be mentioned. In addition, the alkoxy group represented by one of $R_{21}$ to $R_{24}$ preferably has 1 to 20 carbon atoms.

As the unsubstituted or the substituted aryl group represented by one of $R_{21}$ to $R_{24}$, for example, a phenyl group, a biphenyl group, a fluorenyl group, or a naphthyl group may be mentioned. The aryl group represented by one of $R_{21}$ to $R_{24}$ may have as the substituent, at least one of a halogen atom, an alkyl group having 1 to 4 carbon atoms, an alkoxy group having 1 to 4 carbon atoms, and an acyl group.

As the unsubstituted or the substituted aryloxy group represented by one of $R_{21}$ to $R_{24}$, for example, a phenoxy group or a naphthyloxy group may be mentioned. The aromatic ring of the unsubstituted or the substituted aryloxy group represented by one of $R_{21}$ to $R_{24}$ may have as the substituent, at least one of a halogen atom, an alkyl group having 1 to 4 carbon atoms, and an alkoxy group having 1 to 4 carbon atoms.

As the unsubstituted or the substituted aralkyl group represented by one of $R_{21}$ to $R_{24}$, for example, a benzyl group or a phenethyl group may be mentioned. The aralkyl group represented by one of $R_{21}$ to $R_{24}$ may have as the substituent, at least one of a halogen atom, an alkyl group having 1 to 4 carbon atoms, an alkoxy group having 1 to 4 carbon atoms, an aryl group, and an acyl group.

As the acyl group represented by one of $R_{21}$ to $R_{24}$, for example, an acetyl group or a benzoyl group may be mentioned.

Among $R_{21}$ to $R_{24}$, adjacent substituents may be bonded to each other to form a ring structure. As the ring structure formed in this case, for example, a benzene ring, a naphthalene ring, a fluorene ring, or a pyridine ring may be mentioned.

Next, characteristics based on the structure of a phenazine derivative which is an organic compound having an EC property and which is represented by the general formula (1) will be described. FIG. 1 shows a molecular model of an organic compound represented by the following formula (8) which is one example of the organic compound according to this embodiment.

(8)

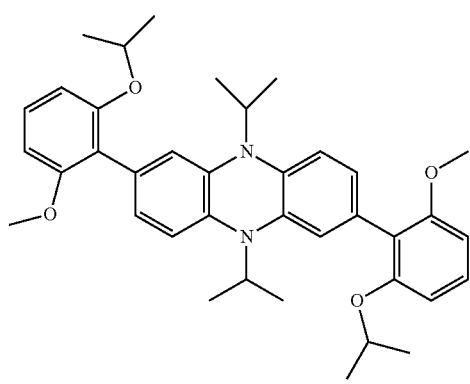

FIG. 1 shows the steric structure of a molecule in which in the general formula (5), one of $R_1$ and $R_2$ represents an isopropyl group, and the other represents a methyl group; and one of $R_7$ and $R_8$ represents an isopropyl group, and the other represents a methyl group. That is, in the organic compound represented by the chemical structural formula (8), an isopropoxy group is located at one of the ortho positions of each of the two phenyl groups bonded to the phenazine ring, and a methoxy group is located at the other ortho position of each of the phenyl groups. The organic compound represented by the chemical structural formula (8) corresponds to an example compound A-21 which will be described later. Hence, in the following description, the organic compound represented by the chemical structural formula (8) is called the "example compound A-21".

In addition, the steric structure shown in FIG. 1 was obtained by the structure optimization calculation of the ground state using Gaussian 09*Revision C.01 which was an electronic state calculation software. In this calculation, as the quantum chemistry calculation method, the density functional theory was used, and as the functional, LC-BLYP was used. As the basis function, in Gaussian 09, Revision C.01, 6-31+G** was used.

Gaussian 09, Revision C.01,
M. J. Frisch, G. W. Trucks, H B. Schlegel, G E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford Conn., 2010.

In FIG. 1, the example compound A-21 has a phenazine ring 20 and phenyl groups 21 each bonded thereto and has an isopropyl group and a methoxy group on the ortho positions of each of the phenyl groups 21.

When the phenazine ring 20 having an electrochromic property is assumed to have a flat plane, the plane of the phenyl group 21 having alkoxy groups at the ortho positions thereof is intersected with the plane of the phenazine ring 20, and the angle formed between the plane of the phenazine ring 20 and the plane of the phenyl group 21 is large. In phenazine derivatives, the resonance of a molecular structure in which the plane of the phenazine ring 20 and the plane of the phenyl group 21 form an angle of approximately 90° is reduced since the orbit of π electrons of the phenazine ring and the orbit of π electrons of the phenyl group are orthogonal to each other. Hence, the HOMO (highest occupied molecular orbital) is localized on the phenazine ring 20, and as a result, the absorption in a neutral state can be shifted to a short wavelength side.

Hereinafter, the difference between the organic compound of this embodiment and a known phenazine derivative will be described. In Patent Literature 1, compounds Ref-1 and Ref-2 represented by the following chemical structural formulas have been disclosed.

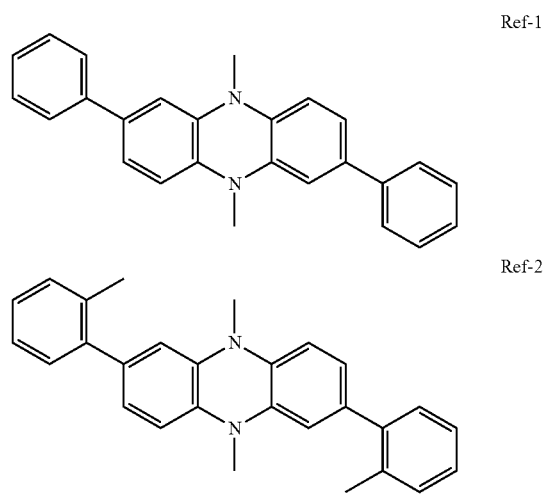

In the known compound Ref-1, no substituents are present at the ortho positions of each of the phenyl groups bonded to the phenazine ring. Hence, the planarity of the molecule is high, and since an electronic resonance structure is spread over the entire molecule, so that the absorption in a neutral state is shifted to a long wavelength side. According to the result of a confirmation test actually performed by the present inventors, the absorption edge of the compound Ref-1 in a neutral state extends to approximately 460 nm in a visible wavelength region, and a pale reddish-brown color is observed in a solid state and a solution state.

In addition, Patent Literature 1 has disclosed that, when an alkyl group, such as a methyl group, is introduced at the ortho position of each of the phenyl groups bonded to the phenazine ring as shown in the compound Ref-2 by way of example, the degree of coloration in a neutral state is decreased. The reason for this is believed that by the steric hindrance caused by an alkyl group, such as a methyl group, since the phenazine ring and the phenyl group are twisted with each other, the neutral absorption is shifted to a short wavelength side.

However, according to Patent Literature 1, although the wavelength (absorption wavelength) of the absorption peak in a colored state of the compound Ref-1 is 532 nm, the absorption wavelength of the compound Ref-2 is 512 nm and is shifted to a short wavelength side as compared to that of the compound Ref-1. This phenomenon indicates that the above twist of the molecule in a neutral state remains in a molecular structure of a radical cation in a colored state, and as a result, the absorption in an oxidized state is also shifted to a short wavelength side.

That is, in a related phenazine derivative, the improvement in transparency (absorption shift to a short wavelength side) in a neutral state and a long-wavelength absorption in an oxidized colored state cannot be simultaneously obtained.

On the other hand, according to the organic compound of this embodiment, by the twist between the phenazine ring 20 and the phenyl group 21, the absorption is shifted to a short wavelength side in a neutral state, and a high transparency can be obtained, and in addition, in an oxidized state (colored state), the absorption peak is located in a wavelength region of 540 nm or more which is a long wavelength side than that of the compound Ref-1. The phenomenon described above is caused by the presence of the alkoxy group as the substituent and is obtained by a unique effect of an alkoxy group or an aryloxy group which cannot be expected based on the known findings.

In addition, in the absorption spectrum described in this specification, the absorption peak is defined such that the optical absorption amount is maximized in a certain wavelength region, and the half width is 20 nm or more. In this embodiment, the half width indicates the width of the wavelength at which the absorbance in the absorption spectrum is a half (half value) of that at the maximum value.

The organic compound according to this embodiment may have at least one absorption peak in a wavelength region of 540 nm or more in an oxidized state (colored state). In addition, the organic compound according to this embodiment may have a plurality of absorption peaks in a wavelength region of 540 nm or more in an oxidized state (colored state) or may also have absorption peaks in a wavelength region of 540 nm or more and in a wavelength region of less than 540 nm.

This unique effect of an alkoxy group or an aryloxy group will be described. By the quantum chemical calculation described above, the molecular structure of the example compound A-21 and that of the known compound Ref-2 are each estimated in a neutral state and an oxidized (radical cation) state. The dihedral angle, that is, the angle between the two planes of the phenazine ring and the phenyl group, is shown in Table 1.

TABLE 1

|  | Neutral State | Oxidized State |
| --- | --- | --- |
| Example Compound A-21 | 60.6° | 45.0° |
| Compound Ref-2 | 60.9° | 49.3° |

Although the dihedral angle of the example compound A-21 in an oxidized state was 45.0°, the dihedral angle of the compound Ref-2 was 49.3°. In addition, as the bond order indicating the electron density of the bond between the phenazine ring 20 and the phenyl group 21, the example compound A-21 had 0.9828, and the compound Ref-2 had 0.4870.

Those results indicate that although the example compound A-21 and the compound Ref-2 have approximately the same dihedral angle in a neutral state, in a radical cation state which is an oxidized state, the planarity of the example compound A-21 is higher than that of the compound Ref-2. That is, those results indicate that the mixing of the orbits of the phenazine ring and the phenyl group of the example compound A-21 is promoted in an oxidized state as compared to that of the compound Ref-2. As a result, in the example compound A-21, the absorption peak in an oxidized state is more shifted to a long wavelength side.

This phenomenon could not be obtained by a methyl substituent provided on the phenyl group of the compound Ref-2 and is obtained by a unique effect of the organic compound represented by the general formula (1) in which the phenyl group has as the substituent, an alkoxy group or an aryloxy group. That is, in the organic compound of this embodiment, when the dihedral angle in an oxidized state is decreased as compared to that in a neutral state, as shown below, hydrogen bonding occurs between a hydrogen atom of the phenazine ring and an oxygen atom of the alkoxy group functioning as the substituent of the phenyl group. Hence, a stable six-membered ring is likely to be formed. As a result, the dihedral angle between the phenazine ring and the phenyl group in an oxidized state is decreased, and the planarity is increased, so that the mixing of the orbits is promoted as compared to that in the past.

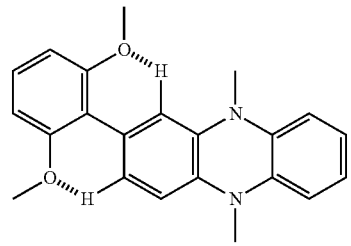

On the other hand, since the alkyl substituent, such as that of the compound Ref-2, is a weak electron-donating group and contains no oxygen atom, the dihedral angle in an oxidized state is relatively large, and the absorption peak is not shifted to a long wavelength side.

As described above, in the organic compound according to this embodiment, by the contribution of a strong electron-donating property of the alkoxy group and an electronic interaction between the lone pair of the oxygen atom of the alkoxy group and the hydrogen atom of the phenazine ring, the twist is generated in a decolored state, and in a colored state, the planarity is improved.

Hence, in a decolored state of the organic compound according to this embodiment, since the absorption is shifted to a short wavelength side by the twist between the phenazine ring and the phenyl group, a high transparency is obtained. In addition, in a colored state of the organic compound according to this embodiment, the mixing of the orbits of the phenazine ring and the phenyl group is promoted by a unique electronic effect of the alkoxy group, and as a result, the absorption is shifted to a long wavelength side. That is, according to the organic compound of this embodiment, an organic compound having an absorption peak in a long wavelength region of 540 nm or more in a colored state and a high transparency in a decolored state as compared to that in the past can be provided.

The EC characteristics of a different organic compound represented by the general formula (1) will be described. An organic compound represented by the following chemical structural formula (9) is one example of the organic compound according to this embodiment represented by the general formula (1). In addition, since the organic compound represented by the chemical structural formula (9) corresponds to an example compound C-6 which will be described later, in the following description, this organic compound is called the example compound C-6.

C-6

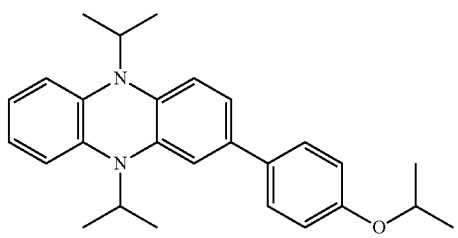

(9)

The example compound C-6 represented by the chemical structural formula (9) is a compound in which in the general formula (1), $R_{13}$ represents an alkoxy group, and $R_3$ of the alkoxy group represents an isopropyl group. That is, the example compound C-6 has a phenazine ring and a phenyl group bonded thereto and also has an isopropoxy group at the para position of the phenyl group.

Hereinafter, the difference between the example compound C-6 and a known phenazine derivative will be described. In Patent Literature 1, a compound Ref-3 represented by the following chemical structural formula has been disclosed.

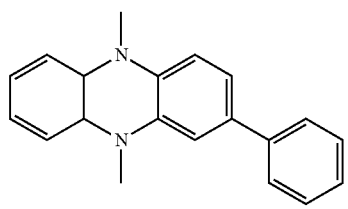

Ref-3

The known compound Ref-3 has no alkyl group at the para position of the phenyl group bonded to the phenazine ring. According to Patent Literature 1, the wavelength (absorption wavelength) of the absorption peak of the compound Ref-3 in a colored state is 496 nm.

On the other hand, the example compound C-6 has in an oxidized state (colored state), an absorption peak in a wavelength region of 540 nm or more, which is longer than that of the compound Ref-3. The reason for this is that the alkoxy group is located at the para position of the phenyl group as the substituent.

The example compound C-6 has at least one absorption peak in a wavelength region of 540 nm or more in an oxidized state (colored state). In addition, the organic compound according to this embodiment may also have in an oxidized state (colored state), a plurality of absorption peaks in a wavelength region of 540 nm or more or absorption peaks in a wavelength region of 540 nm or more and a wavelength region of less than 540 nm.

The example compound C-6 has a strong electron donating alkoxy group at the para position of the phenyl group. By the influence of this strong electron donating group, the electron density of the phenazine ring having an EC property is increased, the highest occupied molecular orbital (HOMO) energy level becomes shallow, and the energy gap of HOMO-LUMO is decreased. When this energy gap is decreased, the absorption is shifted to a long wavelength side.

In addition, by the contribution of the electronic interaction between the lone pair of the oxygen atom of the alkoxy group and the π electron conjugated system on the phenazine ring and the phenyl ring, the mixing of the orbits of the phenazine ring and the phenyl group in the molecular structure of a radical cation in an oxidized state is promoted, and as a result, the absorption thereof is shifted to a long wavelength side. It is believed that the shift of the absorption to a long wavelength side as described above is also generated by the contribution of the electronic interaction between the lone pair of the oxygen atom of the alkoxy group or the aryloxy group and the π electron conjugated system on the phenazine ring and the phenyl ring.

As described above, in the organic compound according to this embodiment, by the unique electronic effect of the alkoxy group or the aryloxy group, the absorption is shifted to a long wavelength side in an oxidized state as compared to that of the known compound Ref-3. That is, the organic compound according to this embodiment has an absorption peak in a long wavelength region of 540 nm or more in a colored state.

As for the neutral absorption in a decolored state, in the known compound Ref-3 and the example compound C-6, since the molecular planarity is also high in a neutral state, and the electronic resonance structure is spread over the entire molecule, the neutral absorption is also shifted to a long wavelength side. The absorption edge of the compound Ref-3 in a neutral state actually extends to approximately 450 nm, and the absorption edge of the example compound C-6 in a neutral state extends to a visible wavelength region of 445 nm.

Furthermore, as one example of the phenazine derivative, which is the organic compound having an EC property represented by the general formula (1) according to this embodiment, an organic compound represented by the following chemical structural formula (10) will be described. Since corresponding to an example compound D-2 which will be described later, this compound is called the example compound D-2.

D-2

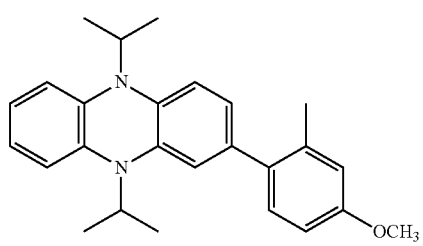

(10)

The example compound D-2 represented by the chemical structural formula (10) is a compound in which in the general formula (1), $R_{13}$ represents a methoxy group, and $R_{11}$ represents a methyl group. That is, the example compound D-2 has a phenazine ring and a phenyl group bonded thereto, and also has a methoxy group at the para position and a methyl group at the ortho group of the phenyl group bonded to the phenazine ring.

In the example compound D-2, since the methyl group is introduced at the ortho position of the phenyl group bonded to the phenazine ring, by the steric hindrance of the methyl group, the phenazine ring and the phenyl group are twisted with each other. That is, because of the molecular structure having a large angle formed between the plane of the phenazine ring and the plane of the phenyl group, the orbit of the π electrons of the phenazine ring and that of the phenyl group are orthogonal to each other, and as a result, the resonance therebetween is reduced. Hence, the HOMO is localized on the phenazine ring, so that the absorption in a neutral state can be shifted to a short wavelength side.

As for the improvement in transparency using the twist of the molecule as described above, a similar tendency thereto has also been disclosed, for example, in Patent Literature 1. However, in a related phenazine derivative, the improvement in transparency (the shift of absorption to a short wavelength side) in a neutral state and the long-wavelength absorption in an oxidized colored state cannot be simultaneously satisfied. The reason for this is that the twist of the molecule in a neutral state described above remains in the molecular structure of a radical cation in a colored state, and as a result, the absorption in an oxidized state is also shifted to a short wavelength side.

However, in the example compound D-2 represented by the chemical structural formula (10) according to the present disclosure, since the absorption edge in a neutral state is located at 410 nm, the neutral transparency is significantly improved, and the absorption wavelength peak in a colored state is located at 553 nm which is in a long wavelength region of 540 nm or more. That is, in the organic compound according to this embodiment, the twist is generated in a neutral state, and by the contribution of the strong electron donating property of the alkoxy group and the electronic interaction between the lone pair of the oxygen atom of the alkoxy group and the hydrogen atom of the phenyl ring, in an oxidized state, the planarity is improved. It is believed that besides the case in which $R_{13}$ represents an alkoxy group, an advantage similar to that described above can also be obtained even when an aryloxy group is used instead of using an alkoxy group.

In the organic compound according to this embodiment, by the contribution of the strong electron donating property of the alkoxy group or the aryloxy group and the electronic interaction between the lone pair of the oxygen atom of the alkoxy group or the aryloxy group and the hydrogen atom of the phenyl ring, in a neutral state, the twist is generated, and in an oxidized state, the planarity is improved.

Hence, in the organic compound according to this embodiment, by the twist between the phenazine ring and the phenyl group in a neutral state, the absorption is shifted to a short wavelength side, so that a high transparency is obtained. In particular, as described above, in the organic compound according to this embodiment, since the angle formed between the plane of the phenazine ring and the plane of the phenyl group is large, the absorption in a decolored state is shifted to a short wavelength side, and the transparency is improved as compared to that in the past.

In addition, in the organic compound according to this embodiment, by the unique electronic effect of the alkoxy group or the aryloxy group in an oxidized state, the mixing of the orbits of the phenazine ring and the phenyl group is promoted, and the absorption thereof is shifted to a long wavelength side. That is, in the organic compound according to this embodiment, an organic compound having an absorption peak in a long wavelength region of 540 nm or more in a colored state can be provided. In addition, an organic compound having a high transparency in a decolored state as compared to that in the past can be provided.

In addition, the organic compound according to this embodiment more preferably has no absorption edge in a wavelength region of 430 nm or more so as to be transparent even in a wavelength region of 430 nm or more.

Hereinafter, concrete structural formulas of the organic compound according to this embodiment will be shown by way of example. However, the organic compound according to this embodiment is not limited thereto.

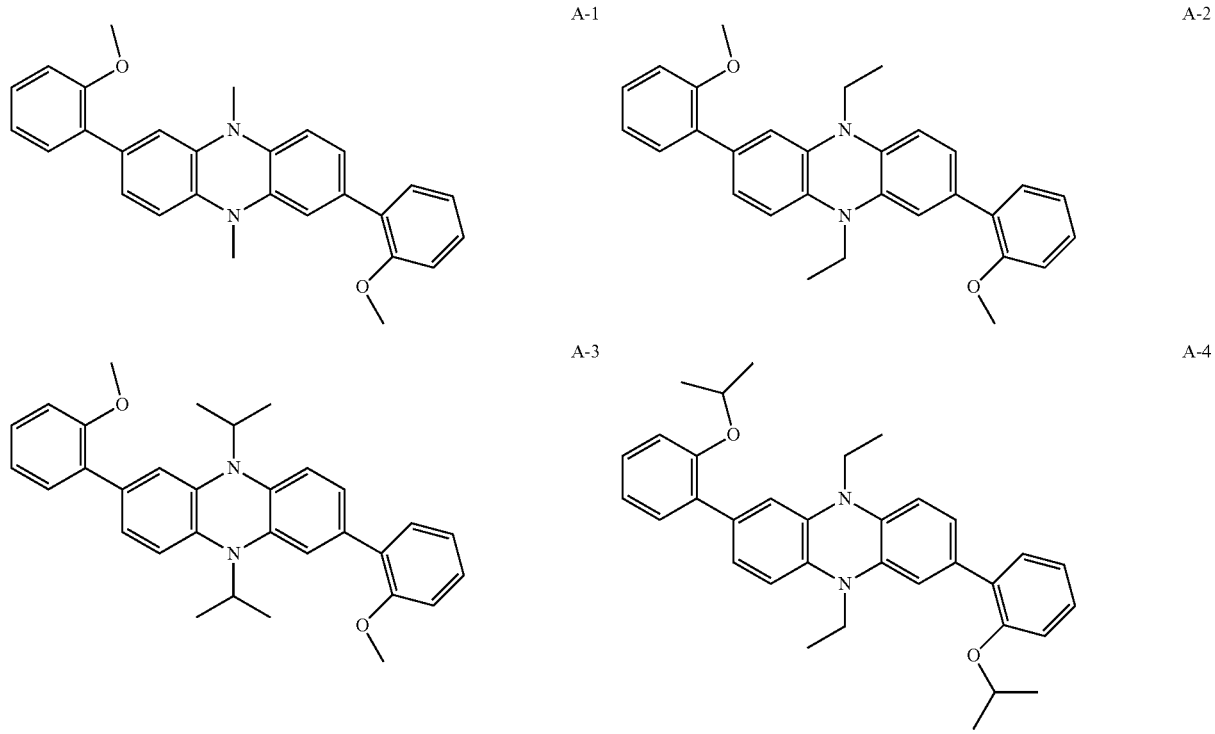

-continued
A-5
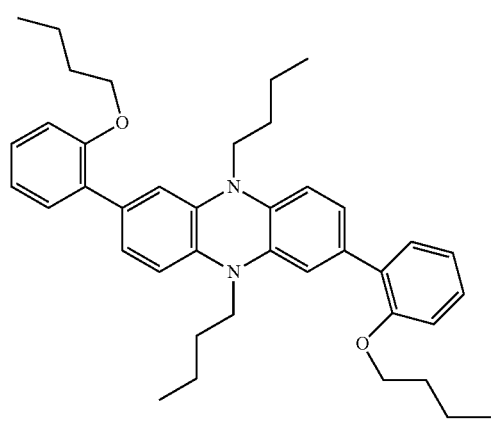
A-6
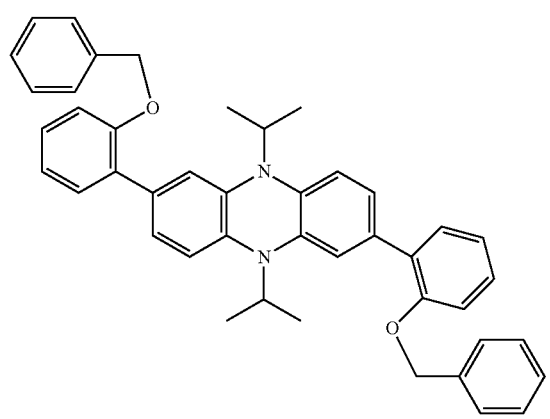
A-7
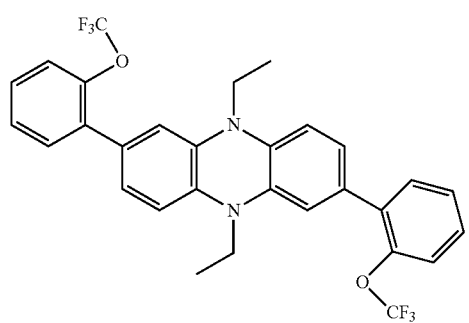
A-8
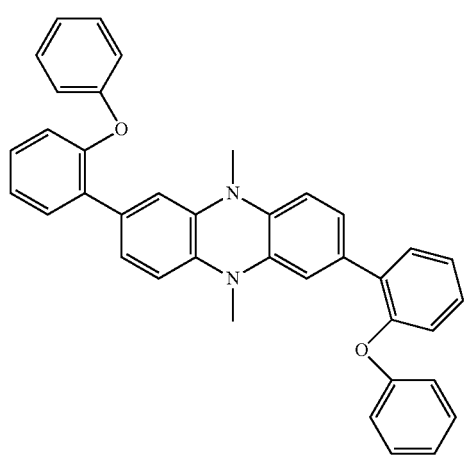
A-9
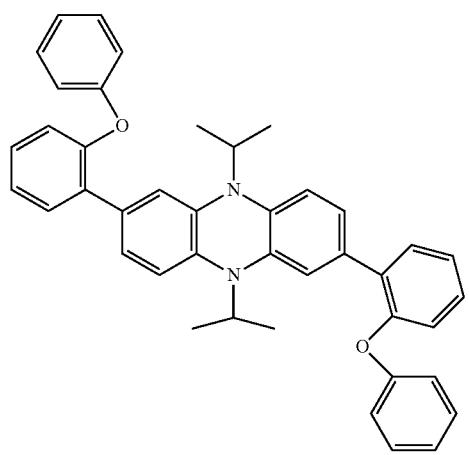
A-10
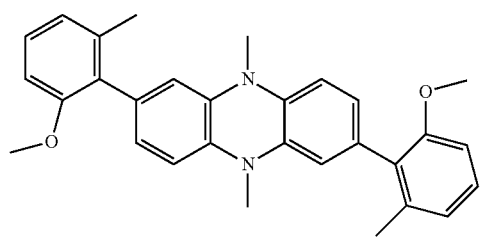
A-11
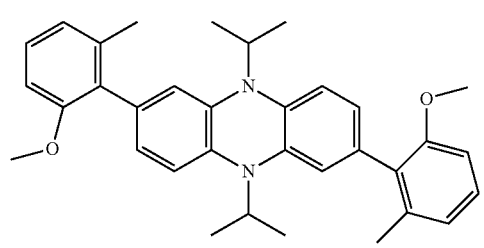
A-12
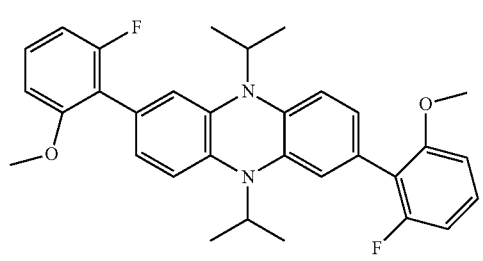

-continued
A-13
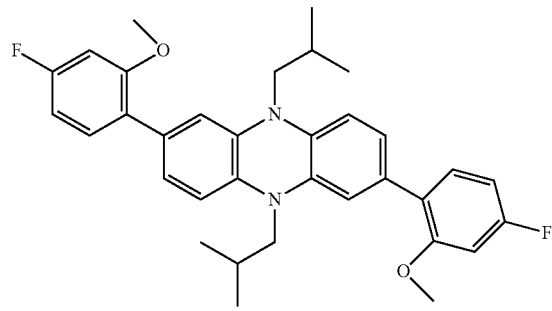
A-14
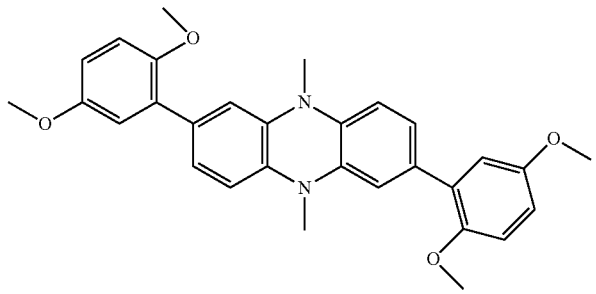
A-15
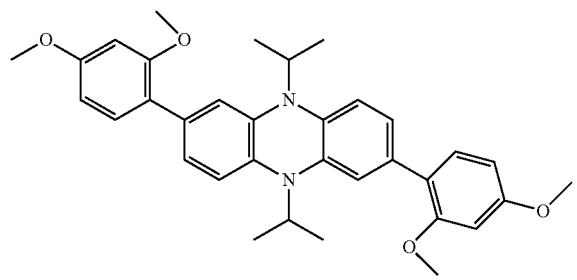
A-16
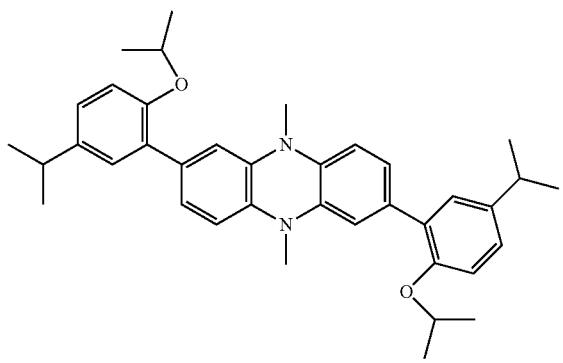
A-17
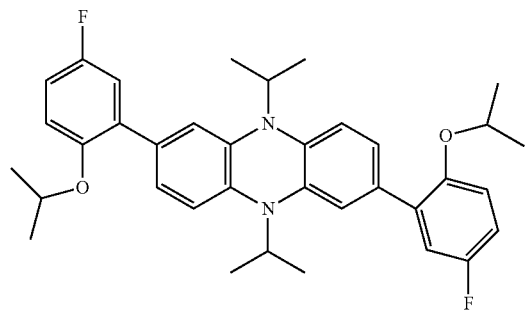
A-18
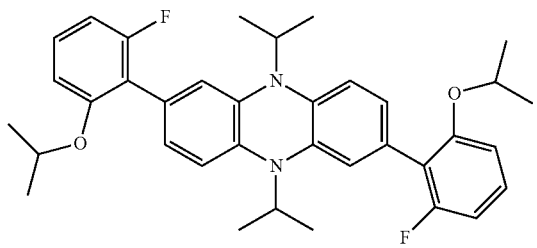
A-19
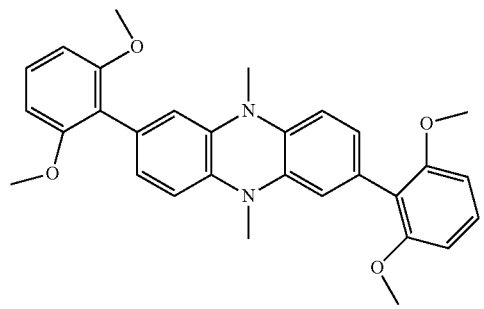
A-20
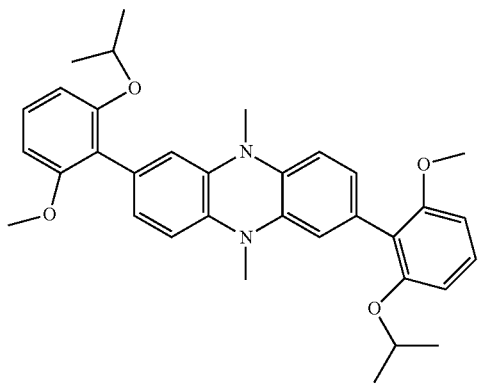

-continued
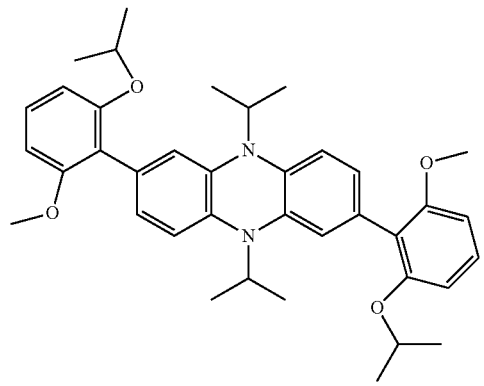
A-21
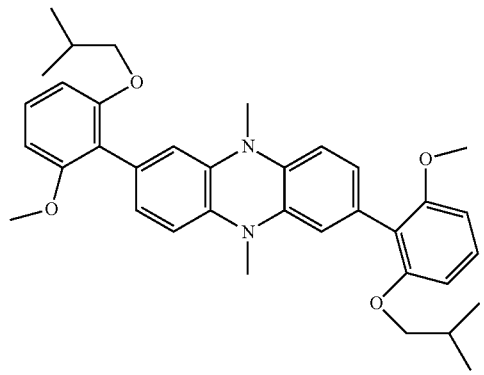
A-22
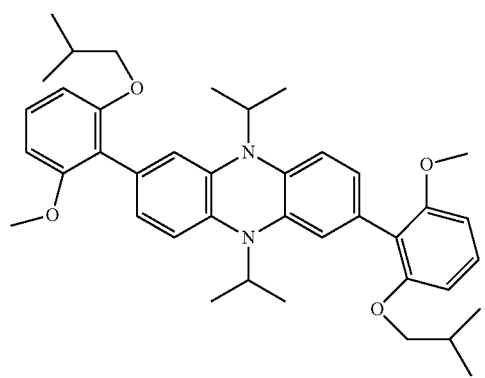
A-23
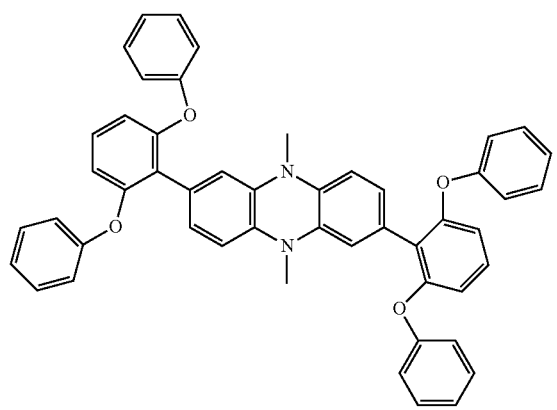
A-24
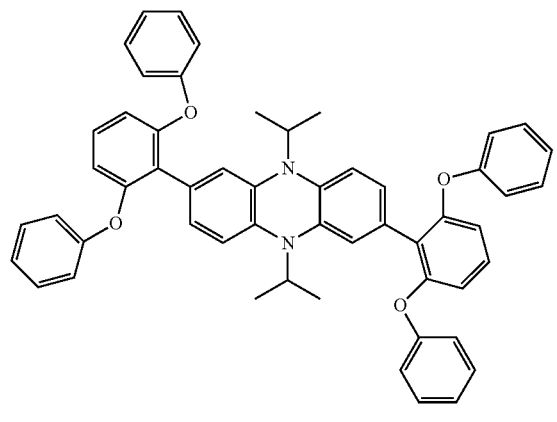
A-25
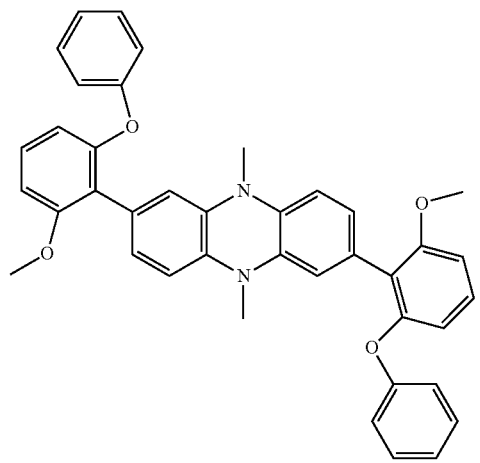
A-26

-continued
A-27
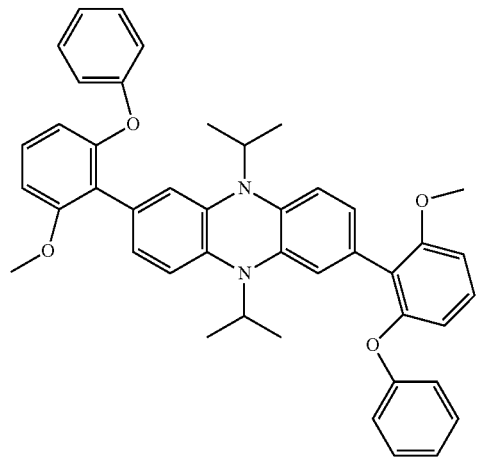
A-28
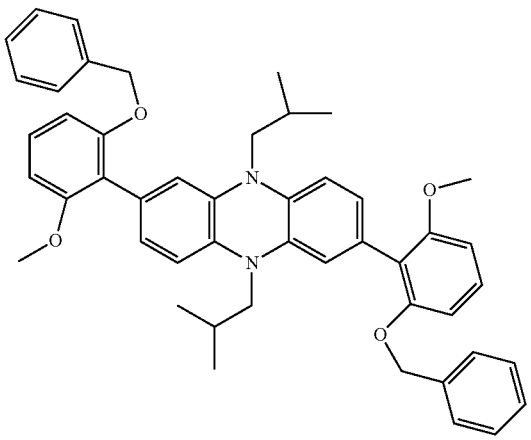
A-29
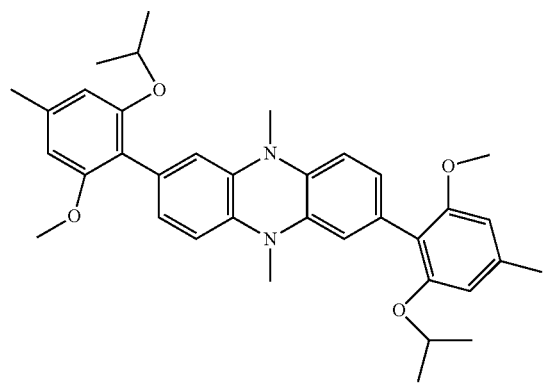
A-30
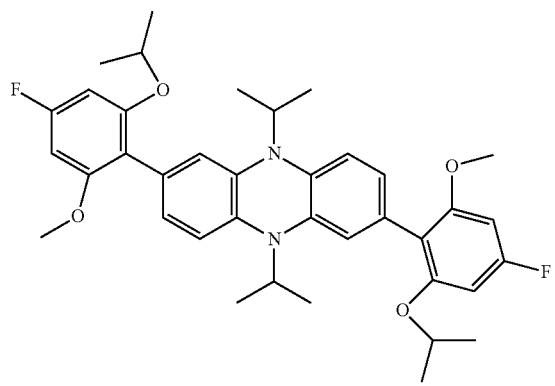
A-31
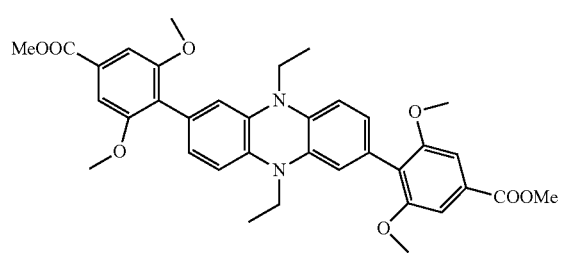
A-33
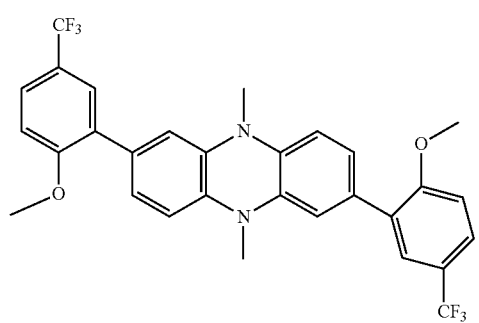
A-33
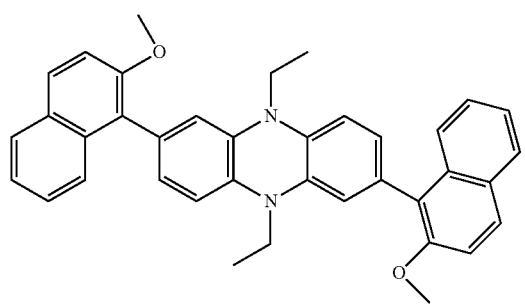
A-34
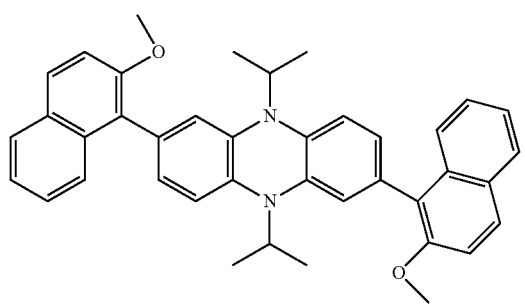

-continued
A-35
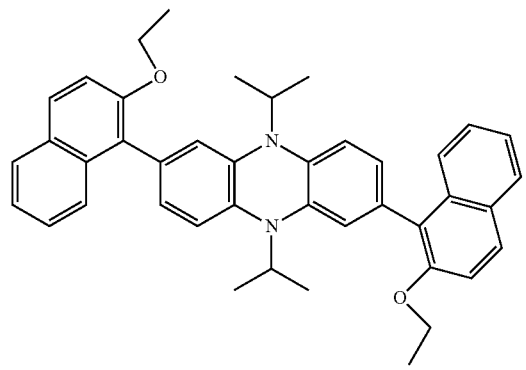
A-36
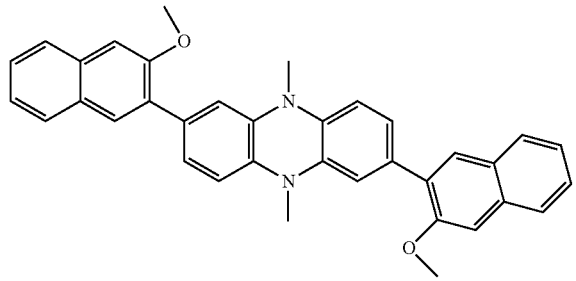
A-37
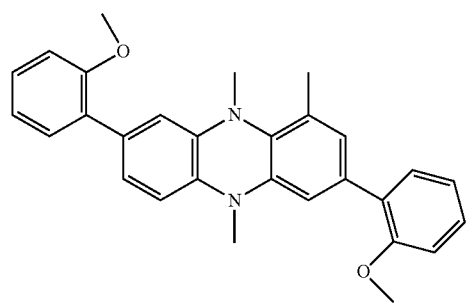
A-38
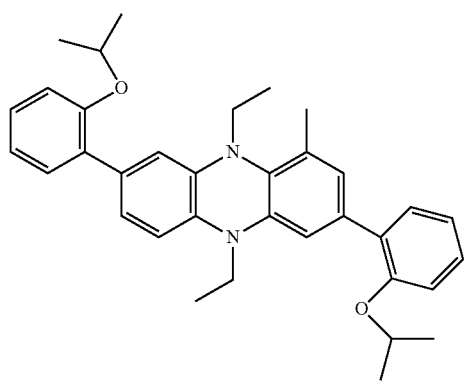
A-39
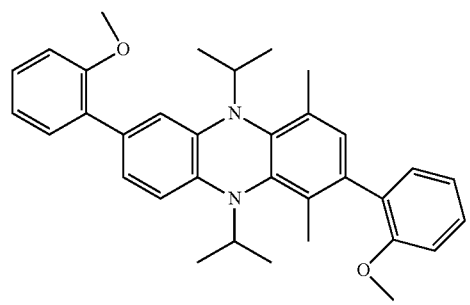
A-40
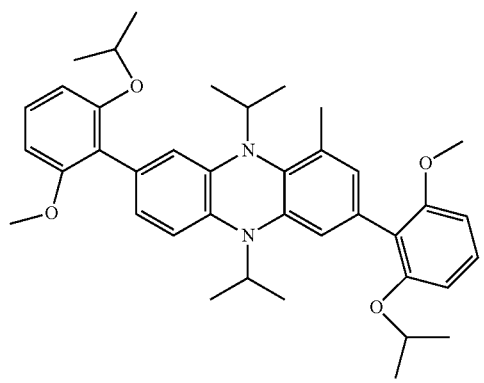
A-41
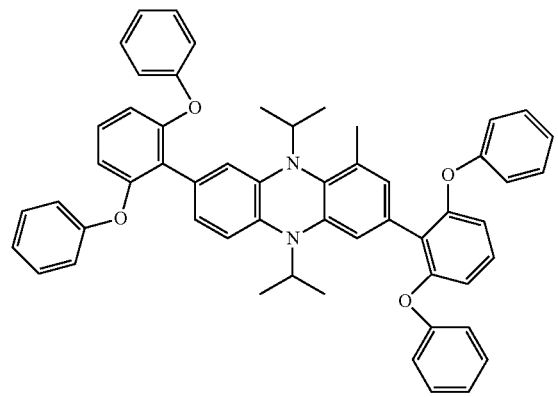
A-42
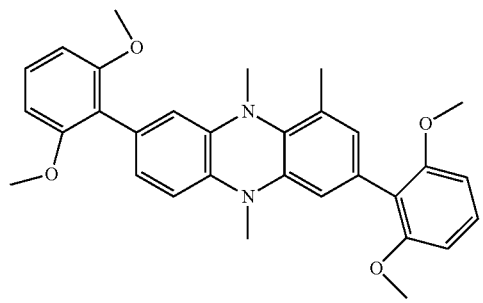

-continued
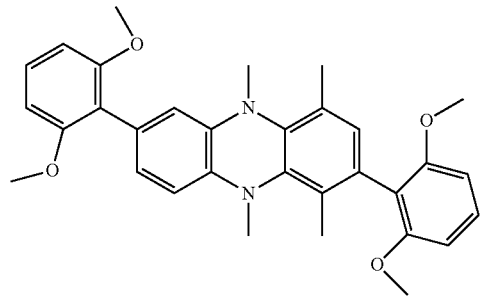
A-43
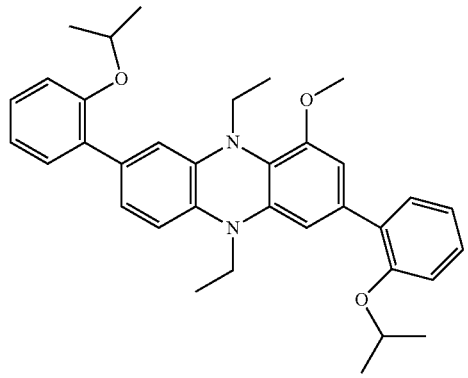
A-44
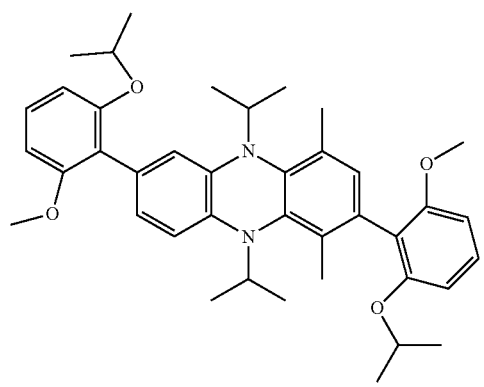
A-45
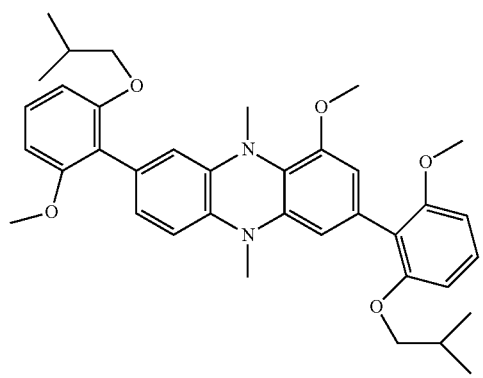
A-46
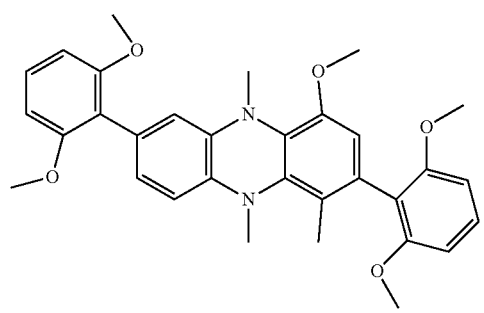
A-47
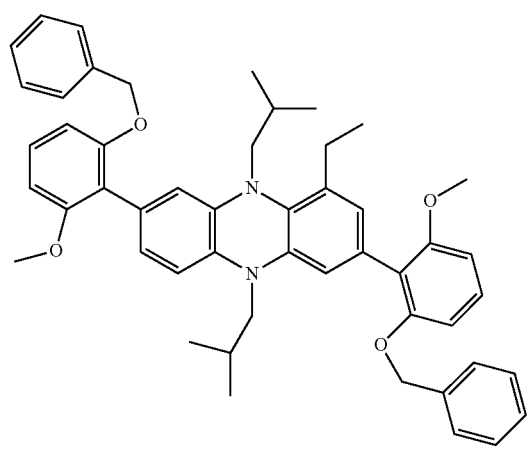
A-48
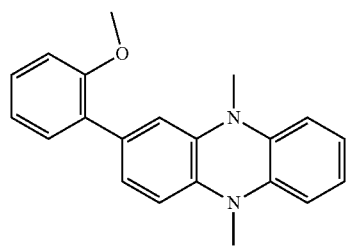
B-1
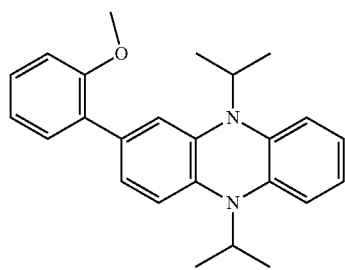
B-2

-continued
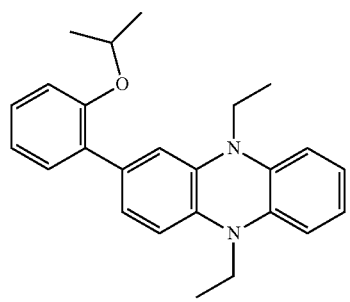
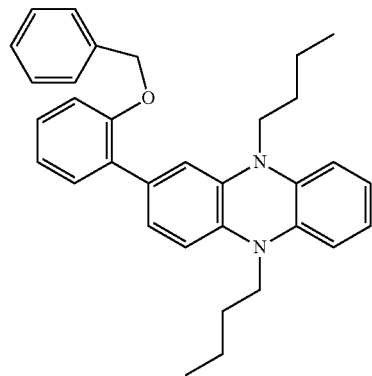
B-3
B-4
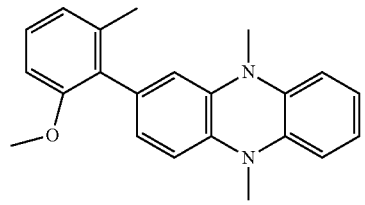
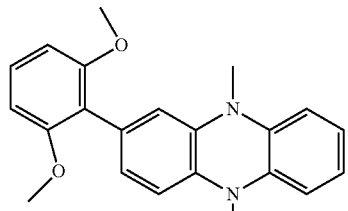
B-5
B-6
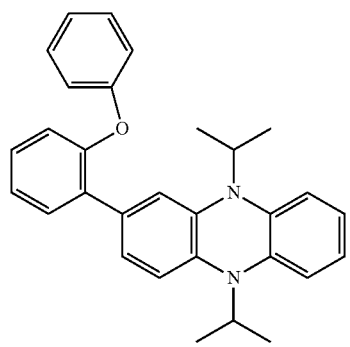
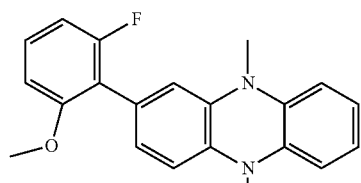
B-7
B-8
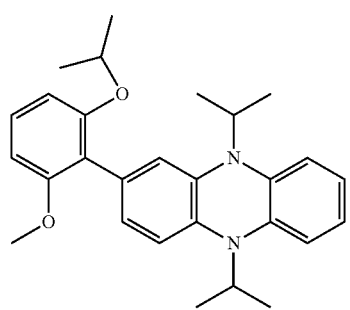
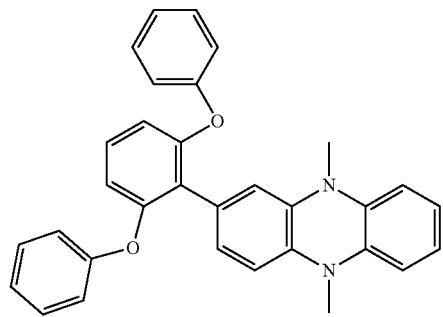
B-9
B-10
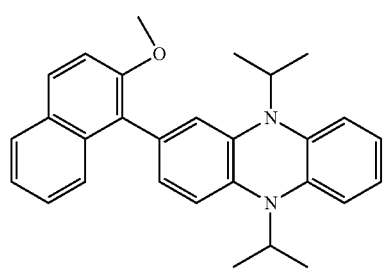
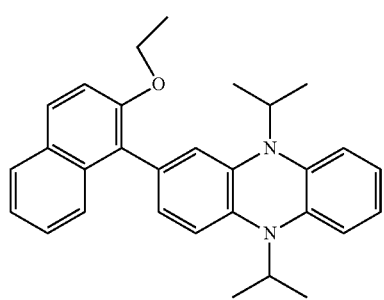
B-11
B-12

-continued
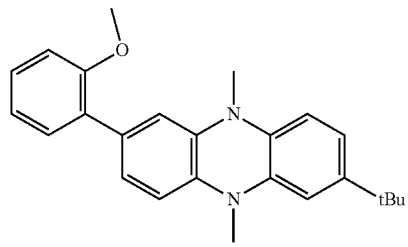
B-13
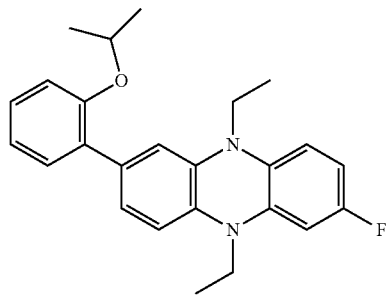
B-14
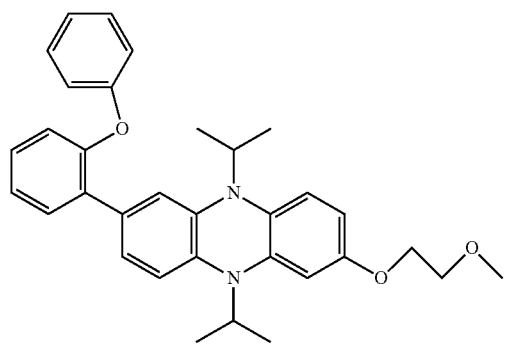
B-15
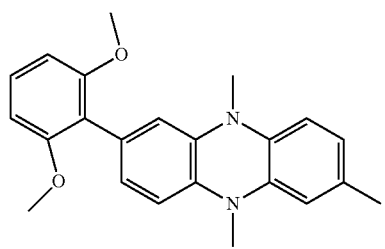
B-16
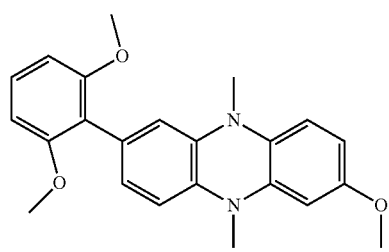
B-17
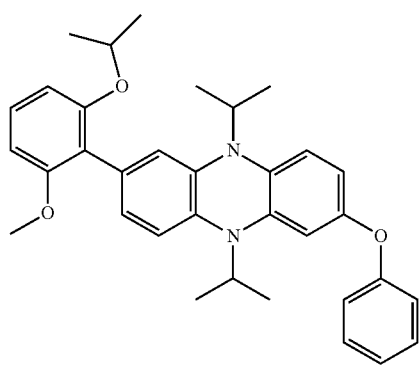
B-18
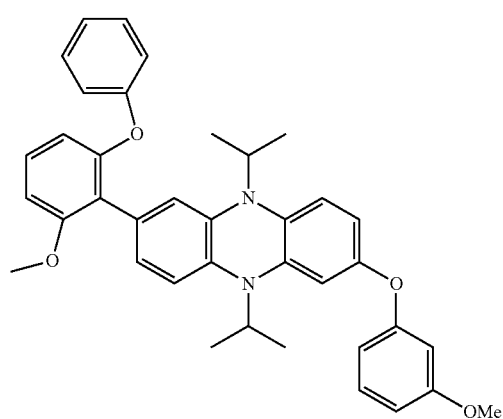
B-19
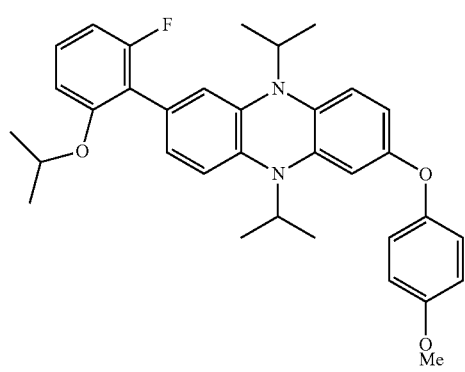
B-20

-continued
B-21
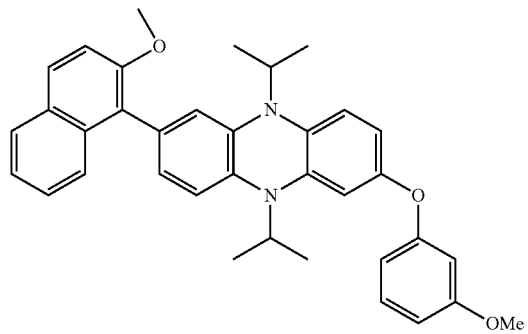
B-22
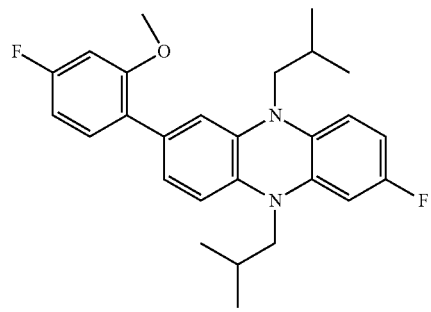
B-23
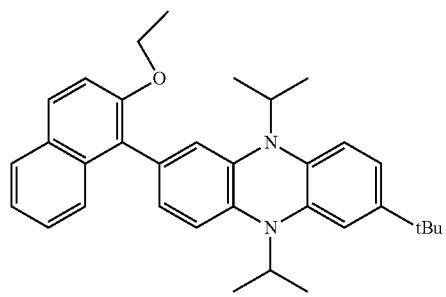
B-24
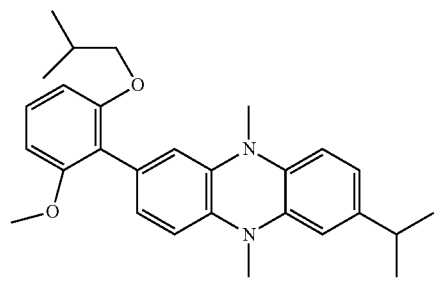
B-25
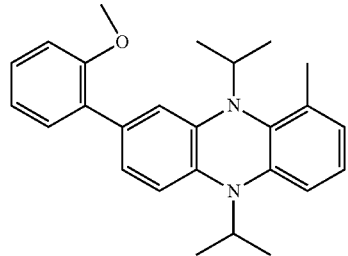
B-26
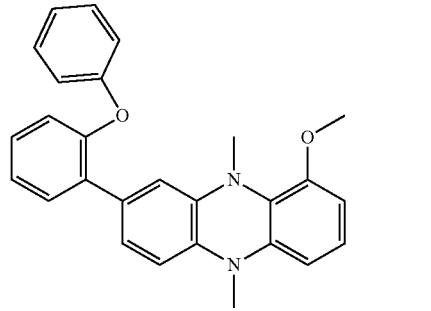
B-27
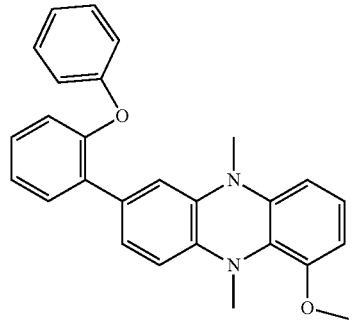
B-28
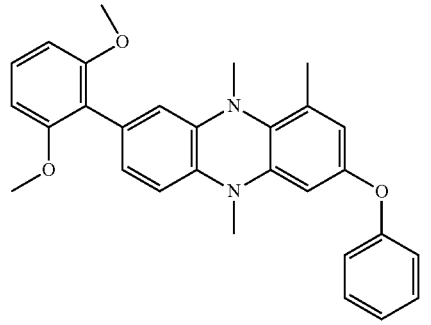
B-29
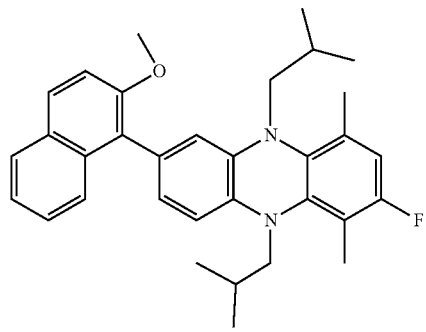
B-30
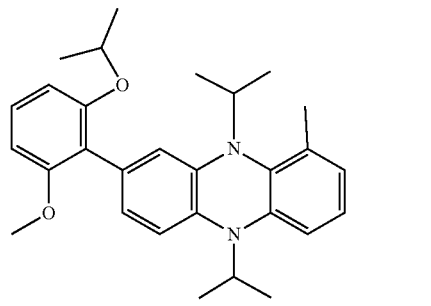

-continued
B-31
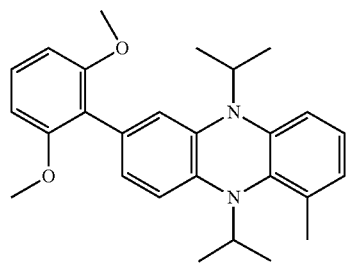
B-32
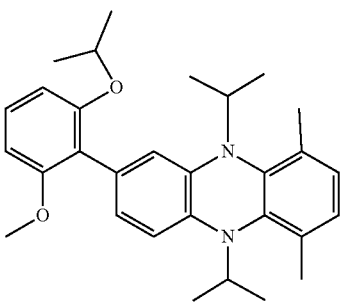
B-33
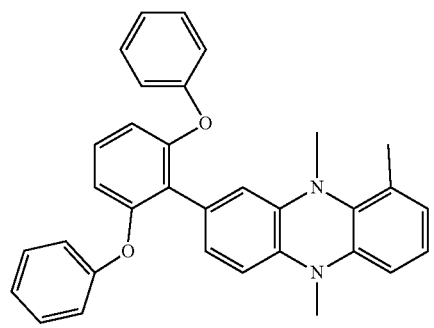
B-34
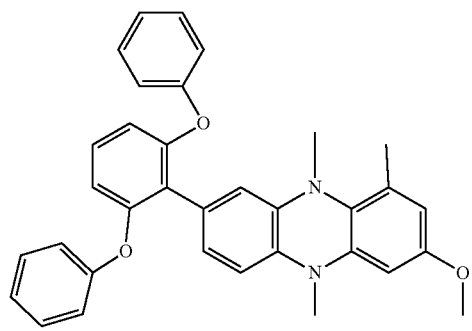
B-35
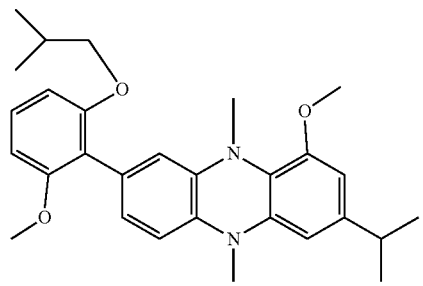
B-36
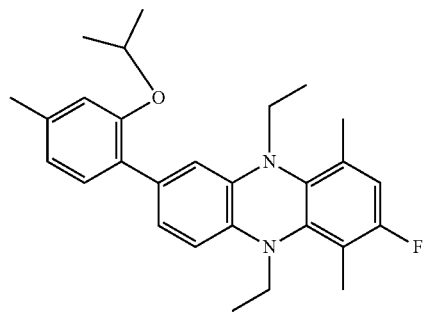
B-37
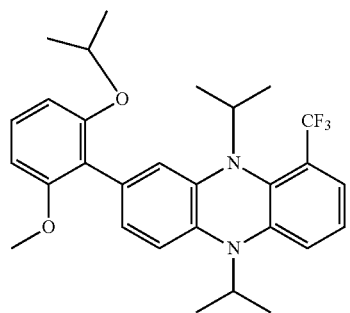
B-38
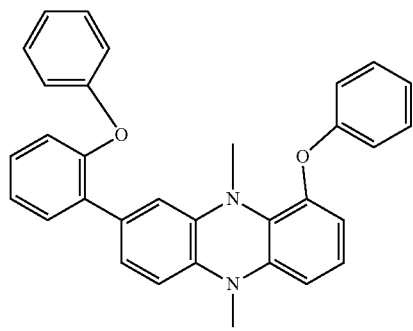
B-39
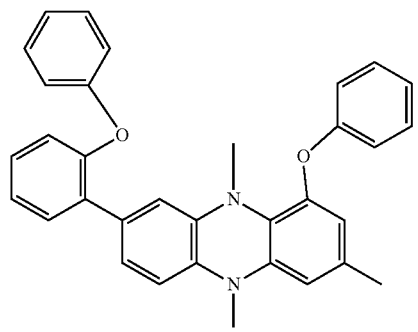
B-40
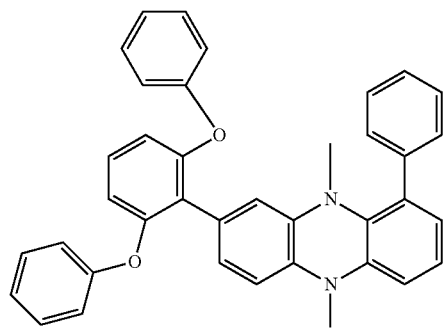

-continued
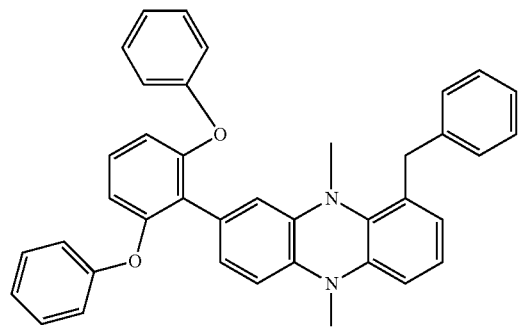
B-41
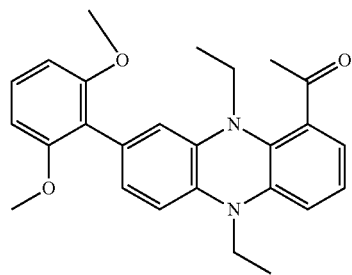
B-42
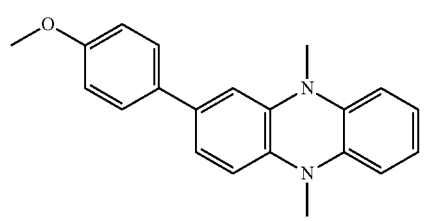
C-1
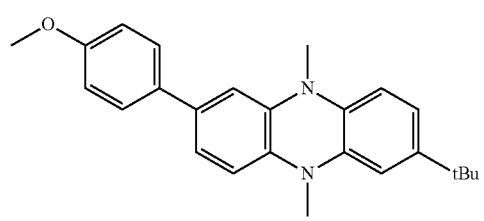
C-2
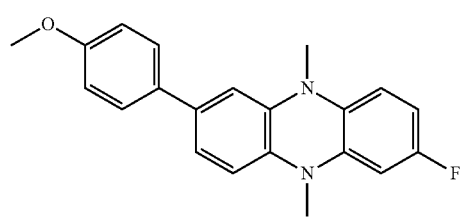
C-3
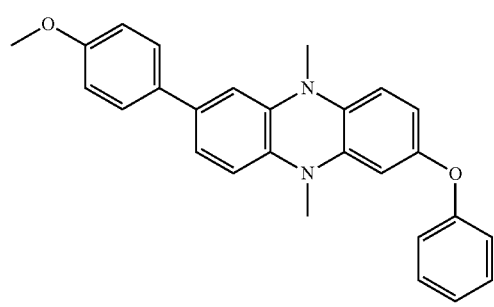
C-4
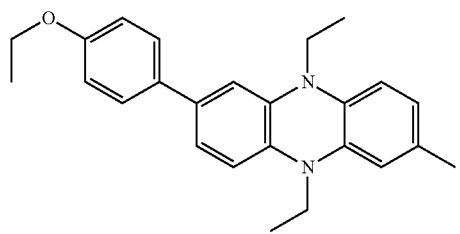
C-5
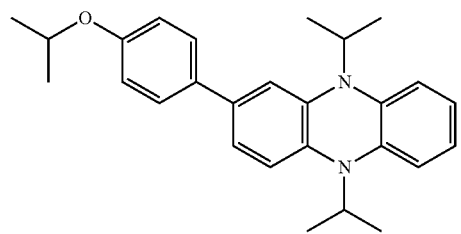
C-6
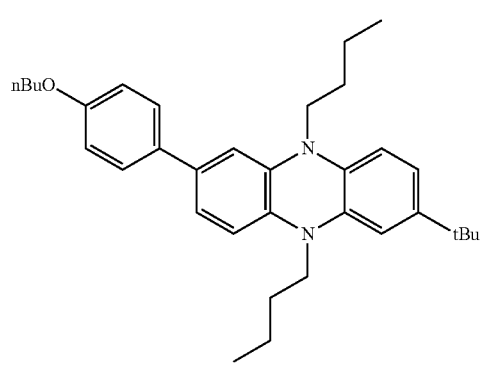
C-7
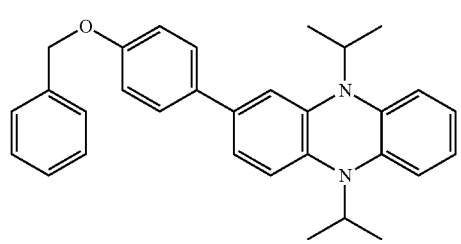
C-8

-continued
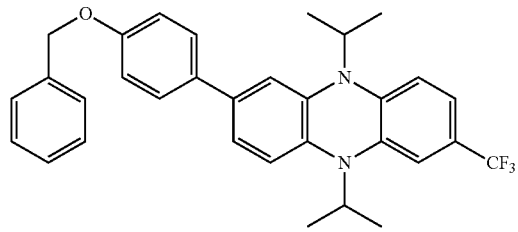
C-9
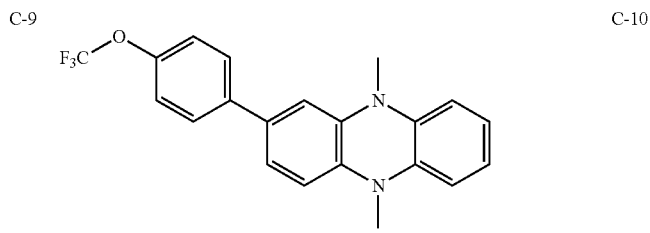
C-10
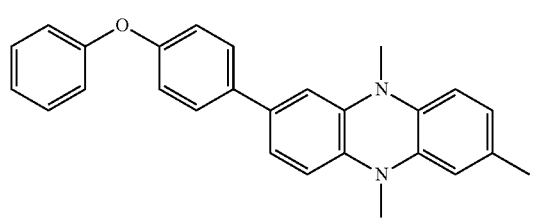
C-11
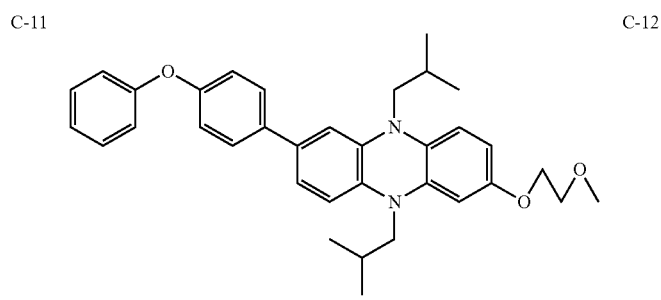
C-12
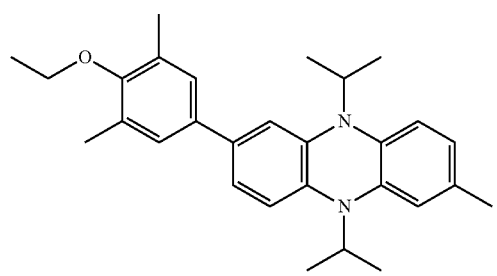
C-13
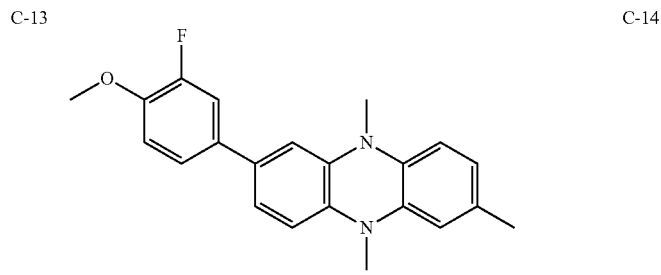
C-14
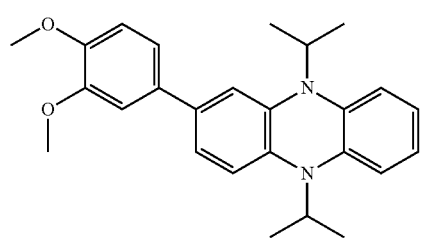
C-15
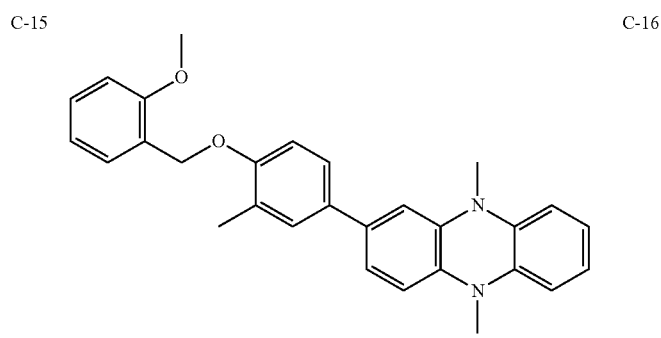
C-16
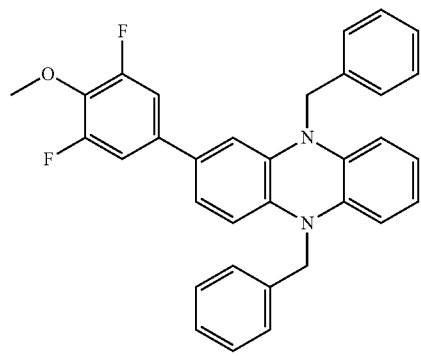
C-17
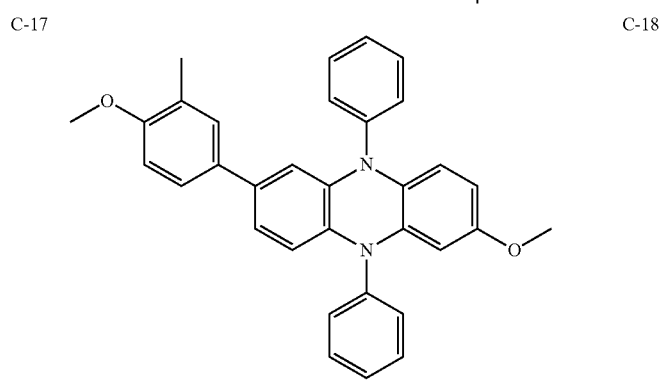
C-18

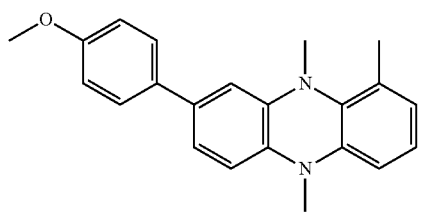 C-19
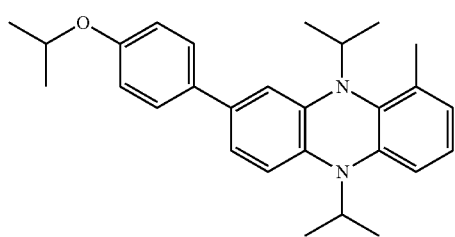 C-21
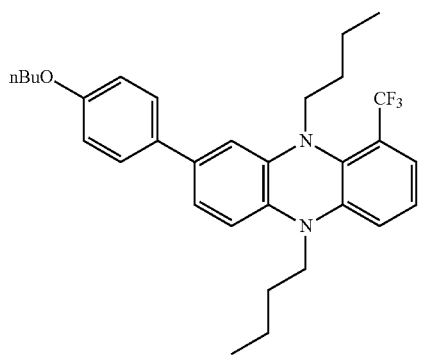 C-24
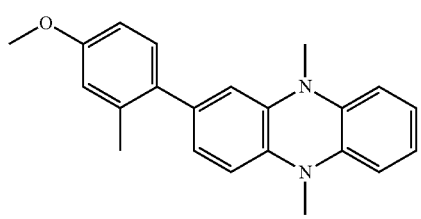 D-1
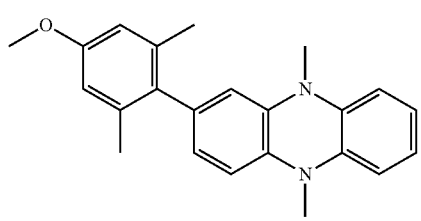 D-3
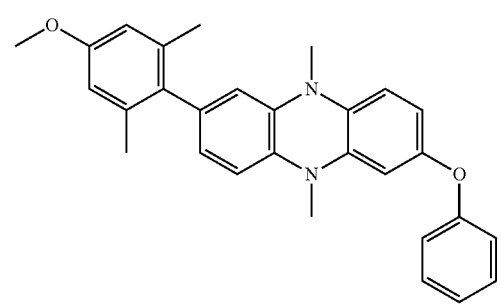

-continued
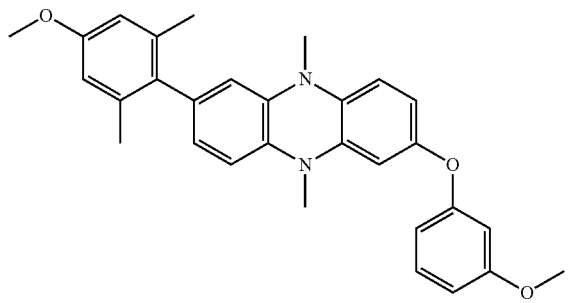
D-5
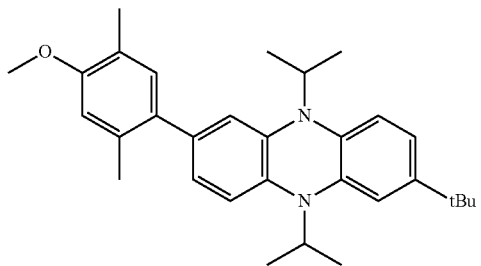
D-6
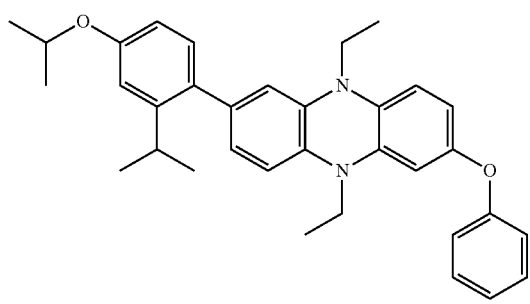
D-7
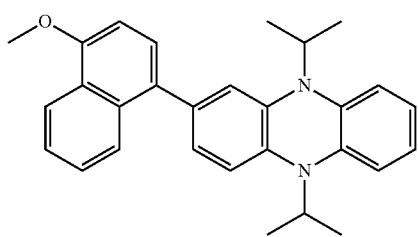
D-8
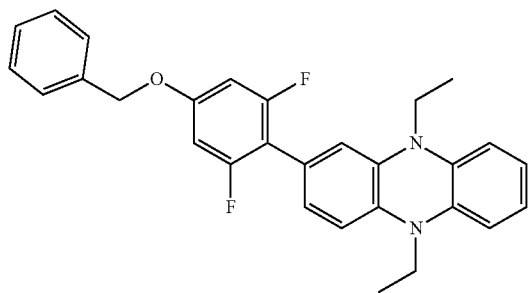
D-9
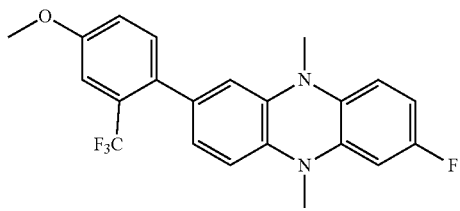
D-10
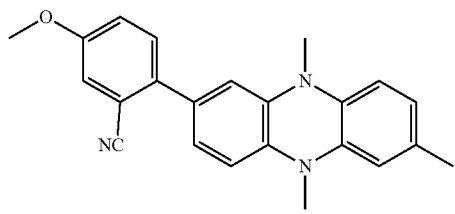
D-11
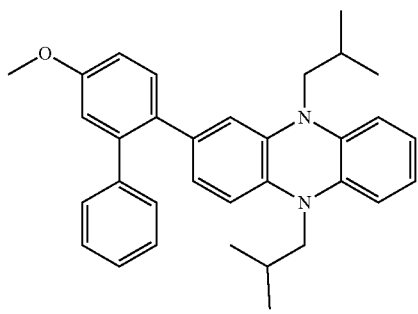
D-12
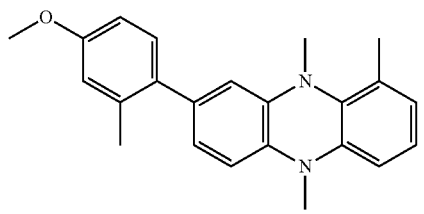
D-13
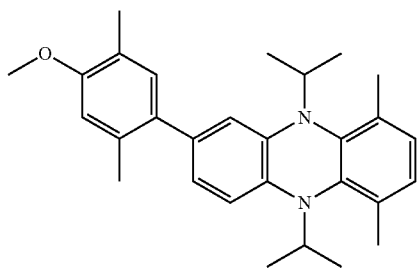
D-14

D-15
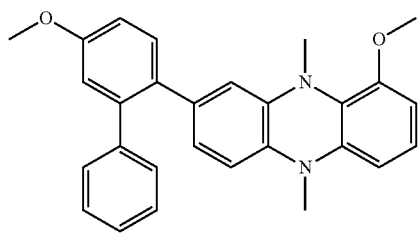
D-16
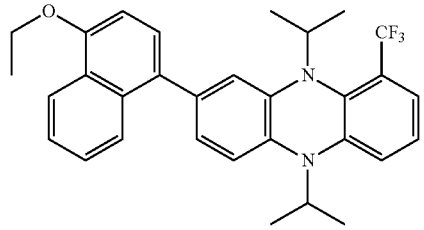
D-17
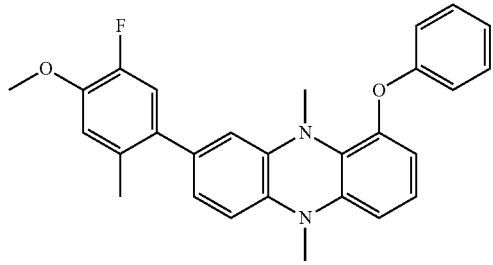
D-18
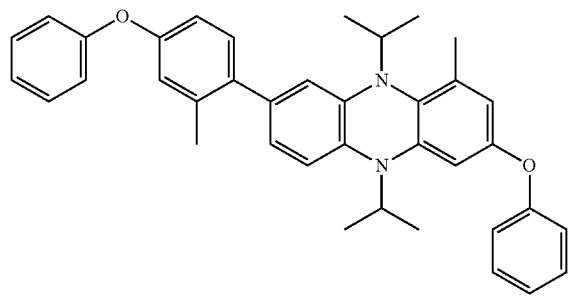
E-1
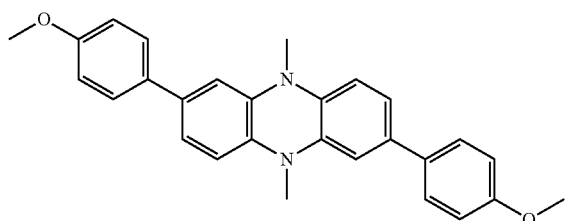
E-2
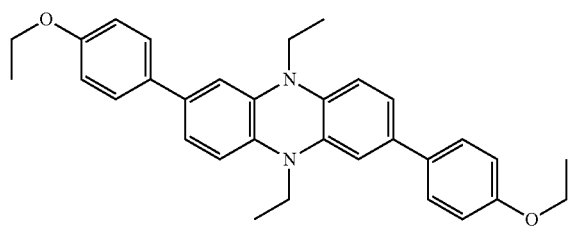
E-3
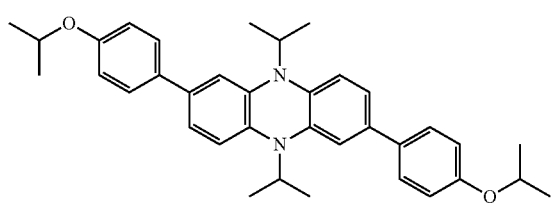
E-4
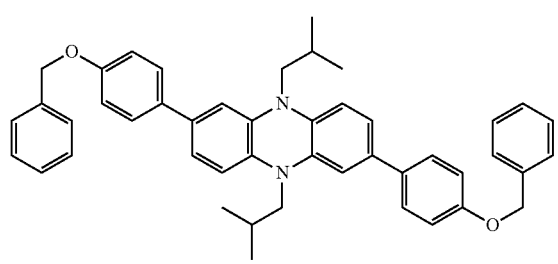
E-5
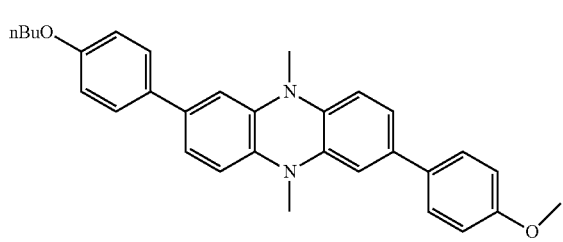
E-6
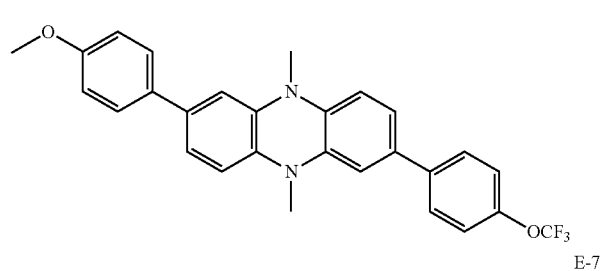
E-7
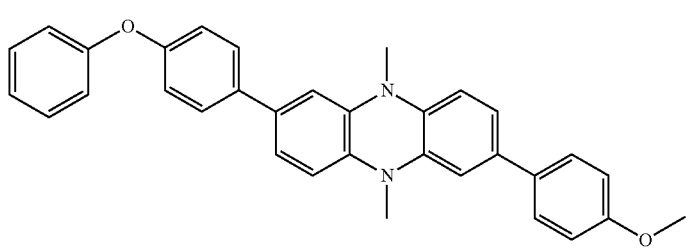

-continued
E-8
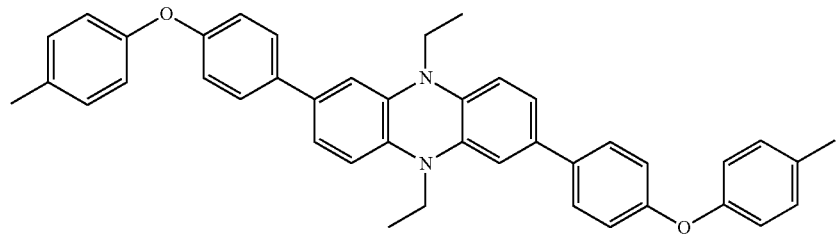
E-9
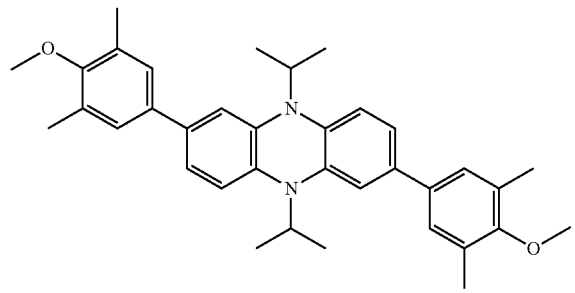
E-10
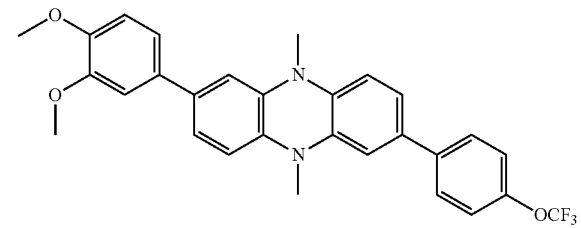
E-11
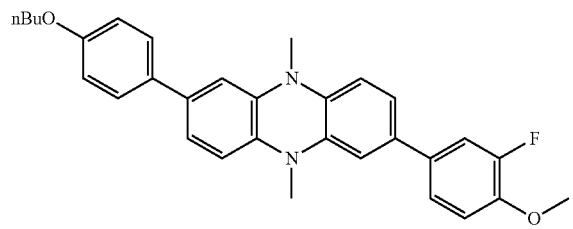
F-1
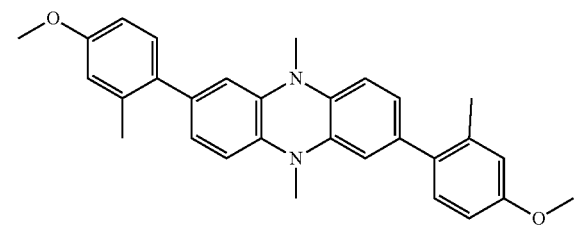
F-2
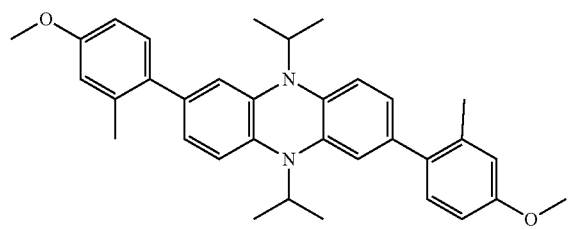
F-3
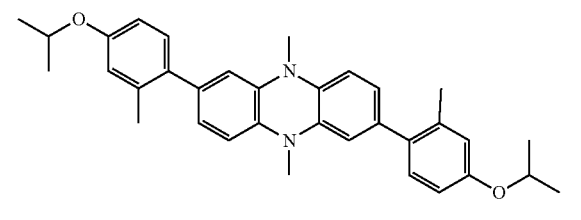
F-4
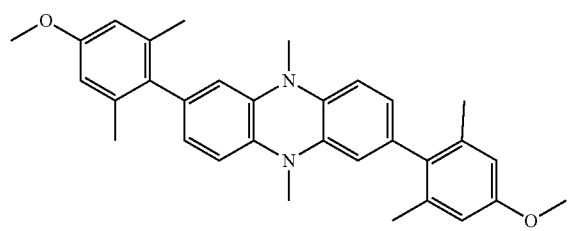
F-5
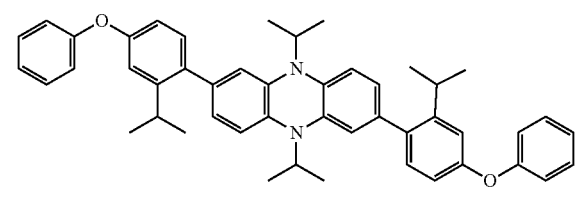
F-6
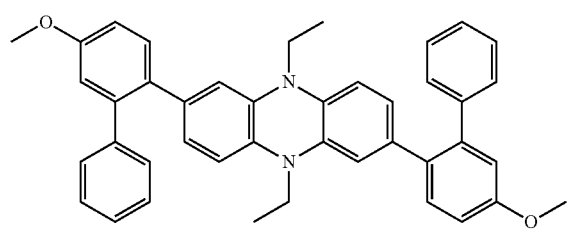
F-7
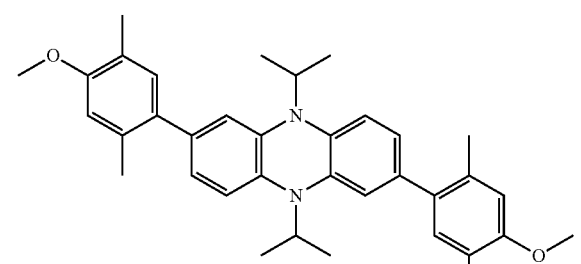

-continued
F-8
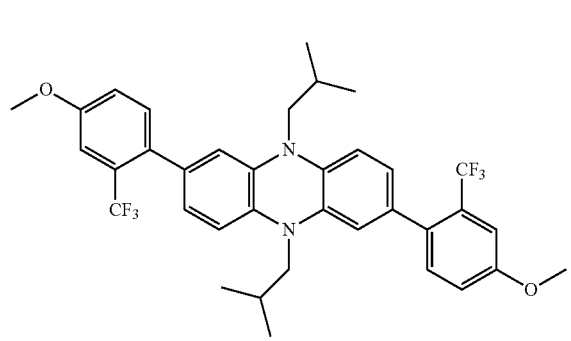
F9
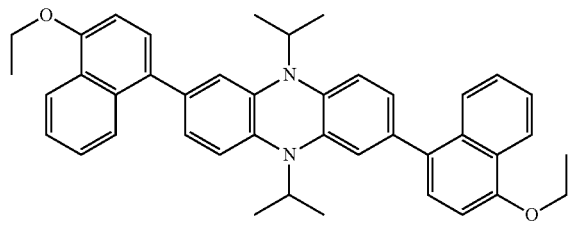
F-10
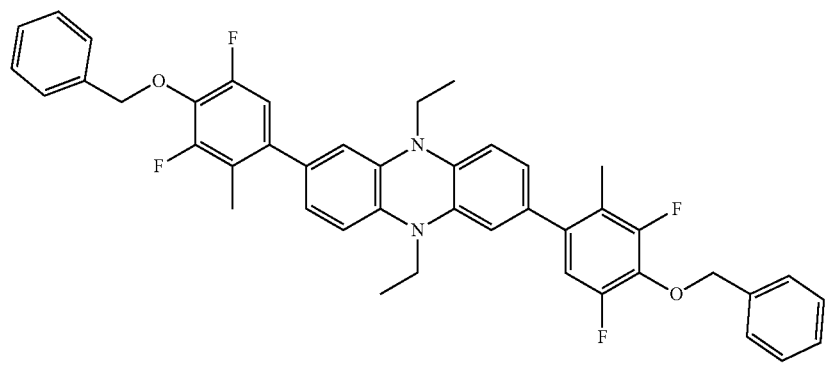
F-11
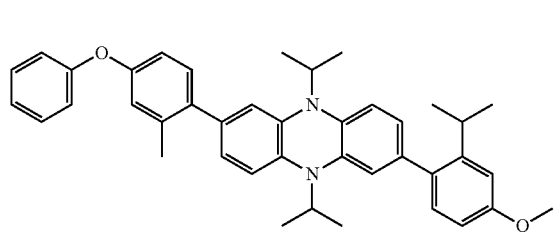
F-12
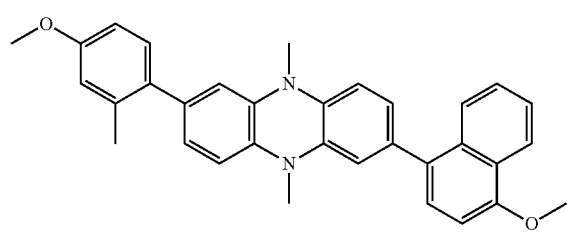
F-13
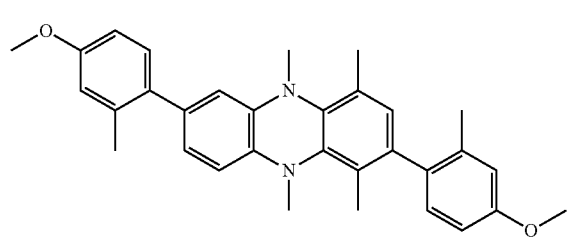
F-14
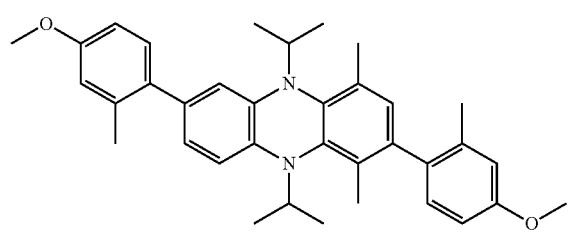
F-15
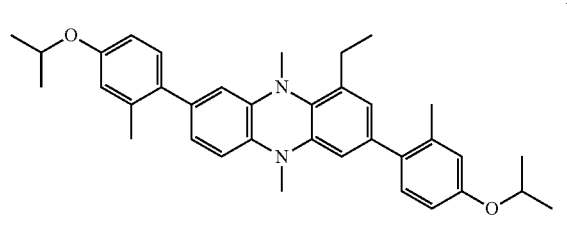
F-16
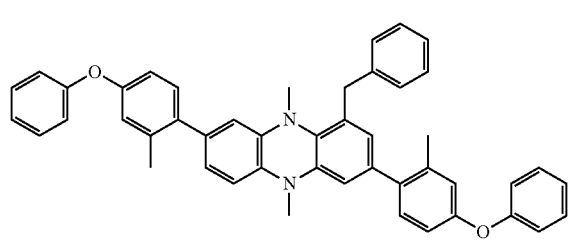

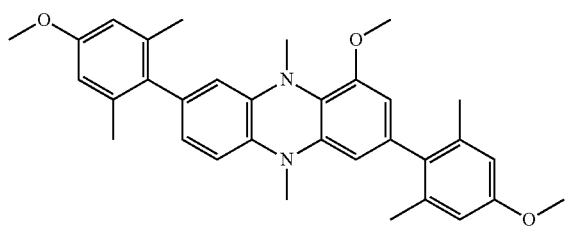

F-17

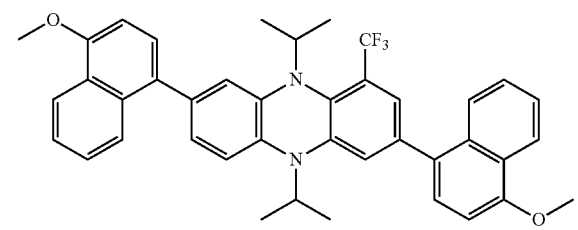

F-18

Among the example compounds, the organic compounds shown in the group A are examples compounds each represented by the general formula (4) or (5) in which two phenyl groups are bonded to one phenazine ring. The organic compounds shown in the group B are example compounds each represented by the general formula (2) or (3).

In addition, among the example compounds, the organic compounds shown in the group C are example compounds each represented by the general formula (6) in which one phenazine ring is substituted by one phenyl group. Among the compounds represented by the general formula (6), the organic compounds shown in the group D are example compounds in each of which at least one substituent is provided at at least one ortho position of the phenyl group. The organic compounds shown in the group E are compounds each represented by the general formula (7) and are example compounds in each of which one phenazine ring is substituted by two phenyl groups. Among the compounds represented by the general formula (7), the organic compounds shown in the group F are example compounds in each of which at least one substituent is provided at at least one of the ortho positions of each of the two phenyl groups.

In all the organic compounds described above, the phenazine ring functioning as an EC portion is substituted by a phenyl group having at least one of the ortho positions and the para position at which an alkoxy group or an aryloxy group is introduced. Hence, by the electronic effect of the alkoxy group or the aryloxy group provided at at least one of the ortho positions and the para position of the phenyl group, a molecular structure having an orbit which is likely to be mixed with that of the phenazine ring which forms a radical cation in an oxidized colored state. Accordingly, the organic compound having an EC property according to this embodiment has an absorption in a long wavelength region in a colored state as compared to that in the past.

In addition, since the phenazine ring functioning as an EC portion is substituted by a phenyl group having at least one of the ortho positions and the para position at which an alkoxy group or an aryloxy group is introduced, and the twist is generated between the phenazine ring and the phenyl group in a decolored state, it is expected that the transparency is improved. In order to improve the transparency in a decolored state, it is preferable that at least one of the ortho positions of the phenyl group be substituted by an alkoxy group or an aryloxy group, or at least one of the ortho positions of the phenyl group be substituted by an alkyl group, an aryl group, or an aralkyl group.

(Method for Synthesizing Organic Compound According to this Embodiment)

Among the organic compounds according to this embodiment, the organic compounds represented by the general formulas (2) to (5) can be synthesized by a reaction shown by the following formula (11). In the formula (11), Y represents a halogen atom. By the combination of a halogenated phenazine and a phenylboronic acid having at least one alkoxy group at at least one ortho position or a boronic acid ester compound, a precursor can be synthesized by a coupling reaction using a known Pd catalyst. Furthermore, by reduction and alkylation of the phenazine ring, the organic compound according to this embodiment can be synthesized. As one example, a synthetic scheme of the organic compound represented by the general formula (3) is shown by the following formula (11).

In this case, when the number of halogen atoms introduced by substitution to form the halogenated phenazine used as a starting raw material is set to 2, the compounds represented by the general formulas (4) and (5) can also be synthesized in a manner similar to that described above.

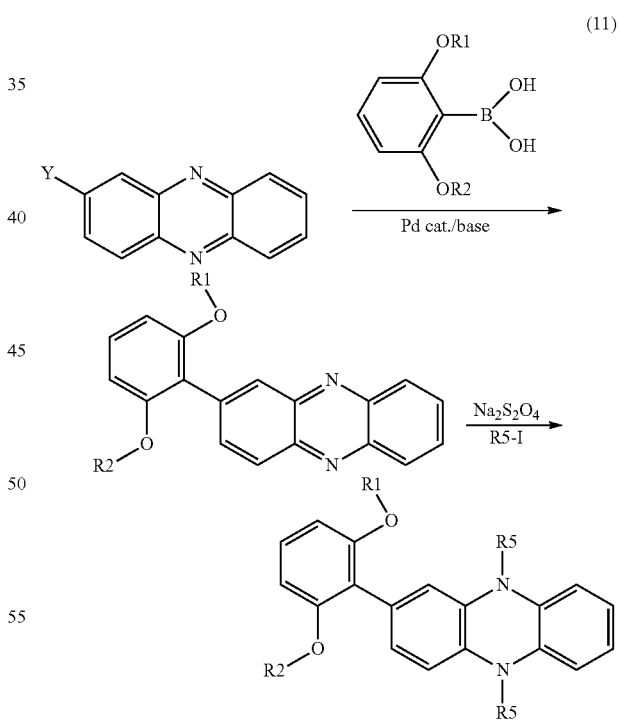

(11)

In addition, among the organic compounds according to this embodiment, the organic compound represented by the general formula (6) or (7) can be synthesized by a reaction shown by the following formula (12). In the formula (12), Y represents a halogen atom. By the combination of a halogenated phenazine and a phenylboronic acid having alkoxy groups at the ortho positions or a boronic acid ester compound, a precursor can be synthesized by a coupling reaction using a known Pd catalyst. Furthermore, by reduction and alkylation of the phenazine ring, the organic compound according to this embodiment can be synthesized. As one example, a synthetic scheme of the organic compound represented by the general formula (6) is shown by the following formula (12).

In this case, when the number of halogen atoms introduced by substitution to form the halogenated phenazine used as a starting raw material is set to 2, the compound represented by the general formula (7) can also be synthesized in a manner similar to that described above.

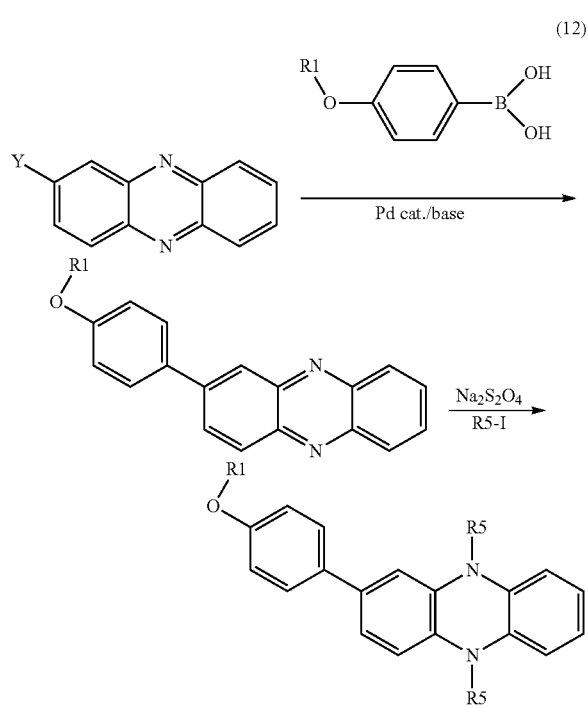

(12)

Second Embodiment

The organic compound having an EC property according to the first embodiment may be used as an electrochromic layer (EC layer) of an electrochromic element (EC element).

Figure 2:
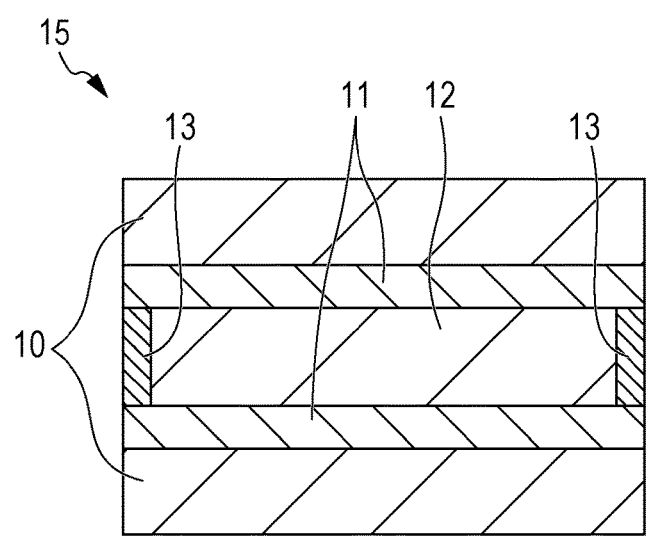
FIG. 2 is a schematic cross-sectional view showing one example of an electrochromic element according to an embodiment of the subject application.

Hereinafter, an EC element 15 according to this embodiment will be described with reference to FIG. 2. FIG. 2 is a schematic cross-sectional view illustrating the structure of the EC element 15 of this embodiment.

The EC element 15 has a pair of substrates 10, a pair of electrodes 11, an electrochromic layer (EC layer) 12 disposed between this pair of electrodes 11, and a sealing material 13. The EC layer 12 includes an electrolyte and the organic compound represented by the general formula (1). The distance between the electrodes 11 is set to be constant by the sealing material 13 such as spacers. In this EC element 15, the pair of electrodes 11 is disposed between the pair of substrates 10. In addition, the EC element 15 may include only the pair of electrodes 11 and the EC layer 12 disposed therebetween, and the pair of substrates 10 and the sealing material 13 are not always required.

The EC layer 12 includes the organic compound represented by the general formula (1) according to this embodiment and an electrolyte. The EC layer 12 may include a layer formed from an EC compound and a layer formed from an electrolyte. In addition, as a solution containing an EC compound and an electrolyte, the EC layer 12 may be provided. The EC element according to this embodiment is preferably an EC element including the EC layer 12 in the form of a solution.

Next, the members forming the EC element according to this embodiment will be described.

As the electrolyte, any material which is an ion dissociable salt and which has an excellent solubility to a solvent and a high compatibility to a solid electrolyte may be used without any particular restriction. In particular, electrolytes each having an electron donating property are preferable. Those electrolytes each may be called a supporting electrolyte.

As the electrolyte, for example, there may be mentioned inorganic ion salts, such as various alkali metal salts and alkaline earth metal salts, quaternary ammonium salts, and cyclic quaternary ammonium salts.

In particular, for example, there may be mentioned alkali metal salts of Li, Na, and K, such as $LiClO_4$, $LiSCN$, $LiBF_4$, $LiAsF_6$, $LiCF_3SO_3$, $LiPF_6$, $LiI$, $NaI$, $NaSCN$, $NaClO_4$, $NaBF_4$, $NaAsF_6$, $KSCN$, and $KCl$; quaternary ammonium salts, such as $(CH_3)_4NBF_4$, $(C_2H_5)_4NBF_4$, $(n-C_4H_9)_4NBF_4$, $(n-C_4H_9)_4NPF_6$, $(C_2H_5)_4NBr$, $(C_2H_5)_4NClO_4$, and $(n-C_4H_9)_4NClO_4$; and cyclic quaternary ammonium salts.

As a solvent dissolving an organic compound having an EC property and an electrolyte, although any material capable of dissolving an organic compound having an EC property and an electrolyte may be used without any particular restriction, a solvent having a polarity is particularly preferable.

In particular, for example, there may be mentioned water and organic polar solvents, such as methanol, ethanol, propylene carbonate, ethylene carbonate, dimethyl sulfoxide, dimethoxyethane, γ-butyrolactone, γ-valerolactone, sulfolane, dimethylformamide, dimethoxyethane, tetrahydrofuran, acetonitrile, propionitrile, 3-methoxypropionitrile, benzonitrile, dimethylacetamide, methylpyrrolidinone, and dioxolane.

A polymer or a gelation agent may be contained in the EC medium described above, so that a highly viscous material, a gel material, or the like may also be used.

The above polymer is not particularly limited, and for example, a polyacrylonitrile, a carboxymethyl cellulose, a poly(vinyl chloride), a polyethylene oxide), a poly(propylene oxide), a polyurethane, a polyacrylate, a polymethacrylate, a polyamide, a poly(acryl amide), a polyester, and Nafion (registered trade name) may be mentioned.

Next, the substrate 10 and the electrode 11 will be described. The substrate 10 is preferably transparent. As the substrate 10, for example, a colorless or a colored glass, a reinforced glass, and the like may be used. As those glass materials, optical glass substrates, such as Corning #7059 and BK-7, may be preferably used. In addition, a material, such as a plastic or a ceramic, may also be appropriately used as long as having a sufficient transparency. The substrate 10 is preferably formed of a material which has rigidity and is not likely to generate a strain. In addition, in this embodiment, the "transparency" indicates a transparency having a visible light transmittance of 50% or more.

As a material to be used as the substrate 10, for example, there may be mentioned a poly(ethylene terephthalate), a poly(ethylene naphthalate), a polynorbornene, a polyamide, a polysulfone, a poly(ether sulfone), a poly(ether ether ketone), a poly(phenylene sulfide), a polycarbonate, a polyimide, or a poly(methyl methacrylate).

The electrode 11 is preferably a transparent electrode. As a material of the electrode 11, for example, there may be mentioned a metal or its oxide, such as an indium tin oxide alloy (ITO), a fluorine-doped tin oxide (FTO), tin oxide (NESA), indium zinc oxide (IZO (registered trade name)), silver oxide, vanadium oxide, molybdenum oxide, gold, silver, platinum, copper, indium, or chromium; a silicon-based material, such as polycrystalline silicon or amorphous silicon; and a carbon material, such as carbon black, graphite, or glassy carbon. In addition, there may be preferably used an electrically conductive polymer having an improved electric conductivity by a doping treatment or the like, such as a polyaniline, a polypyrrole, a polythiophene, a polyacetylene, a polyparaphenylene, or a complex between a poly(ethylene dioxythiophene) (PEDOT)) and a polystyrene sulfonic acid.

Since the EC element 15 according to this embodiment preferably has a high transmittance in a decolored state, as the electrode 11, for example, ITO, IZO, NESA, PEDOT:PSS, or graphene is particularly preferably used. Those materials each may be used in various forms, such as a bulky form and fine particles. In addition, the materials of the electrode 11 may be used alone, or at least two thereof may be used in combination.

In addition, although the two electrodes 11 are each a transparent electrode in this embodiment, besides the case described above, in accordance with the application, the material is preferably appropriately selected in such a way that one of the pair of electrodes 11 is only formed as a transparent electrode.

As the sealing material 13, a material is preferable which is chemically stable, which allows a gas and a liquid not to pass therethrough, and which does not disturb an oxidation-reduction reaction of the EC material. For example, an inorganic material, such as a glass frit, an organic material, such as an epoxy resin, or a metal material may be used. In addition, the sealing material 13 may be allowed to have a function to maintain the distance between the two electrodes 11. In addition, when the sealing material 13 is not allowed to have a function as a spacer which defines the distance between the two electrodes 11, spacers (not shown) may be additionally disposed between the electrodes 11 so as to maintain the distance therebetween. As a raw material of the spacer, for example, an inorganic material, such as silica beads or glass fibers, or an organic material, such as a polydivinylbenzene, a polyimide, a polytetrafluoroethylene, a fluorinated rubber, or an epoxy resin may be used. By the spacers described above, a space is formed so as to receive the EC layer 12 including a solution which contains the organic compound having an EC property of this embodiment, and the distance between the electrodes can be maintained.

The EC element 15 according to this embodiment may have a liquid injection port through which a liquid containing an EC compound is injected in the space formed by the pair of electrodes 11 and the sealing material 13. After the organic compound having an EC property is injected through the liquid injection port, the injection port is covered with a sealing member and is then tightly sealed by an adhesive or the like, so that the element is formed. The sealing member may also have an isolation function so that the adhesive and the organic compound having an EC property are not brought into contact with each other. Although the shape of the sealing member is not particularly limited, a taper shape, such as a wedge shape, is preferable.

A method for forming the EC element 15 according to this embodiment is not particularly limited. For example, there may be used a method in which the EC layer 12 is formed by injecting a liquid containing an organic compound having an EC property prepared in advance into the space provided between a pair of electrodes by a vacuum injection method, an atmospheric injection method, a meniscus method, or the like.

The EC element 15 according to this embodiment may include the organic compound according to this embodiment represented by the general formula (1) and at least one different EC compound from the organic compound according to this embodiment. As the number of the at least one different EC compound may be one or two or more, and the different EC compound may be a compound to be colored in an oxidized state and/or in a reduced state. In particular, as the different EC compound, a compound to be colored in a reduced state is preferable.

In addition, the compound to be colored in an oxidized state is a compound having a low transmittance of visible light in an oxidized state as compared to that in a reduced state. The compound to be colored in a reduced state is a compound having a low transmittance of visible light in a reduced state as compared to that in an oxidized state.

The absorption wavelength region of the different EC compound is preferably in a range of 400 nm or less in a decolored state. The reason for this is that an EC element having a high transparency in a decolored state can be provided. On the other hand, the absorption wavelength region in a colored state is preferably in a range of 400 to 800 nm and more preferably in a range of 420 to 700 nm.

By combination with the different EC compound having an absorption in a different wavelength region in a colored state, an EC element which uniformly absorbs light at each wavelength in a visible light region can be formed. In addition, as the different EC compound, a different organic compound represented by the general formula (1) may be included. That is, the EC element may include at least two different organic compounds each represented by the general formula (1).

As the different EC compound according to this embodiment, for example, the following compounds may be mentioned.

As the different compound to be colored in an oxidized state, for example, there may be mentioned an oligothiophene, such as 3,3',4,4',5,5'-hexamethylbithiophene or 3,4-ethylenedioxy-2,5-dimethylthiophene; a phenazine-based compound, such as 5,10-dihydro-5,10-dimethylphenazine or 5,10-dihydro-5,10-diethylphenazine; a metallocene-based compound, such as ferrocene, tetra-t-butylferrocene, or titanocene; a phenylenediamine-based compound, such as N,N',N,N'-tetramethyl-p-phenylenediamine; or a pyrazoline-based compound, such as 1-phenyl-2-pyrazoline.

As the compound to be colored in a reduced state, for example, there may be mentioned a viologen-based compound, such as N,N'-diheptylbipyridinium diperchlorate, N,N'-diheptylbipyridinium ditetrafluoroborate, N,N'-diheptylbipyridinium dihexafluorophosphate, N,N'-diethylbipyridinium diperchlorate, N,N'-diethylbipyridinium ditetrafluoroborate, N,N'-diethylbipyridinium dihexafluorophosphate, N,N'-dibenzylbipyridinium diperchlorate, N,N'-dibenzylbipyridinium ditetrafluoroborate, N,N'-dibenzylbipyridinium dihexafluorophosphate, N,N'-diphenylbipyridinium diperchlorate, N,N'-diphenylbipyridinium ditetrafluoroborate, or N,N'-diphenylbipyridinium dihexafluorophosphate; an anthraquinone-based compound, such as 2-ethylanthraquinone, 2-t-butylanthraquinone, or octamethylanthraquinone;

or a ferrocenium salt-based compound, such as ferrocenium tetrafluoroborate or ferrocenium hexafluorophosphate; or a styryl-based compound.

The compound contained in the EC layer 12 of the EC element 15 according to this embodiment can be confirmed by extraction and analysis using a known method. For example, there may be a method in which after extraction is performed by a chromatography, analysis is performed using a nuclear magnetic resonance spectrum (NMR). In addition, when the EC layer 12 is a solid, analysis thereof may be performed using a time-of-flight secondary ion mass spectrometry (TOF-SIMS).

The organic compound represented by the general formula (1) has an absorption peak in a long wavelength region of 540 nm or more in a colored state, and the transparency in a neutral state (decolored state) is improved as compared to that in the past.

Since the organic compound according to this embodiment has in a colored state, an absorption peak in a long wavelength side region as compared to that in the past, by the organic compound represented by the general formula (1) itself or by the combination thereof with an EC compound having a color absorption in a different wavelength region, an EC element having various absorption colors can be provided. In addition, according to the EC element of this embodiment, the transparency in a decolored state can be improved. Furthermore, the EC element 15 according to this embodiment can be preferably used when the amount of light incident on an imaging element, such as a camera, is reduced.

Third Embodiment

The above EC element 15 according to this embodiment may be used for an optical filter, a lens unit, an imaging device, and the like. In this embodiment, an optical filter, a lens unit, and an imaging device each using the EC element 15 will be described.

Figure 3:
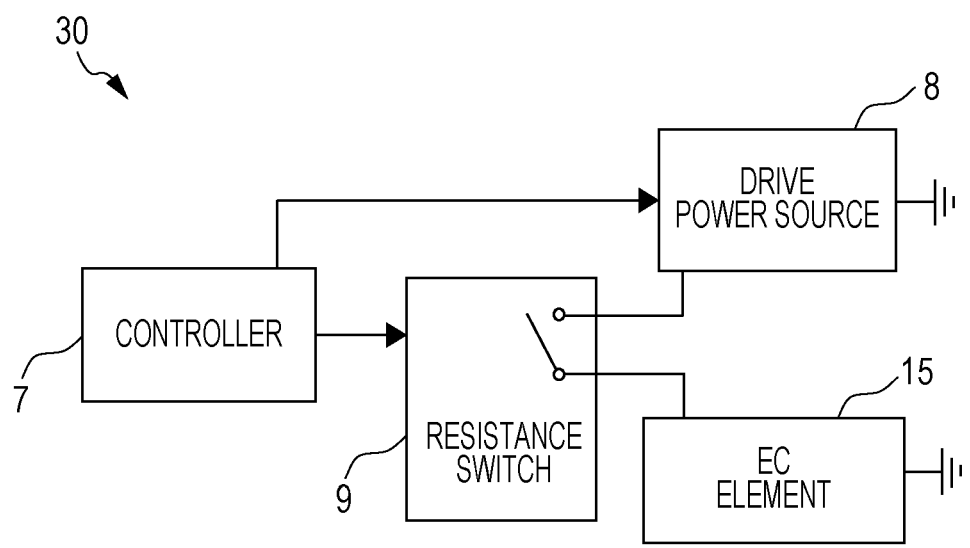
FIG. 3 is a block diagram illustrating the structure of an electrochromic device according to an embodiment of the subject application.

The optical filter includes an EC device 30 having the EC element 15 and a drive device connected thereto. FIG. 3 is a block diagram illustrating the structure of the EC device 30. The drive device connected to the EC element 15 includes a drive power source 8, a resistance switch 9, and a controller 7.

The drive power source 8 applies to the EC element 15, a voltage required to enable an EC material contained in the EC layer 12 to cause an electrochemical reaction.

The drive voltage is more preferably a constant voltage. The reason for this is that when the EC material is formed of a plurality of materials, since the absorption spectrum may be changed in some cases due to the difference in oxidation-reduction potential and molar absorption coefficient between the materials, a constant voltage is preferably applied.

The start of the voltage application and the retention of the application state of the drive power source 8 are performed by signals from the controller 7, and in the period in which the optical transmittance of the EC element 15 is controlled, the constant-voltage application state is retained.

The resistance switch 9 switches between a resistor R1 and a resistor R2 larger than the resistor R1 to form a series connection in a closed circuit including the drive power source 8 and the EC element 15. As the resistance of the resistor R1, a resistance at least smaller than the largest impedance of the element closed circuit is preferable and is preferably 10Ω or less. As the resistance of the resistor R2, a resistance larger than the largest impedance of the element closed circuit is preferable and is preferably 1 MΩ or more. In addition, the resistor R2 may be air in some cases. In this case, although the closed circuit is exactly changed to an open circuit, when air is regarded as the resistor R2, the circuit can be assumed as a closed circuit.

The control circuit 7 transmits a switching signal to the resistance switch 9 to control the switching between the resistor R1 and the resistor R2.

The lens unit according to this embodiment includes a plurality of lenses and an optical filter including the EC element 15. The optical filter may be provided either between the plurality of lenses or outside the lenses. The optical filter is preferably provided on the optical axes of the lenses.

The imaging device according to this embodiment includes an optical filter and a light receiving element receiving light which passes through this optical filter.

As the imaging device, in particular, there may be mentioned a camera, a video camera, a camera-equipped mobile phone, or the like. The imaging device may have the structure in which a main body including a light receiving element and a lens unit having lenses are separated from each other.

In this case, when the imaging device has the structure in which a main body and a lens unit can be separated from each other, the structure in which an optical filter independent of the imaging device is used for image formation is also included in the present disclosure. In addition, in the case described above, as the position at which the optical filter is disposed, for example, there may be mentioned a position outside the lens unit, a position between the lens unit and the light receiving element, or a position between lenses (in the case in which the lens unit includes a plurality of lenses).

Figure 4A:
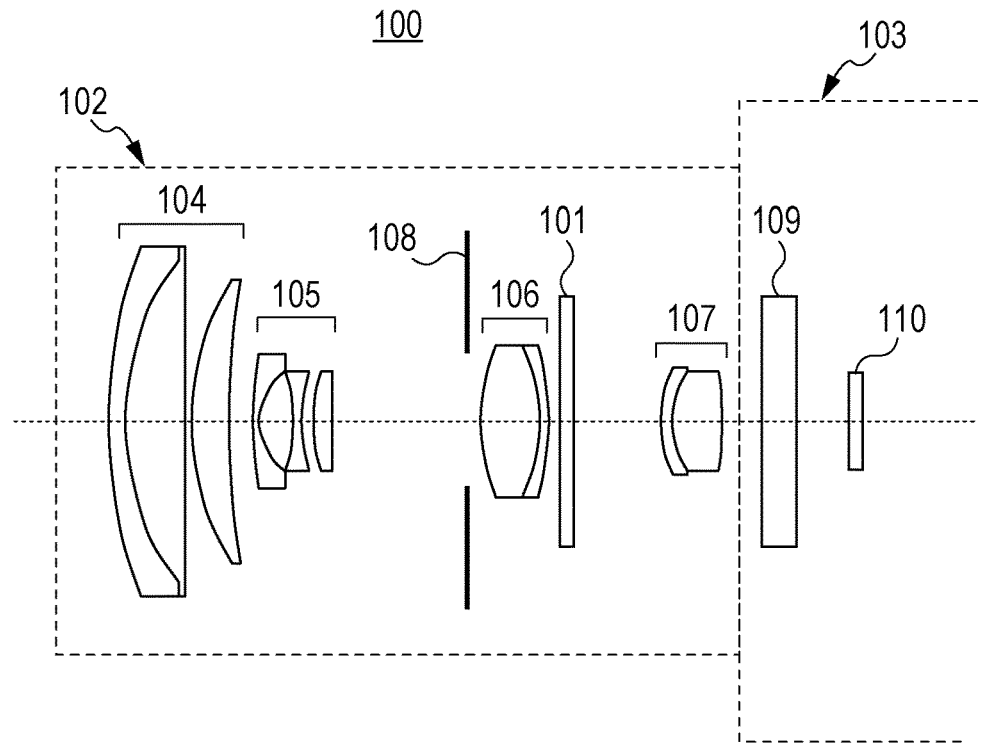
FIG. 4A is a schematic view illustrating the structure of one example of an imaging device according to an embodiment of the subject application.
Figure 4B:
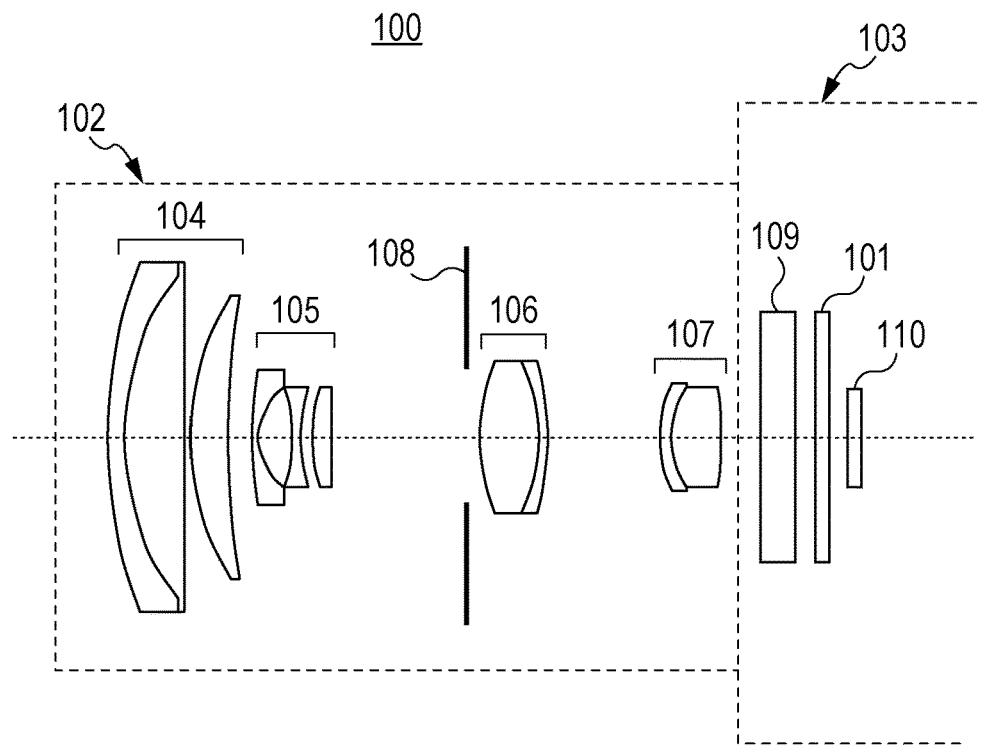
FIG. 4B is a schematic view illustrating the structure of another example of the imaging device according to an embodiment of the subject application.

FIGS. 4A and 4B are schematic views each illustrating one example of the structure of an imaging device 100 using the optical filter of this embodiment.

The imaging device 100 is an imaging device including a lens unit 102 and an imaging unit 103.

The lens unit 102 includes an optical filter 101 and an imaging optical system which includes a plurality of lenses or lens groups. The optical filter 101 is the optical filter of the above embodiment.

The lens unit represents, for example, in FIG. 4A, a rear focus type zoom lens which performs focusing behind a diaphragm. In the lens unit, four lens groups, that is, a first lens group 104 having a positive refractive power, a second lens group 105 having a negative refractive power, a third lens group 106 having a positive refractive power, and a fourth lens group 107 having a positive refractive power, are disposed in this order from an object side. The magnification change is performed by changing the distance between the second lens group 105 and the third lens group 106, and the focusing is performed by moving a part of the fourth lens group 107.

The lens unit 102 includes a diaphragm 108 between the second lens group 105 and the third lens group 106 and the optical filter 101 between the third lens group 106 and the fourth lens group 107. The lens groups 104 to 107, the diaphragm 108, and the optical filter 101 are disposed so that light passing through the lens unit passes therethrough, and the light amount can be adjusted using the diaphragm 108 and the optical filter 101.

The lens unit 102 is detachably connected to the imaging unit 103 with a mounting member (not shown) interposed therebetween.

In addition, in this embodiment, although the optical filter 101 is disposed between the third lens group 106 and the fourth lens group 107 in the lens unit 102, the imaging device 100 is not limited to the structure described above. For example, the optical filter 101 may be provided at either a front side (an object side) or a rear side (an imaging unit 103 side) of the diaphragm 108 and may also be provided either at a front side or at a rear side of any of the first lens group 104 to the fourth lens group 107. In addition, when the optical filter 101 is disposed at a position to which light is converged, advantages, such as reduction in area of the optical filter 101, may be obtained.

In addition, the structure of the lens unit 102 is not limited to the structure described above and may be appropriately selected. For example, besides the rear focus type, an inner focus type in which focusing is performed in front of the diaphragm or another type may also be used. In addition, besides the zoom lens, a specific lens, such as a fish-eye lens or a microlens, may also be appropriately selected.

The imaging unit 103 includes a glass block 109 and a light receiving element 110.

The glass block 109 is a glass block, such as a low-pass filter, a face plate, or a color filter.

In addition, the light-receiving element 110 is a sensor portion receiving light passing through the lens unit, and an imaging element, such as a CCD or a CMOS, may be used. In addition, a photo sensor, such as a photodiode, may also be used, and an element which obtains information on the intensity or the wavelength of light and outputs the information thereof may be appropriately used.

As shown in FIG. 4A, in the case in which the optical filter 101 is assembled in the lens unit 102, the drive device may be provided either in or outside the lens unit 102. When being disposed outside the lens unit 102, the drive device is connected to the EC element 15 in the lens unit 102 through wires provided therebetween, so that the drive control is performed.

In addition, in the structure of the above imaging device 100, the optical filter 101 is disposed in the lens unit 102. However, the present disclosure is not limited to this structure, and the optical filter 101 may be disposed at an appropriate position in the imaging device 100, and the light receiving element 110 may be disposed so as to receive light passing through the optical filter 101.

For example, as shown in FIG. 4B, the imaging unit 103 may include the optical filter 101. FIG. 4B is a schematic view illustrating the structure of another example of the imaging device of this embodiment and showing the structure of the imaging device in which the optical filter 101 is included in the imaging unit 103. In FIG. 4B, for example, the optical filter 101 is disposed right in front of the light receiving element 110. When the imaging unit itself includes the optical filter 101, since the lens unit 102 itself to be connected to the imaging unit is not required to have the optical filter 101, an imaging device capable of controlling the amount of light can be formed using an existing lens unit.

The imaging device 100 according to this embodiment may be applied to a product having a light amount adjustment function and a light receiving element in combination. For example, the imaging device 100 according to this embodiment may be used for a camera, a digital camera, a video camera, or a digital video camera and may also be applied to a product, such as a mobile phone, a smart phone, a personal computer (PC), or a tablet, including an imaging device.

Fourth Embodiment

Figure 7A:
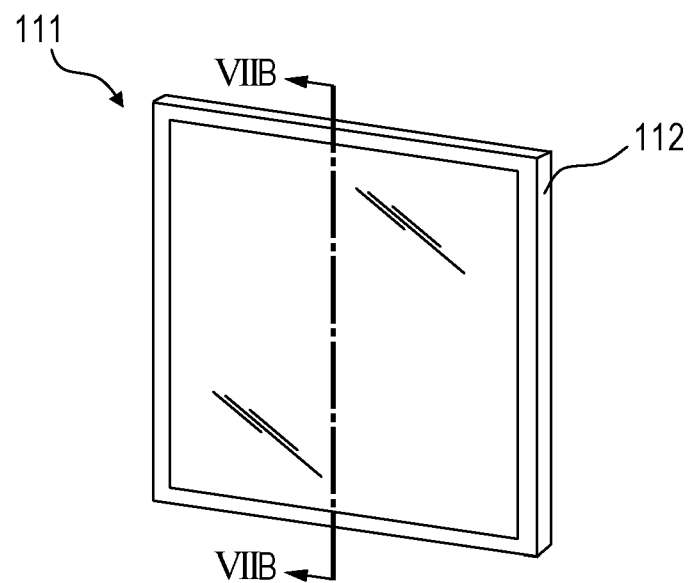
FIG. 7A is a perspective view illustrating the structure of a window material of an embodiment of the subject application.
Figure 7B:
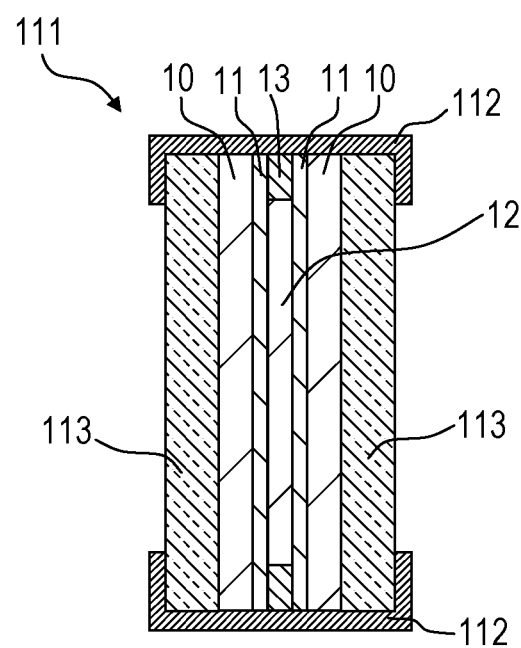
FIG. 7B is a cross-sectional view of the window material of an embodiment taken along the line VIIB-VIIB.

The EC element 15 according to the above embodiment may also be used for a window material. In this embodiment, a window material 111 using the EC element 15 will be described. FIG. 7A is a perspective view illustrating the structure of the window material 111, and FIG. 7B is a schematic cross-sectional view taken along the line VIIB-VIIB of FIG. 7A.

The window material 111 according to this embodiment includes the EC element 15 usable as an optical filter, transparent plates 113 sandwiching the optical filter, and frames 112 surrounding the entirety for integration. The EC element 15 is connected to a drive device (not shown). The drive device (not shown) may be integrated in the frame 112 or may be disposed outside the frame 112 so as to be connected to the EC element 15 through wires.

The transparent plate 113 is not particularly limited as long as having a high optical transmittance, and in consideration of the use as a window, a glass material is preferably used.

A material of the frame 112 is not particularly limited, and in general, a member which covers at least a part of the optical filter and which has an integrated form may be regarded as the frame.

In the figure, although the EC element 15 is a constituent member independent of the transparent plate 113, for example, the substrate 10 of the EC element 15 may be regarded as the transparent plate 113.

The window material 111 according to this embodiment may be used, for example, for the application in which the amount of sun light incident on a room during daytime is adjusted. Besides the amount of sun light, since the heat amount can also be adjusted, the window material 111 according to this embodiment may also be used for the control of interior brightness and temperature. In addition, as a shutter, the above window material 111 may also be used for the application in which viewing from the outside into a room is blocked.

The photochromic window as described above may also be applied, for example, to glass windows for buildings, and windows of vehicles, such as an automobile, an air plane, and a ship.

As described above, the EC element including an EC layer which contains the organic compound represented by the general formula (1) may be used for an optical filter, a lens unit, an imaging device, a window material, and the like. The optical filter, the lens unit, the imaging device, and the window material according to this embodiment are each able to provide variable absorption colors by using only the organic compound represented by the general formula (1) or by combination thereof with an EC compound having a color absorption in a different wavelength region. In addition, the optical filter, the lens unit, the imaging device, and the window material according to the above embodiments each contain the organic compound represented by the general formula (1), and hence, the transparency in a decolored state can be improved.

In addition, according to the imaging device 100 of this embodiment, since the optical filter 101 is used as a photochromic member, the amount of light passing therethrough can be appropriately changed only by one filter, and as a result, the reduction in number of members and the reduction in space can be advantageously obtained.

EXAMPLES

Hereinafter, although examples will be described, the present disclosure is not limited thereto.

Example 1

<Synthesis of Example Compound A-21>

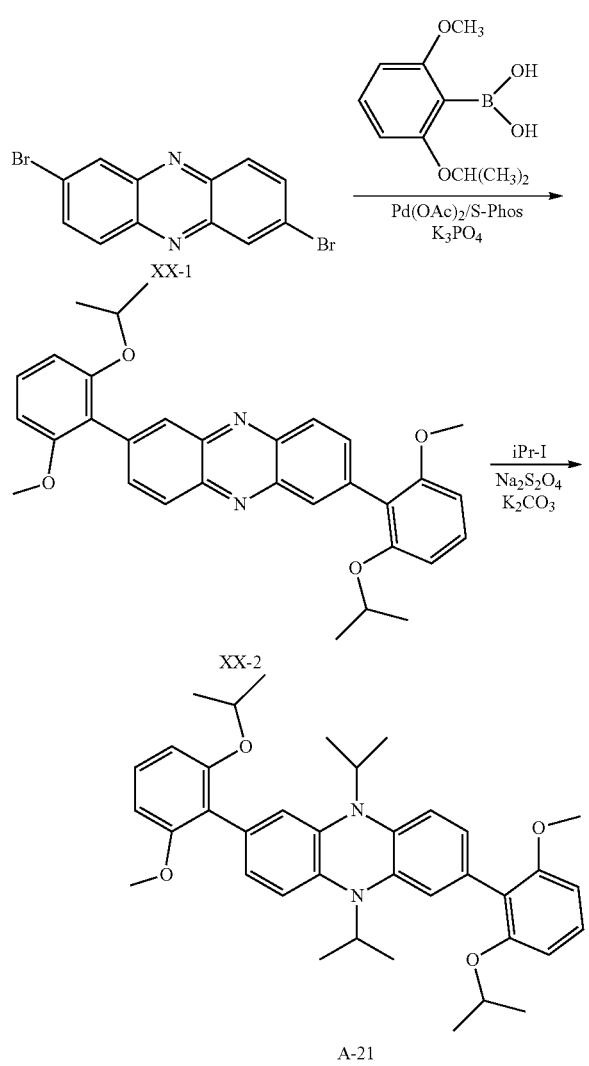

The example compound A-21 can be synthesized, for example, by the following procedure. First, a compound XX-2 is synthesized. In a 50-ml reaction chamber, 676 mg (2.0 mmol) of a compound XX-1 and 1.26 g (6.0 mmol) of 2-isopropoxy-6-methoxyphenylboronic acid were mixed together in a mixed solvent of tolune/1,4-dioxane (7 ml/7 ml), and dissolved oxygen was removed by nitrogen. In addition, the compound XX-1 was a compound synthesized in accordance with Tetrahedron Letters, 52, 6484 (2011).

Next, 18.0 mg (0.08 mmol) of $Pd(OAc)_2$, 82.1 mg (0.10 mmol) of 2-dicyclohexylphosphino-2',6'-dimethoxybiphenyl (S-Phos), and 2.30 g (10.0 mmol) of tripotassium phosphate were added in a nitrogen atmosphere, and a reaction was performed by heating and refluxing at 110° C. for 8 hours.

After the reaction solution was cooled to room temperature and was then condensed at a reduced pressure, separation and purification were performed by a silica gel chromatography (mobile phase: hexane/chloroform), so that a yellow solid compound XX-2 was obtained (770 mg, yield: 75%).

Next, the example compound A-21 is synthesized. In a 50-ml reaction chamber, 350 mg (0.69 mmol) of the compound XX-2 and 3.51 g (20.6 mmol) of 2-iodopropane were mixed together in a mixed solvent of acetonitrile/water (10 ml/1 ml), and dissolved oxygen was removed by nitrogen. Next, 600 mg (3.44 mmol) of sodium hydrosulfite and 599 mg (4.13 mmol) of potassium carbonate were added in a nitrogen atmosphere, and a reaction was performed by heating and refluxing at 90° C. for 9 hours.

After the reaction solution was cooled to room temperature and was then condensed at a reduced pressure, separation and purification were performed by a silica gel chromatography (mobile phase: hexane/toluene), so that a solid compound A-21 was obtained (110 mg, yield: 26%).

By a nuclear magnetic resonance spectrum (NMR) measurement, the structure of the obtained compound was identified. As a result, the ratio of peak integration values well coincided with that of the structure, so that the obtained compound was identified as the example compound A-21. The measurement result of the NMR spectrum is shown below.

$^1$H-NMR (deuterated acetone) δ(ppm): 7.19 (t, 2H), 6.8-6.65 (m, 10H), 4.45 (sep, 2H), 4.11 (sep, 2H), 3.62 (s, 6H), 1.52 (d, 12H), 1.24 (d, 12H).

Example 2

<Synthesis of Example Compound B-18>

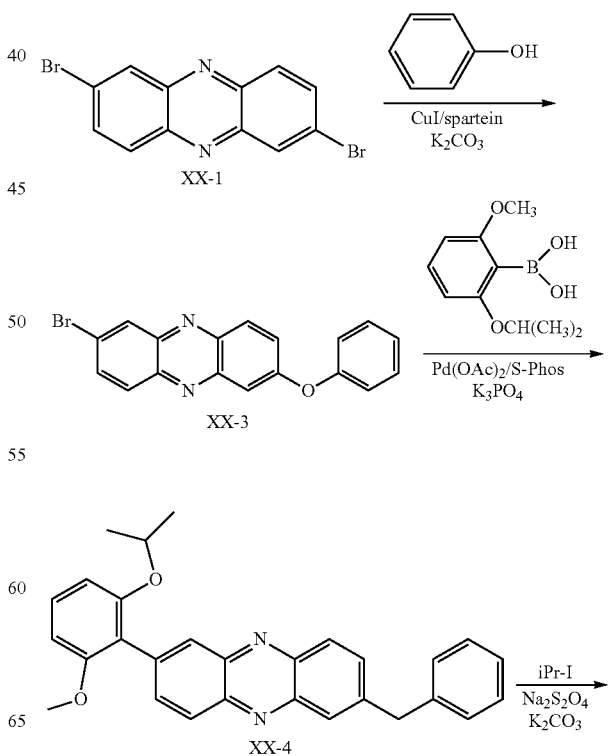

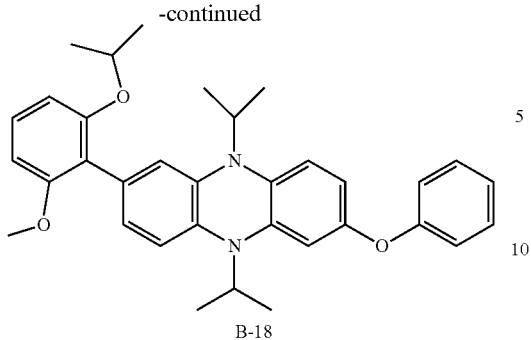

B-18

The example compound B-18 can be synthesized, for example, by the following procedure. First, a compound XX-3 is synthesized. In a 100-ml reaction chamber, 500 mg (1.48 mmol) of the compound XX-1 and 278 mg (2.96 mmol) of phenol were mixed together in dimethyl sulfoxide (DMSO) (5 ml), and dissolved oxygen was removed by nitrogen. Next, 62.8 mg (0.074 mmol) of a CuI/Sparteine complex and 409 mg (2.96 mmol) of potassium carbonate were added in a nitrogen atmosphere, and a reaction was performed by heating and refluxing at 110° C. for 8 hours.

After the reaction solution was cooled to room temperature and was then condensed at a reduced pressure, separation and purification were performed by a silica gel chromatography (mobile phase: hexane/chloroform), so that a yellow solid compound XX-3 was obtained (160 mg, yield: 32%).

Next, a compound XX-4 is synthesized. In a 50-ml reaction chamber, 160 mg (0.46 mmol) of the compound XX-3 and 144 mg (0.69 mmol) of 2-isopropoxy-6-methoxyphenylboronic acid were mixed together in a mixed solvent of tolune/1,4-dioxane (4 ml/4 ml), and dissolved oxygen was removed by nitrogen.

Next, 4.1 mg (0.018 mmol) of Pd(OAc)$_2$, 19 mg (0.046 mmol) of 2-dicyclohexylphosphino-2',6'-dimethoxybiphenyl (S-Phos), and 526 mg (2.29 mmol) of tripotassium phosphate were added in a nitrogen atmosphere, and a reaction was performed by heating and refluxing at 110° C. for 15 hours.

After the reaction solution was cooled to room temperature and was then condensed at a reduced pressure, separation and purification were performed by a silica gel chromatography (mobile phase: hexane/chloroform), so that a yellow solid compound XX-4 was obtained (170 mg, yield: 85%).

Next, the example compound B-18 is synthesized. In a 50-ml reaction chamber, 170 mg (0.39 mmol) of the compound XX-4 and 1.99 g (11.7 mmol) of 2-iodopropane were mixed together in a mixed solvent of acetonitrile/water (10 ml/1 ml), and dissolved oxygen was removed by nitrogen. Next, 340 mg (1.95 mmol) of sodium hydrosulfite and 323 mg of (2.34 mmol) of potassium carbonate were added in a nitrogen atmosphere, and a reaction was performed by heating and refluxing at 90° C. for 10 hours.

After the reaction solution was cooled to room temperature and was then condensed at a reduced pressure, separation and purification were performed by a silica gel chromatography (mobile phase: hexane/toluene), so that a solid example compound B-18 was obtained (120 mg, yield: 59%).

According to the result of a nuclear magnetic resonance spectrum (NMR) measurement, the ratio of peak integration values well coincided with that of the structure, so that the obtained compound was identified as the example compound B-18. The measurement result of the NMR spectrum is shown below.

$^1$H-NMR (deuterated acetone) δ(ppm): 7.35 (m, 2H), 7.19 (t, 1H), 7.06 (t, 1H), 6.99 (d, 2H), 6.8-6.65 (m, 6H), 6.49 (d, 1H), 6.42 (dd, 1H), 4.47 (sep, 1H), 4.17 (sep, 1H), 3.97 (sep, 1H), 3.71 (s, 3H), 1.51 (d, 6H), 1.46 (d, 6H), 1.18 (d, 6H).

Comparative Example 1

As Comparative Example 1, the example compound Ref-1, which is the known EC compound described above, is used. The example compound Ref-1 is a phenazine derivative substituted by two phenyl groups each having no alkoxy substituents at the ortho positions thereof.

Example 3

<Neutral Transparency>

Figure 5:
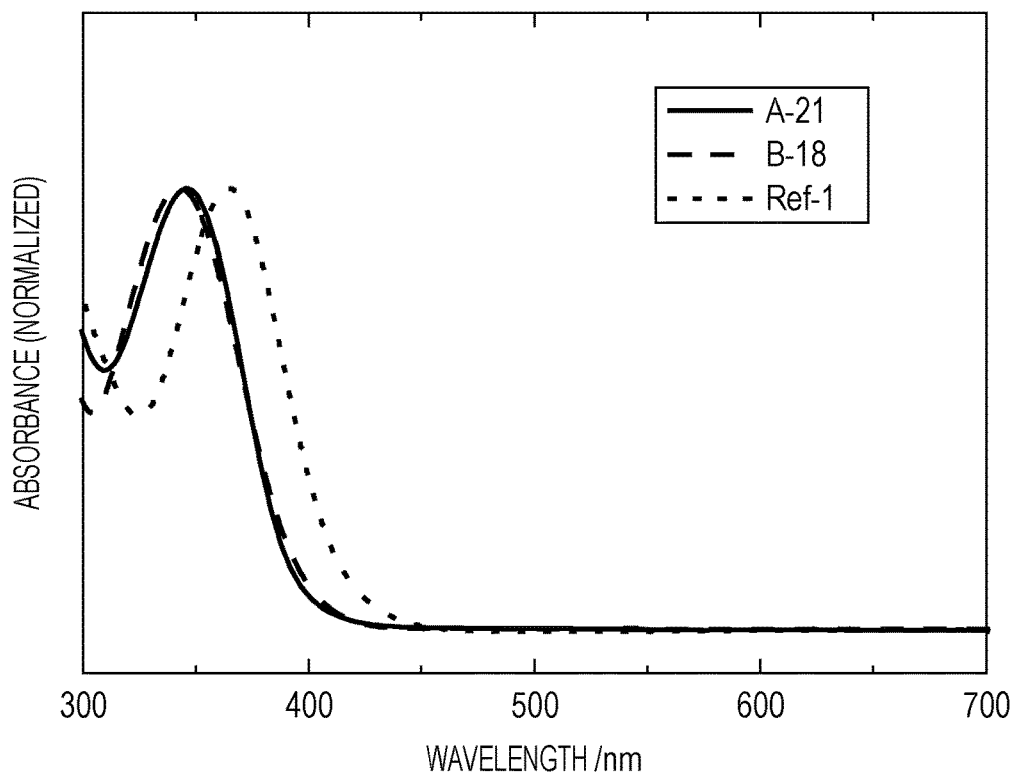
FIG. 5 is a graph showing ultraviolet-visible absorption spectra in a neutral state in Example 3.

In this example, the transparency in a neutral state of each of the example compound A-21 of Example 1, the example compound B-18 of Example 2, and the comparative compound Ref-1 of Comparative Example 1 will be described with reference to FIG. 5. FIG. 5 shows the measurement result of the absorption spectrum of each compound. The absorption spectrum was measured by an ultraviolet-visible photospectrometer (V-560 manufactured by JASCO Corp.) using a solution in which each of the example compound A-21 of Example 1, the example compound B-18 of Example 2, and the comparative compound Ref-1 of Comparative Example 1 was dissolved in acetonitrile.

Since the example compound A-21 and the example compound B-18 were each an approximately colorless solid by view observation, the absorption spectra thereof each had an absorption peak in a ultraviolet region, and the absorption edges were each located at approximately 420 nm. The example compound A-21 and the example compound B-18 each had no absorption in the entire visible light region and were materials having an improved transparency as compared to that in the past. On the other hand, the comparative compound Ref-1 was a pale reddish-brown solid by view observation, and the absorption edge of the absorption peak was located at approximately 460 nm.

The results described above indicate that the example compound A-21 and the example compound B-18, in each of which alkoxy groups are provided as the substituents at the ortho positions of each phenyl group, have a high transparency in a neutral state as compared to that of the comparative compound Ref-1.

Example 4

<Evaluation of Electrochromic Characteristics>

Measurement of absorption spectrum in an oxidized (colored) state was performed on each of the example compound A-21 of Example 1, the example compound B-18 of Example 2, and the comparative compound Ref-1 of Comparative Example 1.

The measurement of absorption spectrum was performed using a solution in which each of the above compounds was dissolved ($5.0 \times 10^{-4}$ mol/L) in a propylene carbonate solution containing tetrabutylammonium perchlorate salt at a concentration of 0.1 mol/L as a supporting electrolyte. After the solution thus prepared was received in a glass cell having a light path length of 1 mm, a mesh-shaped platinum electrode (working electrode) and a wire-shaped platinum electrode (counter electrode) are disposed in a predetermined manner, and a reference electrode RE (Ag/Ag$^+$) was arranged, the measurement was performed. Constant potential oxidation was performed on this solution at a potential equal to or more than the oxidation potential of the compound, and light passing through the mesh electrode was used for the measurement. The application of a drive voltage was performed by a potentiostat (Cell Test 1470E) manufactured by Solartron, and for the spectroscopic measurement, a spectral device (USB2000-UV-VIS) manufactured by Ocean OPtics was used.

The wavelength (absorption wavelength) $\lambda_{max}$ of an absorption peak in a colored state (oxidized state) and the wavelength of the absorption edge in a decolored state (neutral state) of the above Example 3 are collectively shown in Table 2.

TABLE 2

| Compound | Wavelength of Absorption Edge (nm) | Absorption Wavelength $\lambda_{max}$ (nm) |
|---|---|---|
| A-21 | 420 | 560 |
| B-18 | 420 | 546 |
| Ref-1 | 460 | 535 |

Color species produced by oxidation has an absorption in a visible light region. However, the example compounds A-21 and B-18 each have an absorption peak in a long wavelength side in an oxidized state as compared to that of the comparative compound Ref-1. This oxidized colored state was again returned to a colorless transparent state by reduction, so that reversible electrochromic characteristics in association with oxidation and reduction were confirmed.

From Examples 3 and 4, since the neutral absorption of each of the example compounds A-21 and B-18 was shifted to a short wavelength side as compared to that of the comparative compound Ref-1, the transparency was improved, and in addition, in an oxidized colored state, compared to the compound Ref-1, the absorption was observed in a long wavelength region of 540 nm or more.

Example 5

<Formation of Electrochromic Element and Element Drive>

Next, the example compound A-21 as an anodic EC material and a cathodic EC compound W-1 having the following structure as a cathodic EC material were each dissolved in propylene carbonate to have a concentration of 100.0 mM, so that an EC solution was prepared.

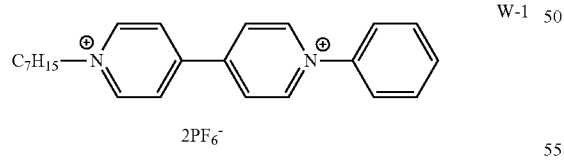

Next, the EC element shown in FIG. 2 was formed by the following method. The two substrates 10 each provided with a transparent electrically conductive film (ITO) as the electrode 11 were prepared and were then disposed so that the electrically conductive surfaces (surfaces on each of which the electrode 11 was provided) faced each other with a predetermined space interposed therebetween. As the substrate 10, a glass substrate was used. Subsequently, the two substrates 10 were sealed along an element peripheral portion with an epoxy adhesive except for an injection port through which the solution was to be injected to form the EC layer 12, so that an empty cell having the injection port was formed. In this case, the distance between the electrodes 11 was adjusted by the sealing material 13 used as a spacer which was formed by changing the thickness of a film or the diameter of each bead.

Into the cell of the EC element formed as described above, the EC solution was injected by a vacuum injection method through the opening portion of the cell, so that the EC layer 12 was formed. Furthermore, the opening portion of the cell was sealed with an epoxy resin, so that the EC element was formed.

When a voltage of 0.7 V was applied to this EC element, an absorption ($\lambda \sim 560$ nm) derived from an oxidizing species of the example compound A-21 and an absorption ($\lambda \sim 615$ nm) derived from a reducing species of the cathodic EC compound W-1 were obtained, so that the organic EC element was colored. When 0 V was applied, the organic EC element was decolored, so that reversible coloration/decoloration occurs. The change in transmittance spectrum of the EC element of this embodiment in association with this voltage application is shown in FIG. 6.

Figure 6:
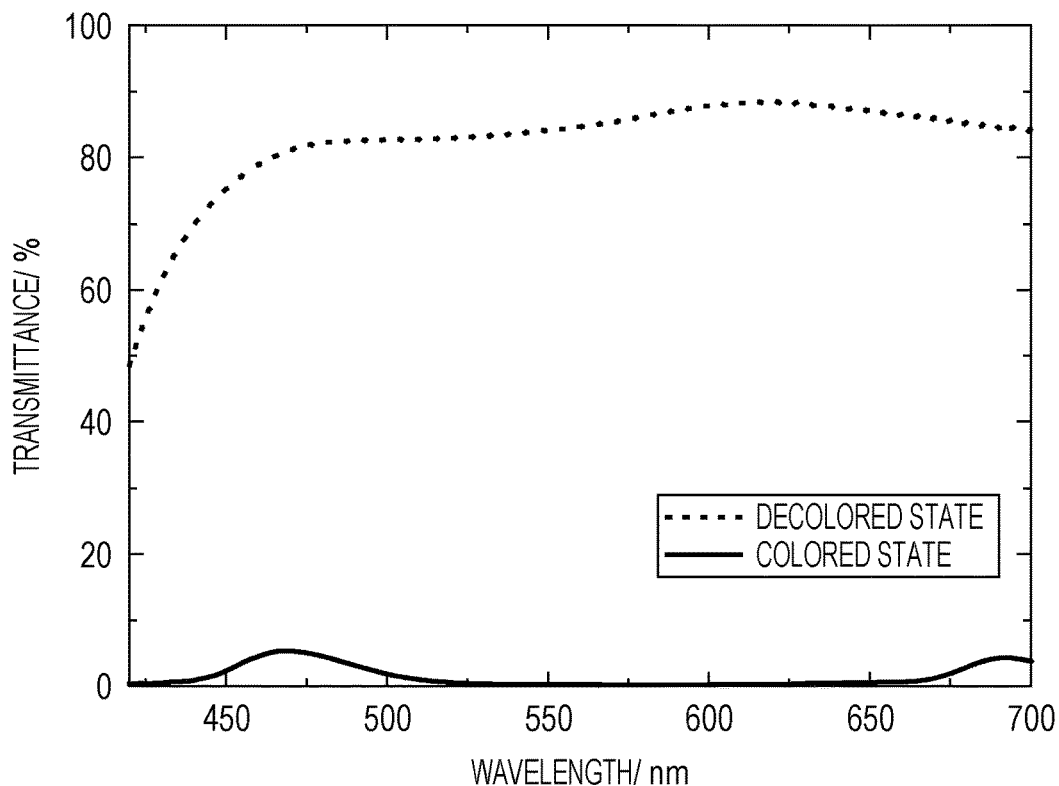
FIG. 6 is a graph showing transmittance spectra obtained when an electrochromic element of Example 5 is colored and decolored.

As shown in FIG. 6, the organic EC element using the example compound A-21 of Example 1 was confirmed that the change in transmittance in a long wavelength region was observed in a colored state in association with the voltage application.

Example 6

<Synthesis of Example Compound A-3>

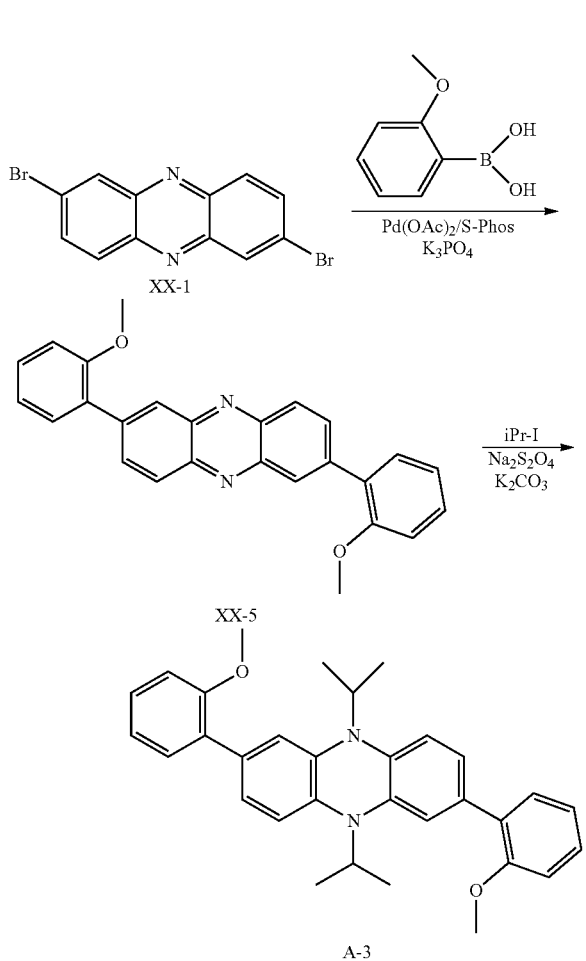

The example compound A-3 can be synthesized, for example, by the following procedure. First, a compound XX-5 is synthesized. In a 50-ml reaction chamber, 507 mg (1.5 mmol) of the compound XX-1 and 638 mg (4.5 mmol) of 2-methoxyphenylboronic acid were mixed in a mixed solvent of toluene/1,4-dioxane (6 ml/6 ml), and dissolved oxygen was removed by nitrogen. Next, 13.5 mg (0.06 mmol) of Pd(OAc)$_2$, 61.6 mg (0.15 mmol) of 2-dicyclohexylphosphino-2',6'-dimethoxybiphenyl (S-Phos), and 1.72 g (7.5 mmol) of tripotassium phosphate were added in a nitrogen atmosphere, and a reaction was performed by heating and refluxing at 100° C. for 6 hours.

After the reaction solution was cooled to room temperature, a powder precipitated by reduced-pressure condensation was purified by recrystallization, so that a yellow solid compound XX-5 was obtained (265 mg, yield: 45%).

Subsequently, the example compound A-3 is synthesized. In a 50-ml reaction chamber, 155 mg (0.40 mmol) of the compound XX-5 and 1.34 g (7.9 mmol) of 2-iodopropane were mixed in acetonitrile (5 ml), and dissolved oxygen was removed by nitrogen. Next, a sodium hydrosulfite (344 mg, 1.98 mmol) solution (1.6 ml) and a potassium carbonate (327 mg, 2.37 mmol) solution (0.7 ml) were added, and a reaction was performed by heating and refluxing at 90° C. for 9 hours.

After the reaction solution was cooled to room temperature and was then condensed at a reduced pressure, separation and purification were performed by a silica gel chromatography (mobile phase: hexane/toluene), so that a solid example compound A-3 was obtained (175 mg, yield: 92%).

The structure identification of the compound thus obtained was performed by NMR measurement. As a result, since the ratio of peak integration values well coincided with that of the structure, so that the obtained compound was identified as the example compound A-3. The measurement result of the NMR spectrum is shown below.

$^1$H-NMR (deuterated acetone) δ(ppm): 7.35-7.25 (m, 4H), 7.09-7.01 (m, 4H), 6.99 (t, 2H), 6.91 (dd, 2H), 6.80 (d, 2H), 4.18 (sep, 2H), 3.82 (s, 6H), 1.53 (d, 12H).

Example 7

<Synthesis of Example Compound A-25>

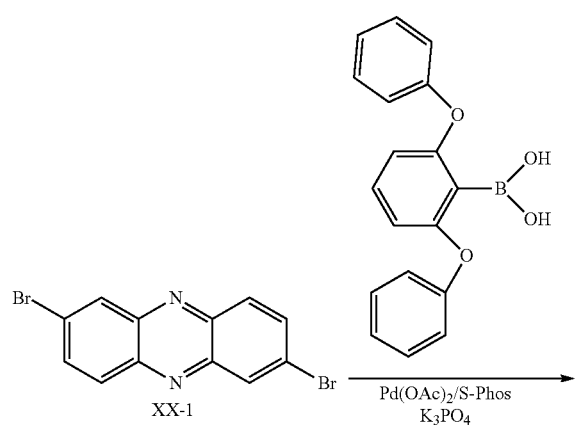

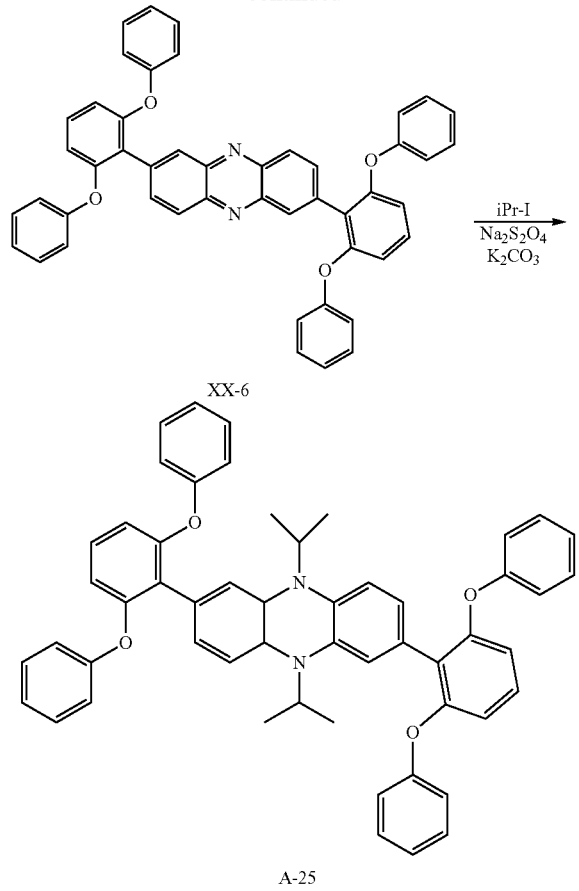

The example compound A-25 can be synthesized, for example, by the following procedure. First, a compound XX-6 is synthesized. In a 50-ml reaction chamber, 507 mg (1.5 mmol) of the compound XX-1 and 1.38 g (4.5 mmol) of 2,6-diphenoxyphenylboronic acid were mixed in a mixed solvent of toluene/1,4-dioxane (6 ml/6 ml), and dissolved oxygen was removed by nitrogen. Next, 13.5 mg (0.06 mmol) of Pd(OAc)$_2$, 61.6 mg (0.15 mmol) of 2-dicyclohexylphosphino-2',6'-dimethoxybiphenyl (S-Phos), and 1.72 g (7.5 mmol) of tripotassium phosphate were added in a nitrogen atmosphere, and a reaction was performed by heating and refluxing at 100° C. for 4 hours.

After the reaction solution was cooled to room temperature, a powder precipitated by reduced-pressure condensation was purified by recrystallization, so that a yellow solid compound XX-6 was obtained (650 mg, yield: 62%).

Subsequently, the example compound A-25 is synthesized. In a 50-ml reaction chamber, 350 mg (0.50 mmol) of the compound XX-6 and 2.55 g (15.0 mmol) of 2-iodopropane were mixed in a mixed solvent of acetonitrile/water (10 ml/1 ml), and dissolved oxygen was removed by nitrogen. Next, 435 mg (2.5 mmol) of sodium hydrosulfite and 415 mg (3.0 mmol) of potassium carbonate were added in a nitrogen atmosphere, and a reaction was performed by heating and refluxing at 90° C. for 10 hours.

After the reaction solution was cooled to room temperature and was then condensed at a reduced pressure, separation and purification were performed by a silica gel chromatography (mobile phase: hexane/toluene), so that a solid example compound A-25 was obtained (80 mg, yield: 20%).

The structure identification of the compound thus obtained was performed by NMR measurement. As a result, the ratio of peak integration values well coincided with that of the structure, so that the obtained compound was identified as the example compound A-25. The measurement result of the NMR spectrum is shown below.

$^1$H-NMR (deuterated acetone) δ(ppm): 7.41-7.32 (m, 10H), 7.29 (t, 2H), 7.08 (t, 4H), 6.98 (d, 8H), 6.87 (t, 4H), 6.83 (dd, 2H), 6.72 (d, 2H), 6.61 (d, 2H), 3.78 (sep, 2H), 1.28 (d, 12H).

Example 8

<Synthesis of Example Compound B-9>

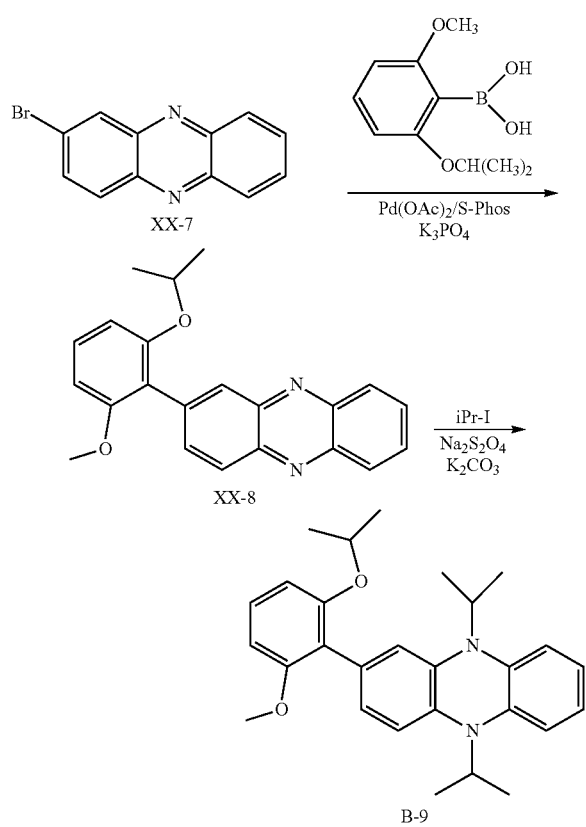

The example compound B-9 can be synthesized, for example, by the following procedure. First, a compound XX-8 is synthesized. In a 50-ml reaction chamber, 518 mg (2.0 mmol) of a compound XX-7 and 462 mg (2.2 mmol) of 2-isoporopoxy-6-methoxyphenylboronic acid were mixed in a mixed solvent of toluene/1,4-dioxane (7 ml/7 ml), and dissolved oxygen was removed by nitrogen. Next, 18.0 mg (0.08 mmol) of Pd(OAc)$_2$, 82.1 mg (0.2 mmol) of 2-dicyclohexylphosphino-2',6'-dimethoxybiphenyl (S-Phos), and 2.30 g (10.0 mmol) of tripotassium phosphate were added in a nitrogen atmosphere, and a reaction was performed by heating and refluxing at 100° C. for 9 hours.

After the reaction solution was cooled to room temperature and was then condensed at a reduce pressure, separation and purification were performed by a silica gel chromatography (mobile phase: hexane/chloroform), so that a yellow solid compound XX-8 was obtained (654 mg, yield: 95%).

Subsequently, the example compound B-9 is synthesized. In a 50-ml reaction chamber, 516 mg (1.5 mmol) of the compound XX-8 and 5.10 g (30 mmol) of 2-iodopropane were mixed in a mixed solvent of acetonitrile/water (10 ml/1 ml), and dissolved oxygen was removed by nitrogen. Next, 1.30 g (7.5 mmol) of sodium hydrosulfite and 1.24 g (9.0 mmol) of potassium carbonate were added in a nitrogen atmosphere, and a reaction was performed by heating and refluxing at 90° C. for 9 hours. After the reaction solution was cooled to room temperature and was then condensed at a reduced pressure, separation and purification were performed by a silica gel chromatography (mobile phase: hexane/toluene), so that a solid example compound B-9 was obtained (226 mg, yield: 35%).

The structure identification of the compound thus obtained was performed by NMR measurement. As a result, the ratio of peak integration values well coincided with that of the structure, so that the obtained compound was identified as the example compound B-9. The measurement result of the NMR spectrum is shown below.

$^1$H-NMR (deuterated acetone) δ(ppm): 7.19 (t, 1H), 6.86-6.66 (m, 9H), 4.42 (sep, 1H), 4.10 (sep, 1H), 4.01 (sep, 1H), 3.65 (s, 3H), 1.52 (d, 6H), 1.43 (d, 6H), 1.17 (d, 6H).

Example 9

<Evaluation of Neutral Transparency and Electrochromic Characteristics>

As was the case of Examples 3 and 4, the measurement of the absorption spectra in a decolored state (neutral state) and a colored state (oxidized state) was performed on each of the example compound A-3 of Example 6, the example compound A-25 of Example 7, and the example compound B-9 of Example 8. The wavelength of the absorption edge in a decolored state (neutral state) and the wavelength (absorption wavelength) $\lambda_{max}$ of the absorption peak in a colored state (oxidized state) are shown in Table 3.

TABLE 3

| Compound | Neutral Absorption Edge (nm) | Color Absorption Wavelength $\lambda_{max}$ (nm) |
|---|---|---|
| A-3 | 440 | 560 |
| A-25 | 430 | 542 |
| B-9 | 420 | 542 |

The example compounds A-3, A-25, and B-9 each had in an oxidized state, an absorption peak in a long wavelength region as compared to that of the comparative compound Ref-1 shown in Table 2. This oxidized colored state was again returned to a colorless transparent state by reduction, so that reversible electrochromic characteristics in association with oxidation and reduction were confirmed.

From Example 9, compared to the comparative compound Ref-1, the neutral absorption of each of the example compounds A-3, A-25 and B-9 was shifted to a short wavelength side, and the transparency thereof was improved, and furthermore, in an oxidized colored state, the example compounds described above each had an absorption in a long wavelength region of 540 nm or more as compared to that of the compound Ref-1.

Example 10

<Synthesis of Example Compound C-6>

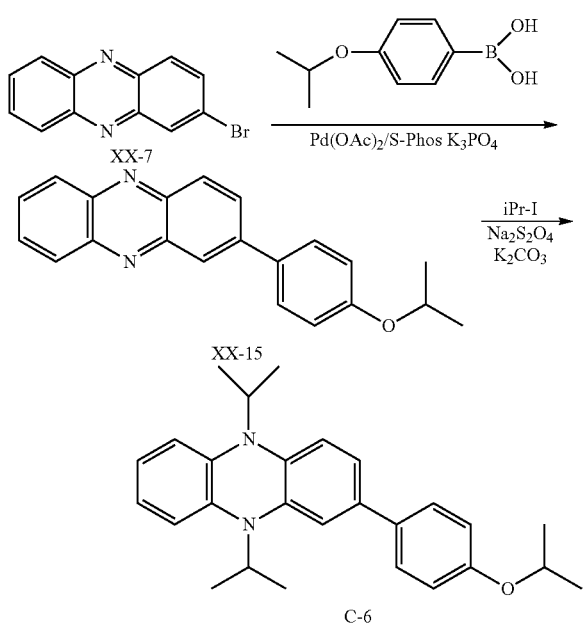

The example compound C-6 can be synthesized, for example, by the following procedure. First, a compound XX-15 is synthesized. In a 50-ml reaction chamber, 518 mg (2.0 mmol) of a compound XX-7 and 450 mg (2.5 mmol) of 4-isopropoxyphenylboronic acid were mixed in a mixed solvent of toluene/1,4-dioxane (7 ml/7 ml), and dissolved oxygen was removed by nitrogen. In addition, the compound XX-7 was a compound synthesized in accordance with Tetrahedron Letters, 52, 6484 (2011).

Next, 18.0 mg (0.08 mmol) of Pd(OAc)$_2$, 82.1 mg (0.20 mmol) of 2-dicyclohexylphosphino-2',6'-dimethoxybiphenyl (S-Phos), and 2.30 g (10.0 mmol) of tripotassium phosphate were added in a nitrogen atmosphere, and a reaction was performed by heating and refluxing at 100° C. for 3 hours.

After the reaction solution was cooled to room temperature and was then condensed at a reduce pressure, separation and purification were performed by a silica gel chromatography (mobile phase: hexane/chloroform), so that a yellow solid compound XX-15 was obtained (565 mg, yield: 90%).

Subsequently, the example compound C-6 is synthesized. In a 50-ml reaction chamber, 384 mg (1.22 mmol) of the compound XX-15 and 4.15 g (24.4 mmol) of 2-iodopropane were mixed in a mixed solvent of acetonitrile/water (18 ml/8 ml), and dissolved oxygen was removed by nitrogen. Next, 1.25 g (6.1 mmol) of sodium hydrosulfite and 1.01 g (7.3 mmol) of potassium carbonate were added in a nitrogen atmosphere, and a reaction was performed by heating and refluxing at 90° C. for 9 hours.

After the reaction solution was cooled to room temperature and was then condensed at a reduced pressure, separation and purification were performed by a silica gel chromatography (mobile phase: hexane/toluene), so that a solid example compound C-6 was obtained (390 mg, yield: 80%).

The structure identification of the compound thus obtained was performed by NMR measurement. As a result, the ratio of peak integration values well coincided with that of the structure, so that the obtained compound was identified as the example compound C-6. The measurement result of the NMR spectrum is shown below.

$^1$H-NMR (deuterated acetone) δ(ppm): 7.49 (d, 2H), 7.04-6.91 (m, 4H), 6.86-6.72 (m, 5H), 4.65 (sep, 1H), 4.12 (sep, 2H), 1.56 (d, 12H), 1.32 (d, 6H).

Example 11

<Synthesis of Example Compound D-2>

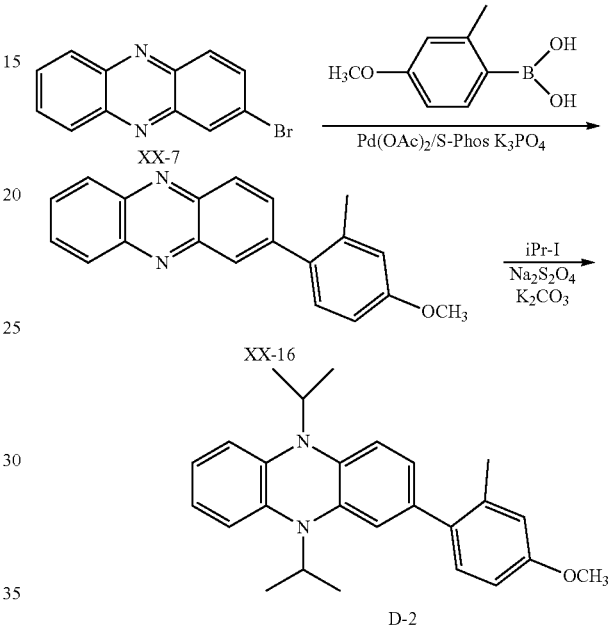

The example compound D-2 can be synthesized, for example, by the following procedure. First, a compound XX-16 is synthesized. In a 50-ml reaction chamber, 518 mg (2.00 mmol) of the compound XX-7 and 498 mg (3.0 mmol) of 4-metoxy-2-methylphenylboronic acid were mixed in a mixed solvent of toluene/1,4-dioxane (7 ml/7 ml), and dissolved oxygen was removed by nitrogen. Next, 18.0 mg (0.08 mmol) of Pd(OAc)$_2$, 82.1 mg (0.20 mmol) of 2-dicyclohexylphosphino-2',6'-dimethoxybiphenyl (S-Phos), and 2.30 g (10.0 mmol) of tripotassium phosphate were added in a nitrogen atmosphere, and a reaction was performed by heating and refluxing at 100° C. for 5 hours.

After the reaction solution was cooled to room temperature and was then condensed at a reduce pressure, separation and purification were performed by a silica gel chromatography (mobile phase: hexane/chloroform), so that a yellow solid compound XX-16 was obtained (550 mg, yield: 91%).

Subsequently, the example compound D-2 is synthesized. In a 50-ml reaction chamber, 550 mg (1.83 mmol) of the compound XX-16 and 6.23 g (36.6 mmol) of 2-iodopropane were mixed in a mixed solvent of acetonitrile/water (20 ml/10 ml), and dissolved oxygen was removed by nitrogen. Next, 1.59 g (9.15 mmol) of sodium hydrosulfite and 1.52 g (11.0 mmol) of potassium carbonate were added in a nitrogen atmosphere, and a reaction was performed by heating and refluxing at 90° C. for 10 hours.

After the reaction solution was cooled to room temperature and was then condensed at a reduced pressure, separation and purification were performed by a silica gel chromatography (mobile phase: hexane/toluene), so that a solid example compound D-2 was obtained (665 mg, yield: 94%).

According to the result of NMR measurement, the ratio of peak integration values well coincided with that of the structure, so that the obtained compound was identified as the example compound D-2. The measurement result of the NMR spectrum is shown below.

$^1$H-NMR (deuterated acetone) δ(ppm): 7.12 (t, 1H), 6.84-6.74 (m, 7H), 6.70 (dd, 1H), 6.66 (d, 1H), 4.09 (sep, 2H), 3.79 (s, 3H), 2.26 (s, 3H), 1.50 (d, 6H), 1.46 (d, 6H).

Example 12

<Synthesis of Example Compound F-2>

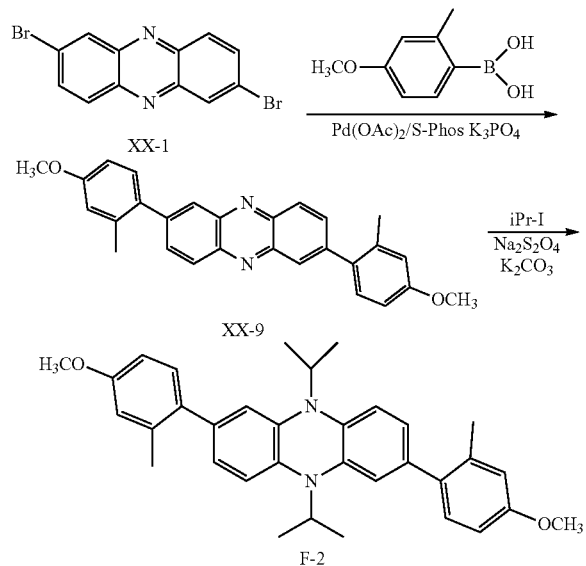

The example compound F-2 can be synthesized, for example, by the following procedure. First, a compound XX-9 is synthesized. In a 50-ml reaction chamber, 507 mg (1.50 mmol) of a compound XX-1 and 747 mg (4.5 mmol) of 4-metoxy-2-methylphenylboronic acid were mixed in a mixed solvent of toluene/1,4-dioxane (7 ml/7 ml), and dissolved oxygen was removed by nitrogen. Next, 13.5 mg (0.06 mmol) of Pd(OAc)$_2$, 61.6 mg (0.15 mmol) of 2-dicyclohexylphosphino-2',6'-dimethoxybiphenyl (S-Phos), and 1.72 g (7.5 mmol) of tripotassium phosphate were added in a nitrogen atmosphere, and a reaction was performed by heating and refluxing at 100° C. for 6 hours.

After the reaction solution was cooled to room temperature and was then condensed at a reduce pressure, separation and purification were performed by a silica gel chromatography (mobile phase: hexane/chloroform), so that a yellow solid compound XX-9 was obtained (478 mg, yield: 76%).

Subsequently, the example compound F-2 is synthesized. In a 50-ml reaction chamber, 255 mg (0.61 mmol) of the compound XX-9 and 2.06 g (12.1 mmol) of 2-iodopropane were mixed in a mixed solvent of acetonitrile/water (10 ml/4 ml), and dissolved oxygen was removed by nitrogen. Next, 528 mg (3.03 mmol) of sodium hydrosulfite and 503 mg (3.64 mmol) of potassium carbonate were added in a nitrogen atmosphere, and a reaction was performed by heating and refluxing at 90° C. for 9 hours.

After the reaction solution was cooled to room temperature and was then condensed at a reduced pressure, separation and purification were performed by a silica gel chromatography (mobile phase: hexane/toluene), so that a solid example compound F-2 was obtained (130 mg, yield: 42%).

According to the result of NMR measurement, the ratio of peak integration values well coincided with that of the structure, so that the obtained compound was identified as the example compound F-2. The measurement result of the NMR spectrum is shown below.

$^1$H-NMR (deuterated acetone) δ(ppm): 7.12 (d, 2H), 6.86-6.81 (m, 4H), 6.79 (dd, 2H), 6.73-6.67 (m, 4H), 4.16 (sep, 2H), 3.79 (s, 6H), 2.28 (s, 6H), 1.52 (d, 12H).

Comparative Example 2

As Comparative Example 2, the comparative compound Ref-3 which was the known EC compound described above was used. The comparative compound Ref-3 was a phenazine derivative substituted by a phenyl group having no alkoxy substituent at the para position thereof.

Example 13

<Neutral Transparency>

Figure 8:
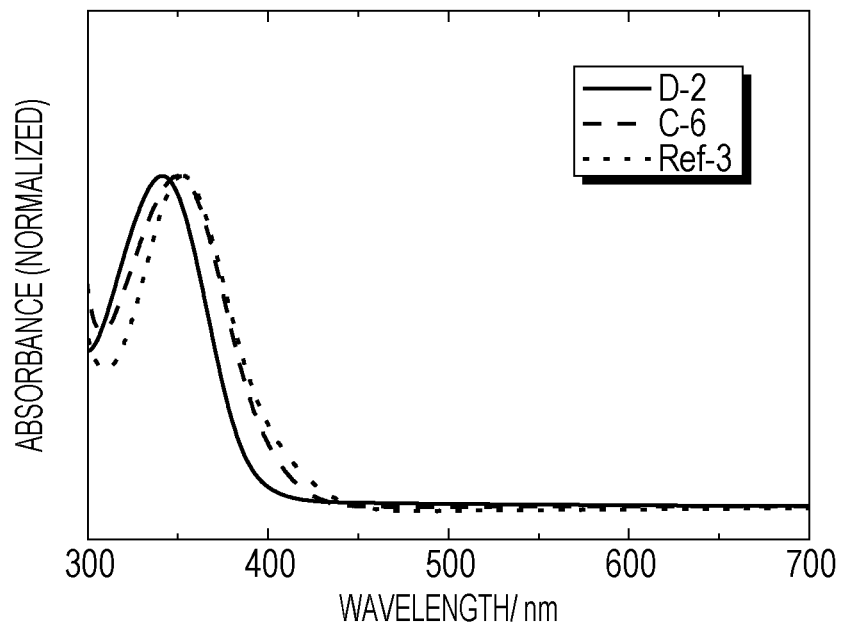
FIG. 8 is a graph showing ultraviolet-visible absorption spectra in a neutral state in Example 13.

In this example, the transparency in a neutral state of each of the example compound C-6 of Example 10, the example compound D-2 of Example 11, and the comparative compound Ref-3 of Comparative Example 2 will be described with reference to FIG. 8. FIG. 8 shows the measurement result of the absorption spectrum of each compound. The absorption spectrum was measured by a method similar to that of Example 3.

The comparative compound Ref-3 and the example compound C-6 were each a deep yellow solid by visual observation, and the absorption edges of the absorption peaks thereof were each located at approximately 450 nm. On the other hand, since the example compound D-2 was an approximately colorless solid by visual observation, as shown in FIG. 8, the absorption was shifted to a shorter wavelength side as compared to that of each of the comparative compound Ref-3 and the example compound C-6, and the absorption edge thereof was also located at approximately 410 nm. The example compound D-2 has no absorption over the entire visible light region and is a material having an improved transparency as compared to that in the past. In addition, the absorption edge of the example compound F-2 is located at 420 nm, and as is the example compound D-2, the example compound F-2 has no absorption over the entire visible light region and is a material having an improved transparency as compared to that in the past.

The wavelength of the absorption edge in a decolored state (neutral state) is shown in Table 4.

TABLE 4

| Compound | Wavelength of Absorption Edge in Decolored State (Neutral State) (nm) |
| --- | --- |
| C-6 | 445 |
| D-2 | 410 |
| F-2 | 420 |
| Ref-3 | 450 |

The above results indicate that the example compound D-2 and the example compound F-2, each of which has a substituent on one of the ortho positions of each phenyl group, has a high transparency in a neutral state as compared to that of the comparative compound Ref-3.

Example 14

<Evaluation of Electrochromic Characteristics>

The absorption spectra in an oxidized state (colored state) of the example compound C-6 of Example 10, the example compound D-2 of Example 11, the example compound F-2 of Example 12, and the comparative compound Ref-3 of Comparative Example 2 were measured. The measurement of the absorption spectra was performed by a method similar to that of Example 4.

The wavelength (absorption wavelength) $\lambda_{max}$ of the absorption peak in a colored state (oxidized state) is shown in Table 5.

TABLE 5

| Compound | Absorption Wavelength in Colored State $\lambda_{max}$ (nm) |
|---|---|
| C-6 | 572 |
| D-2 | 553 |
| F-2 | 567 |
| Ref-3 | 496 |

The color species produced by oxidation each have an absorption in a visible wavelength region. However, the example compounds C-6, D-2, and F-2 each having an alkoxy group at the para position of each phenyl group, which is an outer portion of the molecule, each had an absorption peak in a long wavelength region in an oxidized state as compared to that of the comparative compound Ref-3 having no alkoxy group at the para position of the phenyl group which is an outer portion of the molecule. This oxidized colored state was again returned to a colorless transparent state by reduction, so that the reversible electrochromic characteristics in association with oxidation and reduction were confirmed.

From Examples 13 and 14, it was found that the example compound C-6, the example compound D-2, and the example compound F-2 each having an alkoxy group at the para position of each phenyl group, which is an outer portion of the molecule, each had an absorption in a long wavelength region of 540 nm or more in an oxidized colored state as compared to that of the comparative compound Ref-3, and that in particular, in the example compound D-2 and the example compound F-2, each of which also has the substituent at the ortho position of each phenyl group, the neutral absorption is shifted to a short wavelength side, so that the transparency in a decolored state and the long wavelength absorption in a colored state can be simultaneously satisfied.

Example 15

<Formation of Electrochromic Element and Element Drive>

An EC element 15 including the EC layer 12 which contained the example compound D-2 was formed. First, the example compound D-2 having an EC property as an anodic EC material and a cathodic EC compound W-2 having the following structure as a cathodic EC material were each dissolved in propylene carbonate to have a concentration of 100.0 mM, so that an EC solution was prepared.

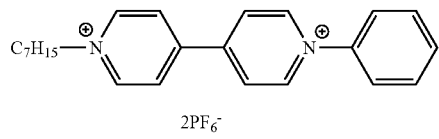

Next, by a method similar to that of Example 5, an empty cell was formed, and the EC solution of this example was filled in the empty cell thus formed through an opening portion thereof by a vacuum injection method, so that the EC layer 12 was formed. Furthermore, the opening portion was sealed with an epoxy resin, so that the EC element 15 was formed.

When a voltage of 0.7 V was applied to this EC element 15, an absorption ($\lambda$~550 nm) derived from the oxidizing species of the example compound D-2 and an absorption ($\lambda$~615 nm) derived from the reducing species of the cathodic EC compound W-2 were obtained, and the EC element 15 was colored. The EC element 15 was decolored when 0 V was applied thereto, so that the reversible coloration/decoloration occurred. The change in transmittance spectrum of the EC element of this example in association with the voltage application is shown in FIG. 9.

Figure 9:
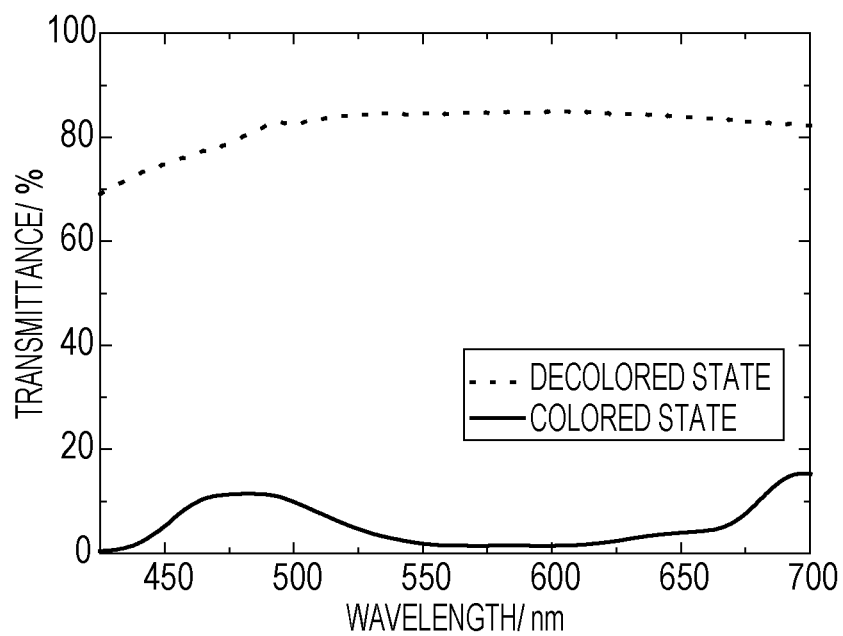
FIG. 9 is a graph showing the transmittance spectra obtained when an electrochromic element of Example 15 is colored and decolored.

As shown in FIG. 9, the EC element 15 using the example compound D-2 was confirmed that the change in transmittance in a long wavelength region was observed in a colored state in association with the voltage application.

Example 16

<Synthesis of Example Compound F-14>

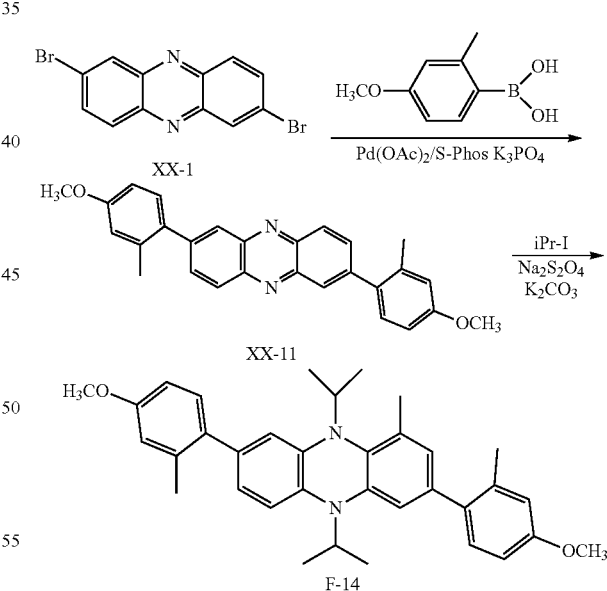

First, a compound XX-11 was synthesized. In a 50-ml reaction chamber, 342 mg (0.97 mmol) of a compound XX-1 and 484 mg (2.91 mmol) of 4-metoxy-2-methylphenylboronic acid were mixed in a mixed solvent of toluene/1,4-dioxane (5 ml/5 ml), and dissolved oxygen was removed by nitrogen.

Next, 8.8 mg (0.04 mmol) of Pd(OAc)$_2$, 40.0 mg (0.097 mmol) of S-Phos, and 1.12 g (4.9 mmol) of tripotassium phosphate were added in a nitrogen atmosphere, and a reaction was performed by heating and refluxing at 100° C. for 3 hours. After the reaction solution was cooled to room temperature and was then condensed at a reduce pressure, separation and purification were performed by a silica gel chromatography (mobile phase: hexane/chloroform), so that a yellow solid compound XX-11 was obtained (410 mg, yield: 96%).

Subsequently, an example compound F-14 is synthesized. In a 50-ml reaction chamber, 391 mg (0.90 mmol) of the compound XX-11 and 3.06 g (18.0 mmol) of 2-iodopropane were mixed in a mixed solvent of acetonitrile/water (20 ml/10 ml), and dissolved oxygen was removed by nitrogen. Next, 920 mg (4.5 mmol) of sodium hydrosulfite and 750 mg (5.4 mmol) of potassium carbonate were added in a nitrogen atmosphere, and a reaction was performed by heating and refluxing at 90° C. for 8 hours. After the reaction solution was cooled to room temperature and was then condensed at a reduced pressure, separation and purification were performed by a silica gel chromatography (mobile phase: hexane/toluene), so that a solid example compound F-14 was obtained (111 mg, yield: 24%).

According to the result of NMR measurement, the ratio of peak integration values well coincided with that of the structure, so that the obtained compound was identified as the example compound F-14. The measurement result of the NMR spectrum is shown below.

$^1$H-NMR (deuterated acetone) δ(ppm): 7.15-7.05 (m, 3H), 6.98 (dd, 1H), 6.90-6.70 (m, 7H), 4.48 (sep, 1H), 3.81 (s, 6H), 3.33 (sep, 1H), 2.35 (s, 3H), 2.28 (s, 6H), 1.62 (d, 6H), 1.23 (d, 6H).

Example 17

<Synthesis of Example Compound B-30>

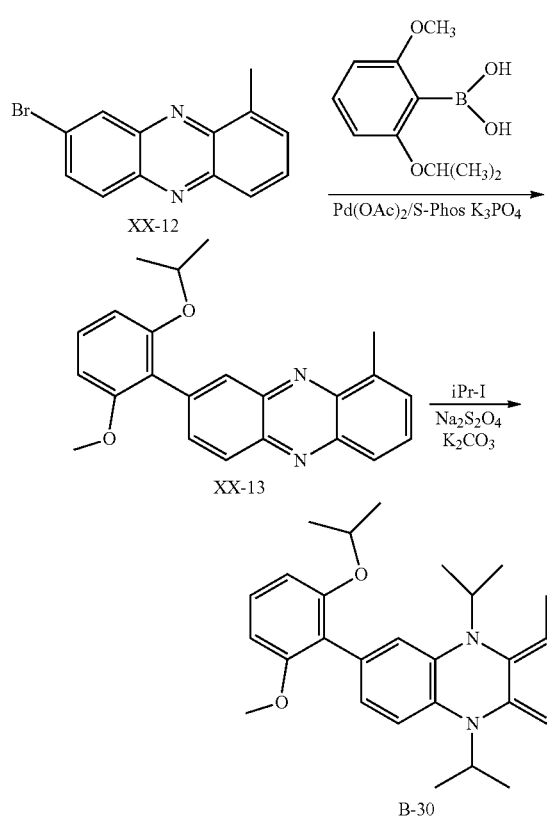

First, a compound XX-13 is synthesized. In a 50-ml reaction chamber, 395 mg (1.45 mmol) of a compound XX-12 and 456 mg (2.17 mmol) of 2-isopropoxy-6-methoxyphenylboronic acid were mixed in a mixed solvent of toluene/1,4-dioxane (5 ml/5 ml), and dissolved oxygen was removed by nitrogen.

Next, 13.0 mg (0.06 mmol) of Pd(OAc)$_2$, 59.0 mg (0.15 mmol) of S-Phos, and 1.66 g (7.2 mmol) of tripotassium phosphate were added in a nitrogen atmosphere, and a reaction was performed by heating and refluxing at 100° C. for 4 hours. After the reaction solution was cooled to room temperature and was then condensed at a reduce pressure, separation and purification were performed by a silica gel chromatography (mobile phase: hexane/chloroform), so that a yellow solid compound XX-13 was obtained (510 mg, yield: 98%).

Subsequently, an example compound B-30 is synthesized. In a 50-ml reaction chamber, 510 mg (1.42 mmol) of the compound XX-13 and 5.07 g (29.8 mmol) of 2-iodopropane were mixed in a mixed solvent of acetonitrile/water (20 ml/8 ml), and dissolved oxygen was removed by nitrogen. Next, 1.53 g (7.45 mmol) of sodium hydrosulfite and 1.24 g (8.94 mmol) of potassium carbonate were added in a nitrogen atmosphere, and a reaction was performed by heating and refluxing at 90° C. for 9 hours. After the reaction solution was cooled to room temperature and was then condensed at a reduced pressure, separation and purification were performed by a silica gel chromatography (mobile phase: hexane/toluene), so that a solid example compound B-30 was obtained (350 mg, yield: 54%).

According to the result of NMR measurement, the ratio of peak integration values well coincided with that of the structure, so that the obtained compound was identified as the example compound B-30. The measurement result of the NMR spectrum is shown below.

$^1$H-NMR (deuterated acetone) δ(ppm): 7.20 (t, 1H), 6.99-6.83 (m, 5H), 6.74 (d, 1H), 6.72-6.65 (m, 2H), 4.45 (sep, 2H), 3.69 (s, 3H), 3.25 (sep, 1H), 2.28 (s, 3H), 1.62 (d, 6H), 1.42-1.02 (d, br, 12H).

Example 18

<Synthesis of Example Compound A-40>

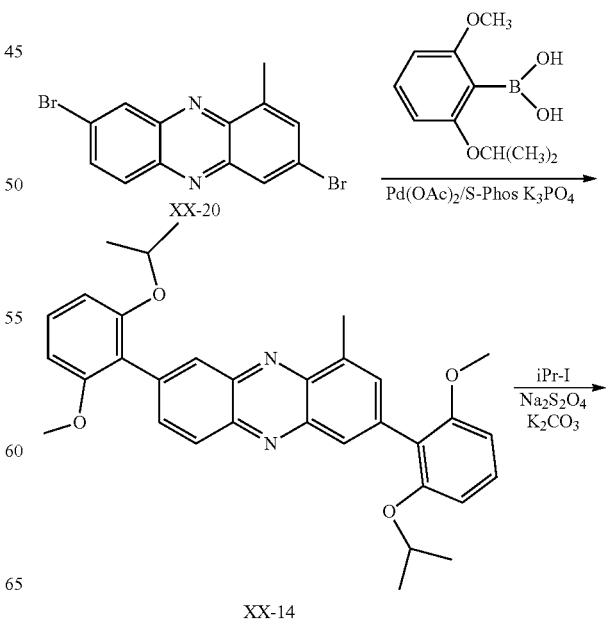

-continued

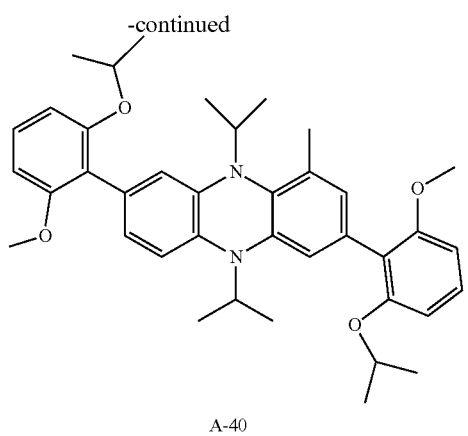

A-40

First, a compound XX-14 is synthesized. In a 50-ml reaction chamber, 704 mg (2.0 mmol) of a compound XX-20 and 1.26 g (6.0 mmol) of 2-isopropoxy-6-methoxyphenylboronic acid were mixed in a mixed solvent of toluene/1,4-dioxane (8 ml/8 ml), and dissolved oxygen was removed by nitrogen.

Next, 18.0 mg (0.08 mmol) of Pd(OAc)$_2$, 82.1 mg (0.20 mmol) of S-Phos, and 2.30 g (10.0 mmol) of tripotassium phosphate were added in a nitrogen atmosphere, and a reaction was performed by heating and refluxing at 110° C. for 6 hours. After the reaction solution was cooled to room temperature and was then condensed at a reduce pressure, separation and purification were performed by a silica gel chromatography (mobile phase: hexane/chloroform), so that a yellow solid compound XX-14 was obtained (760 mg, yield: 73%).

Subsequently, the example compound A-40 is synthesized. In a 50-ml reaction chamber, 750 mg (1.44 mmol) of the compound XX-14 and 4.88 g (28.8 mmol) of 2-iodopropane were mixed in a mixed solvent of acetonitrile/water (20 ml/8 ml), and dissolved oxygen was removed by nitrogen. Next, 1.47 g (7.18 mmol) of sodium hydrosulfite and 1.19 g (8.61 mmol) of potassium carbonate were added in a nitrogen atmosphere, and a reaction was performed by heating and refluxing at 90° C. for 10 hours. After the reaction solution was cooled to room temperature and was then condensed at a reduced pressure, separation and purification were performed by a silica gel chromatography (mobile phase: hexane/toluene), so that a solid example compound A-40 was obtained (580 mg, yield: 66%).

According to the result of NMR measurement, the ratio of peak integration values well coincided with that of the structure, so that the obtained compound was identified as the example compound A-40. The measurement result of the NMR spectrum is shown below.

$^1$H-NMR (deuterated acetone) δ(ppm): 7.21 (t, 1H), 7.19 (t, 1H), 6.97 (s, 2H), 6.89 (s, 1H), 6.83 (s, 1H), 6.75-6.66 (m, 5H), 4.45 (sep, 1H), 4.42 (sep, 1H), 3.72 (s, 3H), 3.69 (s, 3H), 3.33 (sep, 1H), 2.30 (s, 3H), 1.64 (br, 6H), 1.38 (br, 6H), 1.17 (d, 12H).

Example 19

<Evaluation of Neutral Transparency and Electrochromic Characteristics>

As were Examples 3 and 4, the absorption spectra in a decolored state (neutral state) and a colored state (oxidized state) of each of the example compound F-14 of Example 16, the example compound B-30 of Example 17, and the example compound A-40 of Example 18 were measured. The wavelength of the absorption edge in a decolored state (neutral state) and the wavelength (absorption wavelength) λ$_{max}$ of the absorption peak in a colored state (oxidized state) of each compound are shown in Table 6.

TABLE 6

| Compound | Neutral Absorption Edge (nm) | Color Absorption Wavelength λ$_{max}$ (nm) |
|---|---|---|
| F-14 | 400 | 607 |
| B-30 | 400 | 579 |
| A-40 | 400 | 592 |

As shown in Table 6, the example compounds F-14, B-30, and A-40 each have an absorption peak in a long wavelength region of 540 nm or more in an oxidized state. This oxidized colored state was again returned to a colorless transparent state by reduction, so that the reversible electrochromic characteristics in association with oxidation and reduction were confirmed.

In addition, in the example compounds F-14, B-30, and A-40 each having a methyl group at the 1-position of the phenazine ring, the absorption edges in a neutral state are each located at 400 nm, and the transparency in a decolored state is particularly excellent. The absorption in a neutral state of each of the example compounds F-14, B-30, and A-40 is significantly shifted to a shorter wavelength side as compared to that of the comparative compound Ref-1. Furthermore, the neutral absorption edges of the example compounds F-14, B-30, and A-40 are each more shifted to a shorter wavelength side as compared to the neutral absorption edges (all of which are located at 420 nm) of the example compounds F-2, B-9, and A-21 in each of which no methyl group is provided at the 1-position of the phenazine ring.

When the neutral absorption is shifted to a shorter wavelength side, the transparency is improved, and the light resistance against UV light is also improved. In particular, when the EC material or the EC element according to the present disclosure is used in combination with a UV cut filter in an imaging device, even if a UV cut filter which cuts light in a shorter wavelength region is used, the degradation caused by light can be suppressed.

As has thus been described, according to the above embodiments and examples, an EC organic compound having an absorption peak in a long wavelength region of 540 nm or more in a colored state can be provided. In addition, the transparency in a decolored state can be improved as compared to that in the past.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. An organic compound which has an electrochromic property,
wherein a difference between an absorption edge of the organic compound in a neutral state and an absorption peak of the organic compound in an oxidized state is 110 nm or more,
and wherein the organic compound comprises a phenazine backbone and a substituent bound to the phenazine backbone, and
the substituent includes an oxygen atom.

2. The organic compound according to claim 1,
wherein the substituent comprises a ring structure bound to the phenazine backbone,
the ring structure comprises an atom bound to the phenazine backbone and another atom next to the atom, and
the another atom has the substituent.

3. The organic compound according to claim 1, wherein the organic compound has a hydrogen bond between the phenazine backbone and the substituent.

4. The organic compound according to claim 1, wherein the difference is 110 nm or more and 150 nm or less.

5. An electrochromic device comprising:
a pair of electrodes; and
an electrochromic layer disposed between the pair of electrodes,
wherein the electrochromic layer contains the organic compound according to claim 1.

6. The electrochromic device according to claim 5,
wherein the electrochromic layer further contains a different organic compound from the organic compound, and
the different organic compound is different in absorption wavelength.

7. The electrochromic device according to claim 5,
wherein the electrochromic layer includes a liquid containing an electrolyte and the organic compound.

8. An optical filter comprising:
the electrochromic device according to claim 5; and
an active element connected to one of the pair of electrodes of the electrochromic device.

9. A lens unit comprising:
the optical filter according to claim 8; and
an imaging optical system including a plurality of lenses.

10. An imaging apparatus comprising:
the electrochromic device according to claim 5; and
an imaging element receiving light which passes through the electrochromic device.

11. A window material comprising:
a pair of substrates;
the electrochromic device according to claim 5 disposed between the pair of substrates; and
an active element connected to the electrochromic device.

12. A vehicle comprising:
a body and a window provided on the body,
the window comprising the electrochromic device according to claim 5.

* * * * *